(12) United States Patent
Araldi et al.

(10) Patent No.: US 6,506,761 B1
(45) Date of Patent: Jan. 14, 2003

(54) SUBSTITUTED HYDRAZINYL HETEROAROMATIC INHIBITORS OF THROMBIN

(75) Inventors: Gian Luca Araldi, San Diego, CA (US); Joseph Edward Semple, San Diego, CA (US)

(73) Assignee: Corvas International, Inc., San Diego, CA (US)

( * ) Notice: Subject to any disclaimer, the term of this patent is extended or adjusted under 35 U.S.C. 154(b) by 0 days.

(21) Appl. No.: 09/550,091

(22) Filed: Apr. 14, 2000

(51) Int. Cl.[7] .................. A61K 31/4965; C07D 241/20
(52) U.S. Cl. .................... 514/255.05; 544/405
(58) Field of Search ...................... 544/405; 514/255.05

(56) References Cited

U.S. PATENT DOCUMENTS 6,093,717 A * 7/2000 Sanderson et al. .......... 514/253
6,147,078 A * 11/2000 Sanderson et al. .......... 514/252

FOREIGN PATENT DOCUMENTS

| EP | 0936 216 A1 | 8/1999 |
| WO | WO 97/40024 | 10/1997 |

* cited by examiner

*Primary Examiner*—Richard L. Raymond
(74) *Attorney, Agent, or Firm*—Suzanne L. Biggs; Pillsbury Winthrop LLP

(57) ABSTRACT

Compound of the invention are active as inhibitors of Thrombin and are useful in treating disease states in mammals which are characterized by abnormal thrombosis and have the following structure:

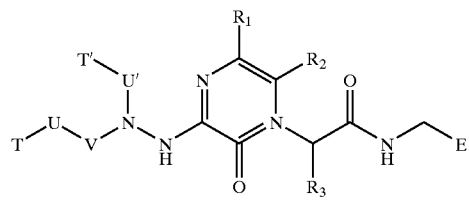

as described herein.

33 Claims, 13 Drawing Sheets

| COMPOUND NUMBER | STRUCTURE |
|---|---|
| 1 | 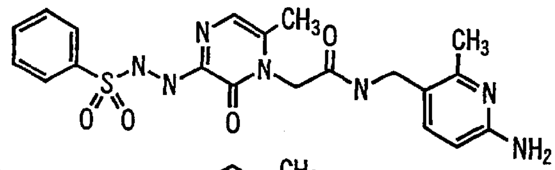 |
| 2 | 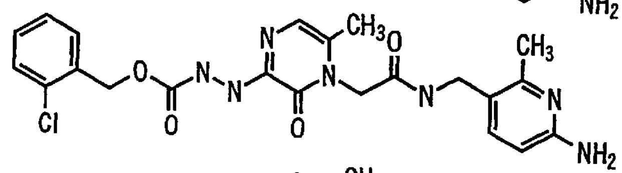 |
| 3 | 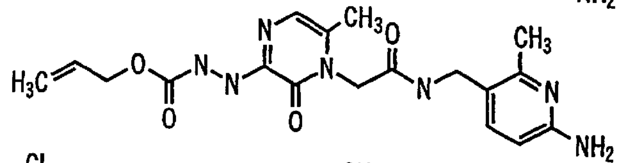 |
| 4 | 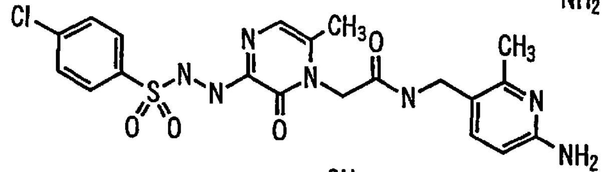 |
| 5 | 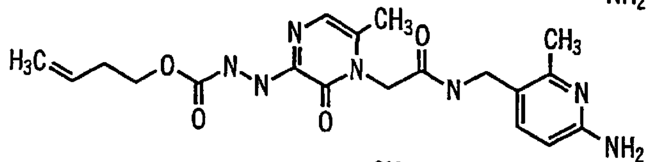 |
| 6 | 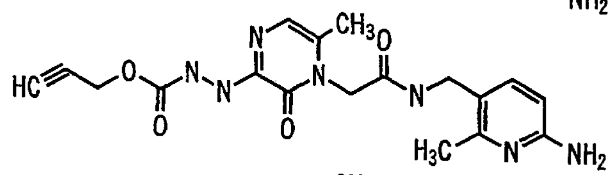 |
| 7 | 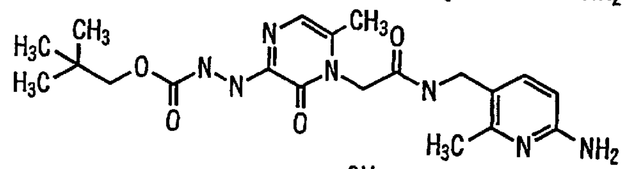 |
| 8 | 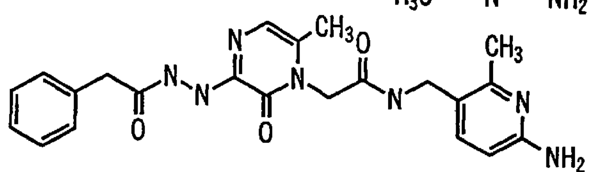 |
| 9 | 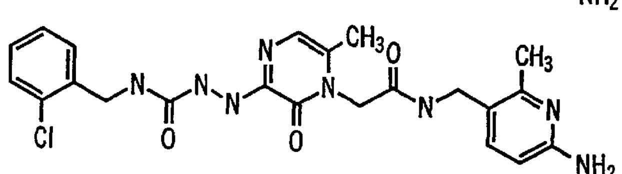 |
| 10 | 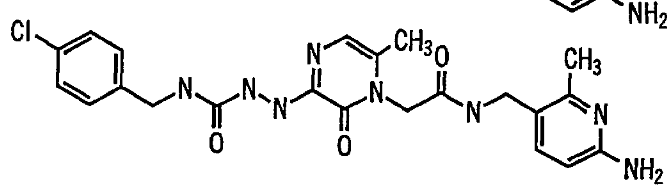 |

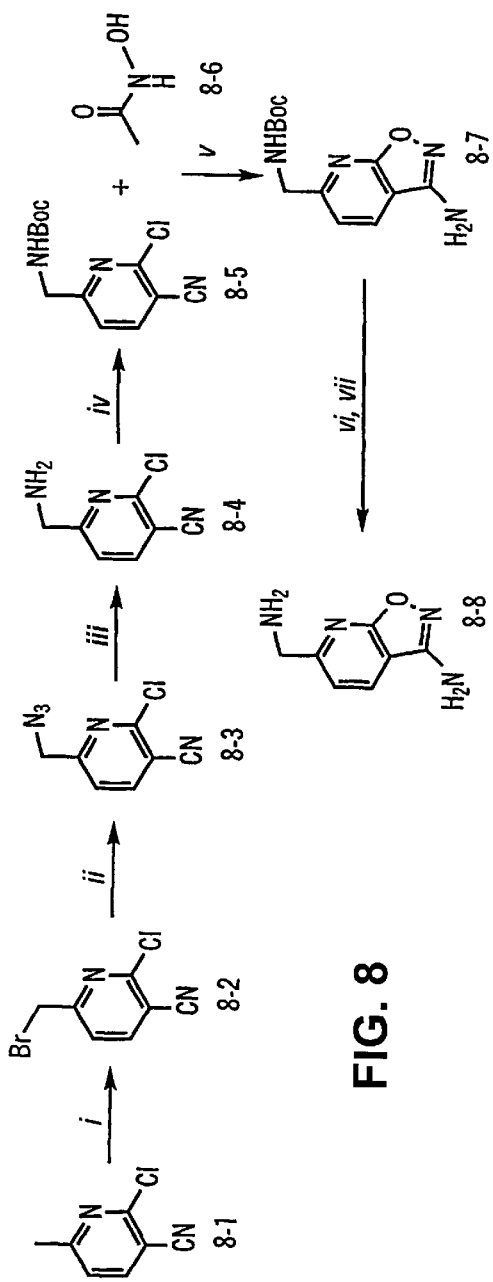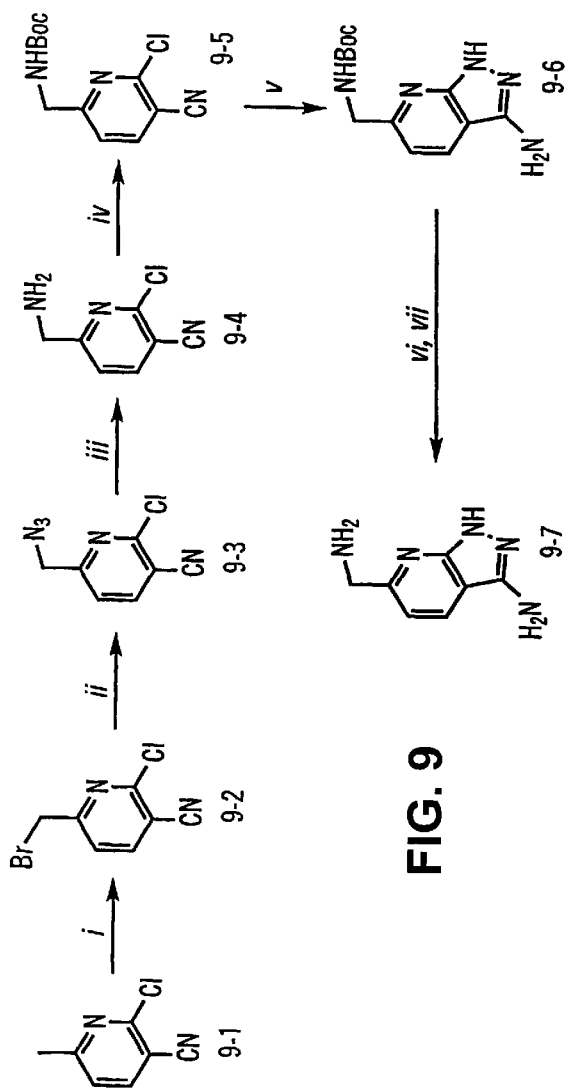
FIG. 8
FIG. 9

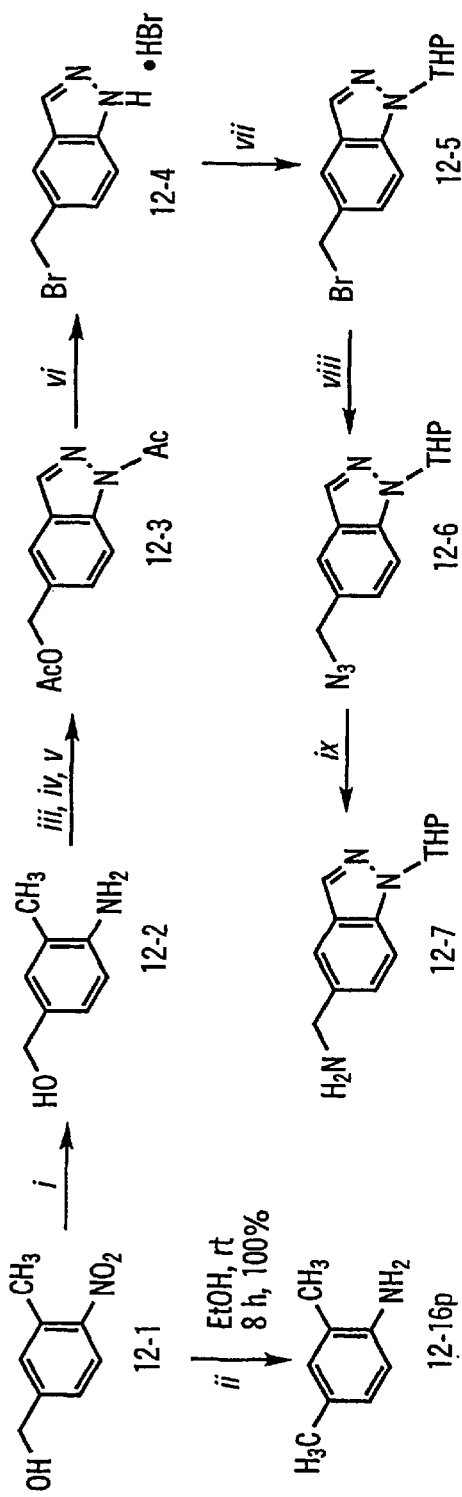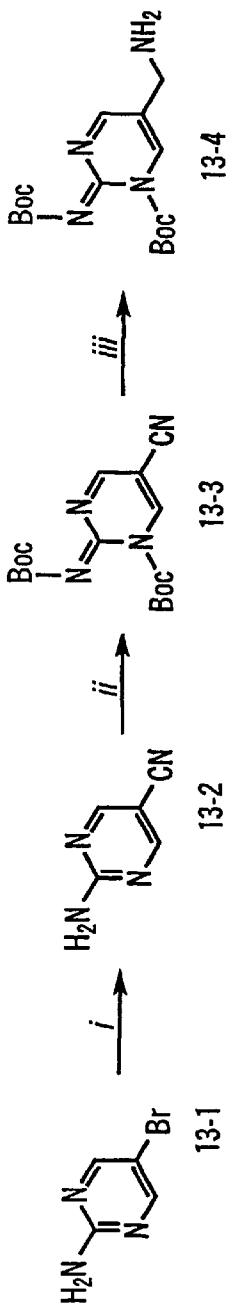

R is H, CH₃ or CH₂CH₃
R' is H or NH₂
R" is H, halogen, methoxy or CF₃

R is H, CH$_3$ or CH$_2$CH$_3$
R' is H or NH$_2$
R" is H, halogen, methoxy or CF$_3$

SUBSTITUTED HYDRAZINYL HETEROAROMATIC INHIBITORS OF THROMBIN

TECHNICAL FIELDS

In one aspect, the present invention relates to compounds which are potent inhibitors of thrombin. In another aspect, the present invention relates to novel peptide analogs, their pharmaceutically acceptable salts, and pharmaceutically acceptable compositions thereof, which are useful as potent inhibitors of blood coagulation in vitro and in vivo in mammals. In yet another aspect, the invention relates to methods of using these inhibitors as therapeutic agents for disease states in mammals characterized by abnormal thrombosis. In a further aspect, the present invention relates to methods of using these inhibitors as in vitro diagnostic agents.

BACKGROUND AND INTRODUCTION TO THE INVENTION

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury occurs. Damage to the endothelial barrier lining the vascular wall exposes underlying tissue to these blood components. This in turn triggers a series of biochemical reactions altering the hemostatic balance in favor of blood coagulation which can either result in the desired formation of a hemostatic plug stemming the loss of blood or the undesirable formation of an occlusive intravascular thrombus resulting in reduced or complete lack of blood flow to the affected organ.

The blood coagulation response is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix composed of fibrin and cellular components which is required for the stabilization of the primary hemostatic plug or thrombus. The initiation and propagation of the proteolytic activation reactions occurs through a series of amplified pathways which are localized to membranous surfaces at the site of vascular injury (Mann, K. G., Nesheim, M. E., Church, W. R., Haley, P. and Krishnaswamy, S. (1990) Blood 76: 1–16. and Lawson, J. H., Kalafatis, M., Stram, S., and Mann, K. G. (1994) J. Biol. Chem. 269: 23357–23366).

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va, and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic mechanisms", *Disorders of Hemostasis*, pp. 27–29, Grune & Stratton, Inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et al., "Surface-Dependent Reactions of the Vitamin K-Dependent Enzyme Complexes," *Blood*, 76:1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", *J. Clin. Invest.*, 71:1383–1391 (1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., *Arch. Biochem. Biophys.*, 105:58 (1964). Beyond its direct role in the formation and stabilization of fibrin rich clots, the enzyme has been reported to have profound bioregulatory effects on a number of cellular components within the vasculature and blood. Shuman, M. A., *Ann. NY Acad. Sci.*, 405:349 (1986).

It is believed that thrombin is the most potent agonist of platelet activation, and it has been demonstrated to be the primary pathophysiologic-mediator of platelet-dependent arterial thrombus formation. Edit, J. F. et al., *J. Clin. Invest.*, 84:18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C.

and Phillips, D. R., *Platelets in Biology and Pathology*, pp. 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., *Blood*, 77:2641 (1991). This positive feedback process results in the local generation of large concentrations of thrombin within the vicinity of the thrombus which supports further thrombus growth and extension. Mann, K. G. et al., *Blood*, 76:1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., *Biochemistry*, 27:769, (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., *Science*, 235:1348 (1987). The activation of protein C by thrombin in the absence of thrombomodulin is poor.

Thrombin has also been shown to be a potent direct mitogen for a number of cell types, including cells of mesenchymal, origin such as vascular smooth muscle cells. Chen, L. B. and Buchanan, J. M., *Proc. Natl. Acad. Sci. USA*, 72:131 (1975). The direct interaction of thrombin with vascular smooth muscle also results in vasoconstriction. Walz, D. A. et al., *Proc. Soc. Expl. Biol. Med.*, 180:518 (1985). Thrombin acts as a direct secretagogue inducing the release of a number of bioactive substances from vascular endothelial cells including tissue plasminogen activator. Levin, E. G. et al., *Thromb. Haemost.*, 56:115 (1986). In addition to these direct effects on vascular cells, the enzyme can indirectly elaborate potent mitogenic activity on vascular smooth muscle cells by the release of several potent growth factors (e.g. platelet-derived growth factor and epidermal growth factor) from platelet a-granules following thrombin-induced activation. Ross, R., *N. Engl. J. Med.*, 314:408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., *Thrombosis in Cardiovascular Disorder*, p. 327, W. B. Saunders Co. (Fuster, V. and Verstraete, M. edit. 1991); Califf, R. M. and Willerson, J. T., id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., *J. Am. Coll. Cardiol.*, 67:3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., *J. Am. Coll. Cardiol.*, 17:2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aa chain of fibrinogen, which is the primary physiological substrate for thrombin, is reported to contain a glycine residue in this position while the cleavage site on the Bb chain contains a serine, as shown below:

```
P4  P3  P2  P1  P1'
Gly-Gly-Val-Arg/Gly Fibrinogen Aa Chain
[SEQ. ID. NO. 1]

Phe-Ser-Ala-Arg/Gly Fibrinogen Bb Chain
[SEQ. ID. NO. 2]
```

Peptidyl derivatives having an uncharged residue in the P3 position are said to bind to the active site of thrombin and thereby inhibit the conversion of fibrinogen to fibrin and cellular activation have been reported. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., *Symposia Biologica Hungarica,* 25:277 (1984); Bajusz, S. et al., *J. Med. Chem.* 33:1729 (1990); Bajusz, S. et al., *Int. J. Peptide Protein Res.* 12:217 (1970); Kettner, C. and Shaw, E., *Methods Enzymol.,* 80:826 (1987); Kettner, C. et al., EP 293,881 (published Dec. 7, 1988); Kettner, C., et al., *J. Biol. Chem.,* 265:18209 (1990). These molecules have been reported to be potent anticoagulants in the prevention of platelet-rich arterial thrombosis. Kelly, A. B. et al., *Thromb. Haemostas.,* 65:736 at abstract 257 (1991). Other peptidyl aldehydes have been proposed or reported as inhibitors of thrombin. See, e.g., Bey, P. et al., EP 363,284 (published Apr. 11, 1990) and Balasubramanian, N. et al., EP 526,877 (published Feb. 10, 1993).

Peptidyl compounds which are said to be active site inhibitors of thrombin but which differ in structure from those containing an uncharged amino acid in the P3 recognition subsite have been reported.

The compound, Argatroban (also called 2R,4R-4-methyl-1-[N-2-(3-methyl-1,2,3,4-tetrahydro-8-qui nolinesulfonyl)-L-argininyl]-2-piperdinecarboxylic acid), is also reported to bind directly to the active site of thrombin and has been thought to be the most potent and selective compound in the class of non-peptidyl inhibitors of this enzyme. Okamoto, S. et al., *Biochem. Biophys. Res. Commun.,* 101:440 (1981). Argatroban has been reported to be a potent antithrombotic agent in several experimental models of acute arterial thrombosis. Jang, I. K. et al., in both *Circulation,* 81:219 (1990) and *Circ. Res.,* 67:1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., *Thromb. Haemostas.,* 66:141 (1991). Hirudin is reported to be a 65 amino acid polypeptide originally isolated from leech salivary gland extracts. It is said to be one of the most potent inhibitors of thrombin known. Marki, W. E. and Wallis, R. B., *Thromb. Haemostas.,* 64:344 (1990). It has been reported to inhibit thrombin by binding to both its anion-binding exo-site and to its catalytic active site which are distinct and physically distant from each other. Rydel, T. J. et al., *Science,* 249:277 (1990). Hirudin has been reported to be a potent antithrombotic agent in vivo. Markwardt, F. et al., *Pharmazie,* 43:202 (1988); Kelly, A. B. et al., *Blood,* 77:(1991). In addition to its antithrombotic effects, hirudin has been reported to also effectively inhibit smooth muscle proliferation and the associated restenosis following mechanical damage to an atherosclerotic rabbit femoral artery. Sarembock, I. J. et al., *Circulation,* 84:232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., *J. Biol. Chem.,* 264:8692 (1989); Naski, M.C. et al., *J. Biol. Chem.,* 265:13484 (1990). The region of hirudin represented by hirugen has been reported, as according to by x-ray crystallographic analysis, to bind directly to the exo site of thrombin. Skrzypczak-Jankun, E. et al., *Thromb. Haemostas.,* 65:830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, U. W. et al., *J. Biol. Chem.,* 266:16977 (1991). Hirugen also is reported to block thrombin-mediated platelet aggregation. Jakubowski, J. A. and Maraganore, J. M., *Blood,* 75:399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., *Biochemistry,* 29:7095 (1990). The hirulogs have been reported to be an effective antithrombotic agents in preventing both fibrin-rich and platelet-rich thrombosis. Maraganone, J. M. et al., *Thromb. Haemostas.,* 65:651 at abstract 17 (1991).

Certain benzamidines have been reported to inhibit thrombin though non-selectively. 4-amidinophenylpyruvic acid (APPA) has been reported to be a thrombin inhibitor with low toxicity and favorable pharmacokinetics. However, this compound was reported to be non-selective, inhibiting trypsin, plasmin and kallikrein. Markwardt et al., *Thromb. Res.,* 1:243–52 (1972). Other benzamidine-derived structures which have been reported to inhibit thrombin include the cyclic amides of $N^\alpha$-substituted 4-amidinophenylalanine and 2-amino-5-(4-amidinophenyl)-1-valeric acid. The inhibitory constant displayed by these compounds was reported to be in the micromolar range. Markwardt et al., *Thromb. Res.,* 17:425–31 (1980). Moreover, derivatives of 4-amidinophenylalanine whose $\alpha$-amino group is linked to the arylsulfonyl residue via a $\omega$-aminoalkylcarboxylic acid as spacer have also been assessed for their inhibitory effect. Among these $N^\alpha$-(2-naphthylsulphonylglycyl)-4-amidinophenylalanine piperidide (a-NAPAP) has been reported to possess an affinity for thrombin ($K_i=6\times10^{-9}$ M). Banner et al., *J. Biol. Chem.,* 266:20085 (1991) and Sturzebecher et al., *Thromb. Res.,* 29:635–42 (1983).

Certain bis-benzamidines have been reported to inhibit thrombin. The antithrombin activity of bis-benzamidines was reported to increase with the length and bulkiness of the central chain. However, these compounds were reported to be generally toxic in the micromolar range where they are also inhibitory. Geratz et al., *Thromb. Diath. Haemorrh.,* 29:154–67 (1973); Geratz et al., *J. Med. Chem.,* 16:970–5 (1973); Geratz et al., *J. Med. Chem.,* 19:634–9 (1976); Walsmann et al., *Acta Biol. Med. Germ.,* 35:K1–8 (1976); and Hauptmann et al., *Acta Biol. Med. Germ.,* 35:635–44 (1976).

Certain amidino-bearing aromatic ring structures such as β-naphthamidines have been reported to possess modest antithrombin and anticoagulant activity. This class of compounds include the non-selective 6-amidino-2-naphthyl-4-guanidinobenzoate dimethanesulfonate (FUT 175). Fuji et al., *Biochim. Biophys. Acta,* 661:342–5 (1981); and Hitomi et al., *Haemostasis,* 15:164–8 (1985).

Certain phenylguanidines have been reported to inhibit thrombin. Derivatives of 4-guanidinophenylalanine with inhibitory constants in the micromolar range have been reported to inhibit thrombin. This class includes the $N^\alpha$-tosylated and dansylated 4-guanidino phenylalanine piperidides. Claeson et al., *Thromb. Haemostas.,* 50:53 (1983). Another compound, [ethyl p-(6-guanidinohexanoyloxy) benzoate] methane sulfonate (FOY) was reported to be a non-selective competitive inhibitor of thrombin. Ohno et al., Thromb. Res., 19:579–588 (1980).

Certain compounds having inhibitory activity toward serine proteases, including thrombin, factor Xa, and trypsin, are disclosed within the following commonly assigned United States patents or published PCT applications: U.S. Pat. Nos. 5,371,072; 5,492,895; 5,534,498; 5,597,804; 5,637,599; 5,646,165; 5,656,600; 5,656,645; WO 94/13693; WO 95/35311; WO 95/35313; WO 96/19493.

Substances which interfere in the process of blood coagulation (anticoagulants) have been demonstrated to be important therapeutic agents in the treatment and prevention of thrombotic disorders (Kessler, C. M. (1991) Chest 99: 97S–112S and Cairns, J. A., Hirsh, J., Lewis, H. D., Resnekov, L., and Theroux, P. (1992) Chest 102: 456S–481S). The currently approved clinical anticoagulants have been associated with a number of adverse effects owing to the relatively non-specific nature of their effect on the blood coagulation cascade (Levine, M. N., Hirsh, J., Landefeld, S., and Raskob, G. (1992) Chest 102: 352S–363S). This has stimulated the search for more effective anticoagulant agents which can more effectively control the activity of the coagulation cascade by selectively interfering with specific reactions in this process which may have a positive effect in reducing the complications of anticoagulant therapy (Weitz, J., and Hirsh, J. (1993) J. Lab. Clin. Med. 122:364–373). In another aspect, this search has focused on normal human proteins which serve as endogenous anticoagulants in controlling the activity of the blood coagulation cascade. In addition, various hematophageous organisms have been investigated because of their ability to effectively anticoagulate the blood meal during and following feeding on their hosts suggesting that they have evolved effective anticoagulant strategies which may be useful as therapeutic agents.

SUMMARY OF THE INVENTION

The present invention is directed to novel compounds having a hydrazinyl linkage at P4-P3 and which feature a bicyclic ring group at P1. These compounds have activity as inhibitors of thrombin.

Thus, according to one aspect, the present invention is directed to compounds of the formula (I):

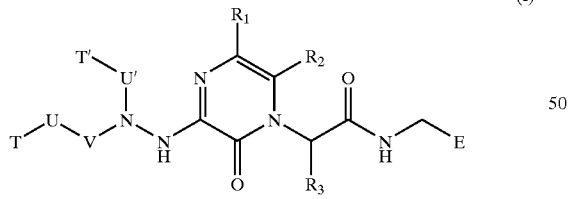

(I)

wherein:
(a) V is selected from the group consisting of —O—C(=O)—, —C(=O)—NH—C(=O)—, —NH—C(=O)—, —C(=O)—, —O—C(=S)—, —NH—S(O)$_2$—, —S(O)$_2$—, and a direct link;
(b) U and U' are independently selected from the group consisting of $C_{1-3}$ alkylene, $C_{1-3}$ alkylene substituted with $C_{1-3}$ alkyl and a direct link;
(c) T and T' are independently selected from the group consisting of
(1) $C_{1-6}$ alkyl, $C_{2-6}$ alkenyl, $C_{2-6}$ alkynyl,
(2) $C_{1-6}$haloalkyl, $C_{3-6}$haloalkenyl, $C_{3-6}$haloalkynyl;
(3) $C_{2-6}$oxaalkyl, $C_{3-6}$oxaalkenyl, $C_{3-6}$oxaalkynyl;
(4) $C_{1-6}$hydroxyalkyl, $C_{3-6}$hydroxyalkenyl, $C_{3-6}$hydroxyalkynyl;
(5) $C_{1-6}$carboxyalkyl, $C_{2-6}$carboxyalkenyl, $C_{2-6}$carboxyalkynyl;
(6) —$C_{1-3}$alkyl-carbonyl-$C_{1-3}$alkyl, —$C_{2-4}$alkenyl-carbonyl-$C_{2-4}$alkenyl, —$C_{2-4}$alkynyl-carbonyl-$C_{2-4}$alkynyl;
(7) $C_{1-6}$nitroalkyl, $C_{2-6}$nitroalkenyl, $C_{2-6}$nitroalkynyl;
(8) $C_{1-6}$alkylamine, $C_{2-6}$alkenylamine, $C_{2-6}$alkynylamine;
(9) $C_{1-6}$alkylimine, $C_{2-6}$alkenylimine, $C_{2-6}$alkynylimine;
(10) $C_{1-6}$alkylamide, $C_{2-6}$alkenylamide, $C_{2-6}$alkynylamide;
(11) $C_{1-6}$alkylcarbamoyl, $C_{2-6}$alkenylcarbamoyl, $C_{2-6}$alkynylcarbamoyl;
(12) $C_{1-6}$alkylurea; $C_{2-6}$alkenylurea; $C_{2-6}$alkynylurea;
(13) $C_{1-6}$alkylhydrazine, $C_{2-6}$alkenylhydrazine, $C_{2-6}$alkynylhydrazine;
(14) $C_{1-6}$alkylnitrile, $C_{2-6}$alkenylnitrile, $C_{2-6}$alkynylnitrile;
(15) $C_{1-6}$alkylazide, $C_{2-6}$alkenylazide, $C_{2-6}$alkynylazide;
(16) $C_{1-6}$thioalkyl, $C_{3-6}$thioalkenyl, $C_{3-6}$thioalkynyl;
(17) $C_{1-6}$alkylthiol, $C_{2-6}$alkenylthiol, $C_{3-6}$alkynylthiol;
(18) $C_{3-6}$alkylisothiol, $C_{3-6}$alkenylisothiol, $C_{4-6}$alkynylisothiol;
(19) —$C_{1-6}$alkyl-thionyl-$C_{1-6}$alkyl, —$C_{2-6}$alkenyl-thionyl-$C_{2-6}$alkenyl, —$C_{2-6}$alkynyl-thionyl-$C_{2-6}$alkynyl;
(20) —$C_{1-6}$alkyl-sulphuryl-$C_{1-6}$alkyl, —$C_{2-6}$alkenyl-sulphuryl-$C_{2-6}$alkenyl, —$C_{2-6}$alkynyl-sulphuryl-$C_{2-6}$alkynyl;
(21) $C_{1-6}$alkylsulphonyl, $C_{2-6}$alkenylsulphonyl, $C_{2-6}$alkynylsulphonyl;
(22) $C_{1-6}$alkylsulphonamide, $C_{2-6}$alkenylsulphonamide, $C_{2-6}$alkynylsulphonamide;
(23) $C_{3-7}$cycloalkyl, halo-$C_{3-7}$cycloalkyl, $C_{3-7}$cycloalkyl-$C_{1-6}$alkyl, $C_{3-7}$cycloalkyl-di($C_{1-6}$alkyl), $C_{3-7}$cycloalkyl-$C_{3-6}$alkenyl, —$C_{3-7}$cycloalkyl-$C_{3-6}$alkynyl;
(24) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, which is optionally mono-, di-, or tri-substituted on the ring with $Y_1$, $Y_2$ and/or $Y_3$;
(25) heterocyclo of 4 to about 10 ring atoms with the ring atoms selected from carbon and heteroatoms, wherein the heteroatoms are selected from the group consisting of oxygen, nitrogen, and S(O)$_i$, including

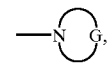

wherein

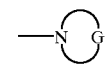

is a 5 to 7 member heterocycle of 3 to 6 ring carbon atoms, where G is —CH$_2$—, —O—, —S(=O)—, —S(O)$_2$— or —S—, which is optionally mono-, di-, or tri-substituted on the ring carbons with $Y_1$, $Y_2$ and/or $Y_3$;

(26) aryl of about 6 to about 14 carbon atoms which is optionally mono-, di- or tri-substituted with $Y_1$, $Y_2$, and/or $Y_3$;

(27) heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$, and/or Y3;

(28) aralkyl of about 7 to about 15 carbon atoms which is optionally substituted on the alkyl chain with hydroxy or halogen and mono-, di-, or tri-substituted in the aryl ring with $Y_1$, $Y_2$, and/or $Y_3$;

(29) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$;

(30) aralkenyl of about 8 to about 16 carbon atoms which is optionally mono-, di-, or tri-substituted on the aryl ring with $Y_1$, $Y_2$, and/or $Y_3$;

(31) heteroaralkenyl of 5 to 14 ring atoms with the ring atoms selected from carbon and heteroatoms, wherein the heteroatoms are selected from oxygen, nitrogen, and sulfur, and which is optionally mono-, di- or tri-substituted on the ring with $Y_1$, $Y_2$, and/or $Y_3$;

(32) fused carbocyclic of about 5 to about 13 carbon atoms, optionally substituted with $Y_1$, $Y_2$ and/or $Y_3$;

(33) fused carbocyclic alkyl of about 6 to about 16 carbon atoms, optionally substituted with $Y_1$, $Y_2$ and/or $Y_3$; and

(34) hydrogen;

(d)

(1) each $Y_1$, $Y_2$, and $Y_3$ is independently selected from the group consisting of halogen, cyano, nitro, tetrazolyl optionally substituted with alkyl of 1 to about 6 carbon atoms, guanidino, amidino, methylamino, methylguanidino, $-CF_3$, $-CF_2CF_3$, $-CH(CF_3)_2$, $-C(OH)(CF_3)_2$, $-OCF_3$, $-OCF_2CF_3$, $-OCF_2H$, $-OC(O)NH_2$, $-OC(O)NHZ_1$, $-OC(O)NZ_1Z_2$, $-NHC(O)Z_1$, $-NHC(O)NH_2$, $-NHC(O)NHZ_1$, $-NHC(O)NZ_1Z_2$, $-C(O)OH$, $-C(O)OZ_1$, $-C(O)NH_2$, $-C(O)NZ_1Z_2$, $-P(O)_3H_2$, $-P(O)_3(Z_1)_2$, $-S(O)_3H$, $-S(O)_pZ_1$, $-Z_1$, $-OZ_1$, $-OH$, $-NH_2$, $-NHZ_1$, $-NZ_1Z_2$, N-morpholino, nitro, $-C\equiv N$, and $-S(O)_p(CF_2)_qCF_3$, wherein p is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 5 to about 14 ring atoms having about 3 to about 9 carbon atoms, or (2) $Y_1$ and $Y_2$ are selected together to be $-O[C(Z_3)(Z_4)]_rO-$ or $-O[C(Z_3)(Z_4)]_{r+1}-$, wherein r is an integer from 1 to 4 and $Z_3$ and $Z_4$ are independently selected from the group consisting of hydrogen, alkyl or 1 to about 12 carbon atoms, aryl of about 6 to about 14 carbon atoms, heteroaryl of about 5 to about 14 ring atoms having 1 to about 9 carbon atoms, aralkyl of about 7 to about 15 carbon atoms, and heteroaralkyl of about 5 to about 14 ring atoms having about 3 to about 9 carbon atoms;

(e) $R_1$ is selected from hydrogen, halogen, and methyl;

(f) $R_2$ is selected from hydrogen, $C_{1-4}$alkyl, $C_{3-7}$cycloalkyl, and $CF_3$;

(g) $R_3$ is hydrogen or $C_{1-4}$ alkyl; and (h) E is:

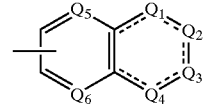

wherein (1) $Q_1$ is $C(R_8)$, $C(R_9)(R_{9a})$, N,N($R_{8a}$), or a direct link;

(2) $Q_2$ is C ($R_8$), $C(R_{10})(R_{10a})$, N,N($R_8$) S, or O;

(3) $Q_3$ is $C(R_8)$, $C(R_{11})(R_{11a})$, N or N($R_{8a}$)

(4) $Q_4$ is C ($R_8$), $C(R_{12})$ ($R_{12a}$), N, N ($R_{8a}$), S, or O;

(5) $Q_5$ is $C(R_{13})$, $C(R_{13})(R_{13a})$ or N;

(6) $Q_6$ is $C(R_{14})$, $C(R_{14})(R_{14a})$ or N;

(7) $R_8$ is $NR_{15}R_{16}$ or $-OR_{15}$;

(8) $R_{8a}$ is hydrogen, alkyl of 1 to about 3 carbon atoms, $NR_{15a}R_{16a}$ a or $-OR_{15a}$;

(9) $R_9$, $R_{10}$, $R_{11}$, $R_{12}$, $R_{13}$, and $R_{14}$ are independently selected from hydrogen, alkyl of 1 to about 3 carbon atoms substituted with alkoxy of 1 to about 3 carbon atoms, alkoxy of 1 to about 4 carbon atoms; halogen and trifluoromethyl;

(10) $R_{9a}$, $R_{10a}$, $R_{11a}$ $R_{12a}$, $R_{13a}$ and $R_{14a}$ are independently hydrogen or absent;

(11) $R_{15}$ and $R_{15a}$ are independently hydrogen, alkyl of 1 to about 3 carbon atoms, or $-C(=O)R_{17}$;

(12) $R_{16}$ and $R_{16a}$ are independently hydrogen or alkyl of 1 to about 3 carbon atoms;

(13) alternatively, R15 and $R_{16}$ or $R_{15a}$ and $R_{16a}$ taken together form a divalent radical of the formula $-(CH_2)_w-$, where w is independently 3, 4 or 5; and

(14) $R_{17}$ is alkyl of 1 to about 6 carbon atoms or alkoxy of 1 to about 6 carbon atoms;

with the provisos that:

(i) no more than two of $Q_1$, $Q_2$, $Q_3$ and $Q_4$ can be $C(R_8)$ or $N(R_{8a})$;

(ii) at least one of $Q_1$, $Q_2$, $Q_3$ and $Q_4$, but not all, is N or $N(R_{8a})$;

(iii) only one of $Q_2$ and $Q_4$ can be O or S; and (iv) $Q_1$, $Q_2$, $Q_3$ and $Q_4$ are not all heteroatoms;

and pharmaceutically acceptable salts thereof.

In one aspect, the present invention is directed to compounds which are potent inhibitors of thrombin. According to a preferred aspect, these compounds comprise novel serine protease inhibitors and the invention is also directed to pharmaceutical compositions which comprise one of these compounds and a pharmaceutically acceptable carrier. These compounds and pharmaceutical compositions are potent inhibitors of blood coagulation in vitro and in vivo in mammals. These compounds and pharmaceutical compositions may be used as therapeutic agents for treating disease states in mammals which are characterized by abnormal thrombosis. A further aspect of the present invention is directed to the use of these compounds and pharmaceutical compositions for treatment of disease states in mammals characterized by abnormal thrombosis. An alternate aspect of the present invention is directed to methods of using these thrombin inhibitors as in vitro diagnostic agents.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound of the present invention or pharmaceutical composition comprising such a compound.

Definitions

In accordance with the present invention and as used herein, the following terms are defined to have following meanings, unless explicitly stated otherwise:

In referring to formula (I), P1, P2, P3 and P4 denote the portions of the molecule indicated below:

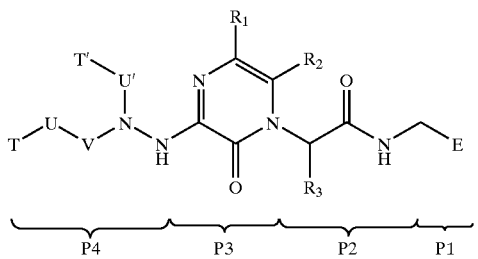

wherein $R_1$, $R_2$, $R_3$, E, T, T', U, U' and V are as defined in connection with formula (I).

The term "alkenyl" refers to unsaturated aliphatic groups having at least one double bond.

The term "alkynyl" refers to unsaturated aliphatic groups having at least one triple bond.

The term "alkyl" refers to saturated aliphatic groups including straight-chain, branched-chain and cyclic groups.

The term "alkylamide" refers to an alkyl group substituted with an amido (—C(=O)—NH$_2$) moiety.

The term "alkenylamide" refers to an alkenyl group substituted with an amido moiety.

The term "alkynylamide" refers to an alkynyl group substituted with an amido moiety.

The term "alkylamine" refers to an alkyl group substituted with an amino (—NH$_2$) moiety.

The term "alkenylamine" refers to an alkenyl group substituted with an amino moiety.

The term "alkynylamine" refers to an alkynyl group substituted with an amino moiety.

The term "alkenyl" refers to unsaturated aliphatic groups having at least one double bond.

The term "alkynyl" refers to unsaturated aliphatic groups having at least one triple bond.

The term "alkyl" refers to saturated aliphatic groups including straight-chain, branched-chain and cyclic groups.

The term "alkylamide" refers to an alkyl group substituted with an amido (—C(=O)—NH$_2$) moiety.

The term "alkenylamide" refers to an alkenyl group substituted with an amido moiety.

The term "alkynylamide" refers to an alkynyl group substituted with an amido moiety.

The term "alkylamine" refers to an alkyl group substituted with an amino (—NH$_2$) moiety.

The term "alkenylamine" refers to an alkenyl group substituted with an amino moiety.

The term "alkynylamine" refers to an alkynyl group substituted with an amino moiety.

The term "alkylazide" refers to an alkyl group substituted with an azide (—N=N=N) moiety.

The term "alkenylazide" refers to an alkenyl group substituted with an azide moiety.

The term "alkynylazide" refers to an alkynyl group substituted with an azide moiety.

The term "alkylcarbamoyl" refers to an alkyl group substituted with a carbamoyl (—O—C(=O)—NH$_2$) moiety.

The term "alkenylcarbamoyl" refers to an alkenyl group substituted with a carbamoyl moiety.

The term "alkynylcarbamoyl" refers to an alkynyl group substituted with a carbamoyl moiety.

The term "-alkyl-carbonyl-alkyl" refers to an alkyl group substituted with a carbonyl moiety (—C(=O)—) between two adjacent carbon atoms.

The term "-alkenylcarbonyl-alkenyl" refers to an alkenyl group substituted with a carbonyl moiety between two adjacent carbons. Preferably, the carbonyl is not adjacent to a double bonded carbon.

The term "-alkynylcarbonylalkynyl" refers to an alkynyl group substituted with a carbonyl moiety between two adjacent carbons. Preferably, the carbonyl is not adjacent to a triple bonded carbon.

The term "alkylhydrazine" refers to an alkyl group substituted with a hydrazinyl (—NH—NH$_2$) moiety.

The term "alkenylhydrazine" refers to an alkenyl group substituted with a hydrazinyl moiety.

The term "alkynylhydrazine" refers to an alkynyl group substituted with a hydrazinyl moiety.

The term "alkylimine" refers to an alkyl group substituted with an imino (=NH) moiety.

The term "alkenylimine" refers to an alkenyl group substituted with an imino moiety.

The term "alkynylimine" refers to an alkynyl group substituted with an imino moiety.

The term "alkylisothiol" refers to an alkyl group substituted with a sulfhydryl (—SH) moiety on an interior carbon atom.

The term "alkenylisothiol" refers to an alkenyl group substituted with a sulfhydryl moiety on an interior carbon atom.

The term "alkynylisothiol" refers to an alkynyl group substituted with a sulfhydryl group on an interior carbon atom.

The term "alkylnitrile" refers to an alkyl group substituted with a nitrile (—C≡N or cyano) moiety.

The term "alkenylnitrile" refers to an alkenyl group substituted with a nitrile moiety.

The term "alkynylnitrile" refers to an alkynyl group substituted with a nitrile moiety.

The terms "alkoxy" and "alkoxyl" refer to a group having the formula, R—O—, wherein R is an alkyl group.

The term "alkoxycarbonyl" refers to a group of the formula —C(O)OR wherein R is alkyl.

The term "alkenylphosphonyl" refers to an alkenyl group substituted with a phosphonyl moiety.

The term "alkynylphosphonyl" refers to an alkynyl group substituted with a phosphonyl moiety.

The term "alkylsulphonamide" refers to an alkyl group substituted with a sulphonamide (—S(O)$_2$—NH$_2$) moiety.

The term "alkenylsulphonamide" refers to an alkenyl group substituted with a sulphonamide moiety.

The term "alkynylsulphonamide" refers to an alkynyl group substituted with a sulphonamide group.

The term "alkylsulphonyl" refers to an alkyl group substituted with a sulphonyl (—S(O)$_2$—C— or —S(Q)$_2$—OH) moiety.

The term "alkenylsulphonyl" refers to an alkenyl group substituted with a sulphonyl moiety.

The term "alkynylsulphonyl" refers to an alkynyl group substituted with a sulphonyl moiety.

The term "alkylsulphurylalkyl" refers to an alkyl group substituted with a sulphuryl (—S(O)$_2$—) moiety between two adjacent carbons.

The term "alkenylsulphurylalkenyl" refers to an alkenyl group substituted with a sulphuryl group between two adjacent carbons.

The term "alkynylsulphurylalkynyl" refers to an alkynyl group substituted with a sulphuryl group between two adjacent carbon atoms.

The term "alkylthiol" refers to an alkyl group substituted with a sulphydryl (—SH) moiety on a terminal carbon atom.

The term "alkenylthiol" refers to an alkenyl group substituted with a sulphydryl group on a terminal carbon atom.

The term "alkynylthiol" refers to an alkynyl group substituted with a sulphydryl group on a terminal carbon atom.

The term "alkylthionylalkyl" refers to an alkyl group substituted with a thionyl (—S(=O)— or sulphoxide) moiety between two adjacent carbon atoms.

The term "alkenylthionylalkenyl" refers to an alkenyl group substituted with a thionyl moiety between two adjacent carbon atoms.

The term "alkynylthionylalkynyl" refers to an alkynyl group substituted with a thionyl moiety between two adjacent carbon atoms.

The term "alkylurea" refers to an alkyl group substituted with an ureido (—NH—C(=O)—NH—) moiety between two adjacent carbon atoms.

The term "alkenylurea" refers to an alkenyl group substituted with a ureido moiety between two adjacent carbon atoms. Preferably the ureido moiety is not adjacent to a double bond.

The term "alkynylurea" refers to an alkynyl group substituted with an ureido moiety between two adjacent carbon atoms. Preferably the ureido moiety is not adjacent to a triple bond.

The term "aminoalkyl" refers to an alkyl group substituted with an amino (NH$_2$) group.

The term "aralkenyl" refers to an alkenyl group substituted with an aryl group. Preferably the alkenyl group has from 2 to about 6 carbon atoms.

The term "aralkyl" refers to an alkyl group substituted with an aryl group. Suitable aralkyl groups include benzyl, and the like, all of which may be optionally substituted. Preferably the alkyl group has from 1 to about 5 carbon atoms.

The term "aryl" refers to an aromatic group which has at least one ring having a conjugated pi electron system and includes groups having one ring, biaryl groups, and aromatic groups having 2 or more fused rings, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to both natural and unnatural amino acids in their D and L stereoisomers, if their structures allow such stereoisomeric forms, and their analogs. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, demosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid residue" refers to radicals having the structure: (1) —C(O)—R—NH—, wherein R typically is —CH(R')—, wherein R' is H or a carbon containing substituent; or (2)

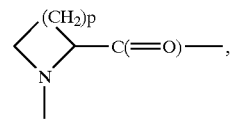

wherein p is 1, 2 or 3 representing the azetidinecarboxylic acid, proline or pipecolic acid residues, respectively.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycerine; or alanine carboxamide is an amino acid analog of alanine.

"Arginine mimic side chain" or "side chain of an arginine mimic" refers to a group of atoms which spatially and electronically resemble or mimic the normal arginine side chain. These groups include the cyclic R$_5$ groups defined in connection with formula (I).

"Biaryl" refers to a first aryl group, such as phenyl, substituted by another aryl group as defined herein, ortho, meta or para to the point of attachment of the first aryl ring.

"Brine" refers to an aqueous saturated solution of sodium chloride.

"Camphor derivative" refers to the groups:

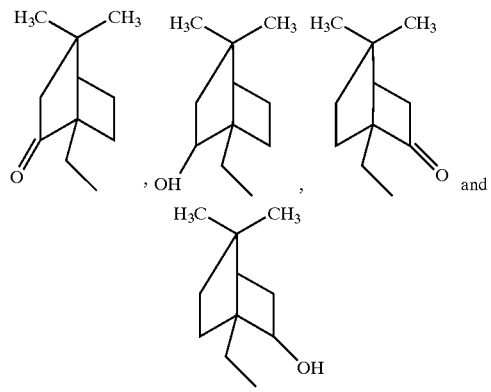

"Carbocyclic" refers to a group having one or more rings, including groups having 2 or more fused rings, wherein the ring atoms are all carbon atoms and includes groups having aryl, cycloalkyl, and unsaturated cycloalkyl or a combination of such rings. Such groups include cyclohexyl, cycloheptenyl, tetrahydronaphthyl, phenyl, naphthyl, and the like.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, nitro, and cyano. Substituted naphthyl refers to 1- or 2-naphthyl substituted by lower alkyl, lower alkoxy, or halogen.

The term "carboxyalkyl" refers to an alkyl group substituted with a carboxyl (—C(=O)OH) moiety.

The term "carboxyalkenyl" refers to an alkenyl group substituted with a carboxyl moiety.

The term "carboxyalkenyl" refers to an alkynyl group substituted with a carboxyl moiety.

"Carboxylate mimic" or "carboxylic acid mimic" refers to a group which spatially and electronically mimics a carboxylic acid and provides a net negative charge, i.e., an anion, and also has a pKa value similar to that of a corresponding carboxylic acid, preferably having a pKa of about 4 to 5.

"Cycloalkenyl" or "unsaturated cycloalkyl" refers to a cyclic alkenyl group, that is, a cycloalkyl group modified by having at least one double band. Suitable cycloalkenyl groups include, for example, cyclopentenyl and cyclohexenyl.

"Cycloalkyl" refers to a cyclic alkyl group. Suitable cycloalkyl groups include, for example, cyclohexyl, cyclopropyl, cyclopentyl, and cycloheptyl. The term "halocycloalkyl" refers to a cycloalkyl group substituted with a halogen. The term "cycloalkyl-alkyl" refers to a cycloalkyl group substituted with an alkyl group. The term "cycloalkyl-alkenyl" refers to a cycloalkyl group substituted with an alkenyl group. The term "-cycloalkyl-alkynyl" refers to a cycloalkyl group substituted with an alkynyl group.

The term "cycloalkyl-di(alkyl)" refers to a cycloalkyl group substituted with two alkyl groups.

"Cyclohexylmethyl" refers to a cyclohexyl group attached to $CH_2$.

"Fused carbocyclic" refers to a group having multiple rings which are fused, including multicyclic fused carbocyclic rings having both aromatic and non-aromatic rings. Suitable fused carbocyclic rings include fluorenyl, tetralin and the like.

"Fused carbocyclic-alkyl" refers to an alkyl group substituted with a fused carbocyclic ring moiety, preferably a multicyclic fused carbocyclic ring having both aromatic and nonaromatic rings. Suitable fused carbocyclic alkyl groups include fluorenylmethyl and the like.

The term "halogen" refers to fluorine, chlorine, bromine and iodine.

The term "halo" refers to a halogen substituent. Accordingly, "haloalkyl" refers to an alkyl group substituted with one or more halogen atoms, "haloalkenyl" refers to an alkenyl group substituted with one or more halogen atoms, and "haloalkynyl" refers to an alkynyl group substituted with one or more halogen atoms.

"Heterocyclic" refers to a group having 1 or more rings wherein the ring atoms are carbon atoms or heteroatoms, and includes rings that are reduced, saturated, unsaturated and aromatic and, if the group has more than one ring, includes a combination of such rings. Suitable heteroatoms include oxygen, nitrogen and $S(O)_i$ wherein i is 0, 1 or 2. Thus, heterocyclic groups include groups having (i) heterocyclo rings (ii) unsaturated heterocyclo rings, (iii) heteroaryl rings or (iv) a combination of such rings.

"Heteroaryl" refers to aromatic groups having a mixture of carbon atoms and heteroatoms as ring atoms and includes groups having 2 or more fused rings. Preferred heteroaryl groups include those having 5 to 14 ring atoms and from 1 to 9 carbon atoms and the remainder of the ring atoms heteroatoms. Heteroaryl groups include those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, and sulfur. Typical heteroaryl groups include furanyl, thienyl, pyridyl, pyrrolyl, pyrimidyl, pyrazinyl, imidazolyl, pyrazolyl, oxazolyl, thiazolyl and the like.

"Heteroaralkenyl" refers to an alkenyl group substituted with a heteroaryl group. Preferably the alkenyl group has from 2 to about 6 carbon atoms.

"Heteroaralkyl" refers to an alkyl group substituted with a heteroaryl group. Preferably the alkyl group has from 1 to about 6 carbon atoms.

A "heteroatom" as defined herein is an atom other than carbon or hydrogen, e.g., typically, oxygen, nitrogen or sulfur.

"Heterocyclo" refers to a reduced heterocyclic ring system comprised of carbon, nitrogen, oxygen and/or sulfur atoms, and includes such heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Unsaturated heterocyclo" refers to a heterocyclo group which is modified by having at least one double bond, but which is not aromatic.

"Heterocycloalkyl" refers to an alkyl group substituted with a heterocyclo group. Preferably the alkyl group has from 1 to about 6 carbon atoms.

The term "hydrocarbyl" denotes an organic radical composed of carbon and hydrogen which may be aliphatic (including alkyl, alkenyl and alkynyl groups and groups which have a mixture of saturated and unsaturated bonds), alicyclic (such as cycloalkyl), aromatic (such as aryl) or combinations thereof, and may refer to straight-chained, branched-chain or to cyclic structures or to radicals having a combination thereof, as well as to radicals substituted with halogen atom(s) or heteroatoms, such as nitrogen, oxygen and sulfur and their functional groups (such as amino, alkoxy, aryloxy, lactone groups, and the like), which are commonly found in organic compounds and radicals.

The term "hydroxyalkyl" refers to an alkyl group substituted with a hydroxy moiety.

The term "hydroxyalkenyl" refers to an alkenyl group substituted with an hydroxy moiety.

The term "hydroxyalkynyl" refers to an alkynyl group substituted with an hydroxy moiety.

The term "lower" referred to herein in connection with organic radicals or compounds defines such with up to and including 6, preferably up to and including 4 and advantageously one or two carbon atoms. Such groups may be straight chain or branched chain.

The terms "nitroalkyl," "nitroalkenyl" and "nitroalkynyl" refer to alkyl, alkenyl and alkynyl groups, respectively, substituted with a nitro group.

The term "oxaalkyl" refers to the group —alk—O—R wherein alk is an alkylene group and R is an alkyl group.

The term "oxaalkenyl" refers to a group where a divalent oxygen (—O—) has been inserted between two adjacent methylene (—$CH_2$—) moieties in an alkenyl group.

The term "oxaalkynyl" refers to a group where a divalent oxygen has been inserted between adjacent methylene moieties in an alkynyl group.

"Perfluoroalkyl" refers to an alkyl group which has every hydrogen replaced with fluorine.

"Perfluoroaryl" refers to an aryl group which has every hydrogen replaced with fluorine.

"Perfluoroarylalkyl" or "Perfluoroaralkyl" refers an aralkyl group in which every hydrogen on the aralkyl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

The term "quaternary ammonium salt" refers to compounds produced by reaction between a basic nitrogen in an R substituent and an alkylhalide, arylhalide, and aralkylhalide. Other reactants with good leaving groups may also be used, such as alkyl trifluoromethanesulfonates, alkyl methanesulfonates, and alkyl p-toluenesulfonates. A quaternary ammonium salt has a positively charged nitrogen in the R substituent. Pharmaceutically acceptable counterions include Cl—, Br⁻, I⁻, $CF_3C(O)O^-$ and $CH_3C(O)O^-$. The counterion of choice can be made using ion exchange resin columns. R groups with basic nitrogens include —$CH_2CH_2CH_2NHC(=NH)NH_2$,

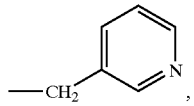

—$(CH_2)_pNH_2$, wherein p is an integer from 1 to 6. For example, the following R groups contain basic nitrogens: 3-(R)-quinuclidine, 3-(S)-quinuclidine, 3-yl-2-ethyl-4(3H)-quinazolinone, ethyl morpholine, ethyl piperidine, 2-(2-ethyl)pyridine, and 4-(methyl)-5-hydroxy-6-methyl-3- pyridine methanol.

The term "thioalkyl" refers to an alkyl group substituted with a thio (—S—) moiety between two adjacent carbon atoms.

The term "thioalkenyl" refers to an alkenyl group substituted with a thio moiety between two adjacent carbon atoms.

The term "thioalkynyl" refers to an alkynyl group substituted with a thio moiety between two adjacent carbon atoms.

"Trihydrocarbylsilyl" refers to the group

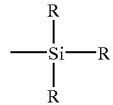

wherein each R is an independently selected hydrocarbyl group.

The term "Arg-al" refers to the residue of L-argininal which has the formula:

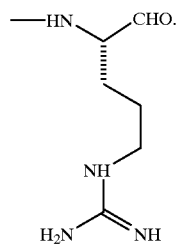

The term "argininal mimic" refers to an argininal group wherein the arginine side chain is replaced with an arginine mimic side chain.

The term "N-alpha-t-butoxycarbonyl-$N^g$-nitro-L-arginine" refers to the compound which has the formula:

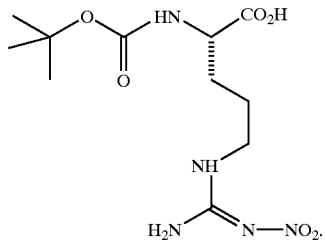

The term "terminal carbon" refers to the carbon atom of a straight chain alkyl which is furthest from the parent structure.

In addition, the following abbreviations stand for the following:

"=" when adjacent to a variable in text represents a double bond, e.g., (=X).
"Ac" refers to acetyl.
"AcOH" refers to acetic acid.
"$Ac_2O$" refers to acetic anhydride.
"Bn" refers to benzyl.
"Boc" or "BOC" refers to t-butoxycarbonyl.
"BOP" refers to benzotriazol-1-yl-oxy-tris-(dimethylamino)-phosphonium hexafluorophosphate.
"$BnSO_2$" or "$BzlSO^2$" refers to benzylsulfonyl.
"Cbz," "CBZ" or "CBz" refers to benzyloxycarbonyl.
"DCA" refers to dichloroacetic acid.
"DCC" refers to N,N'-dicyclohexylcarbodiimide.
"DCE" refers to dichloroethane.
"DCM" refers to dichloromethane (also called methylene chloride).
"DMF" refers to N,N-dimethylformamide.
"DMSO" refers to dimethyl sulfoxide.
"DMAP" refers to 4-N,N-dimethylamino-pyridine.
"EDAC" or "EDC" refers to 1-ethyl-3-(3-dimethylamino-propyl) carbodiimide hydrochloride salt.
"Et" refers to ethyl.
"$Et_3N$" refers to triethylamine.
"EtOAc" refers to ethyl acetate.
"EtOH" refers to ethanol.
"FMOC" refers to 9-fluorenylmethoxycarbonyl.
"HATU" refers to O-(7-azabenzotriazol-1-yl)-1,1,3,3-tetramethyluronium hexafluorophosphate.
"HBTU" refers to 2-(1H-benzotriazol-1-yl)-1,1,3,3-tetramethyluronium hexafluorophosphate.

"HCl" refers to hydrochloric acid.
"HOAc" refers to acetic acid.
"HOAt" refers to 1-hydroxy-7-azabenzotriazole.
"HOBt" refers to 1-hydroxybenzotriazole monohydrate.
"HPLC" refers to high pressure liquid chromatography.
"i-BuOCOCl" refers to isobutylchloroformate.
"i-PrOH" refers to isopropanol.
"LiAlH$_4$" refers to lithium aluminum hydride.
"LiAlH$_2$(OEt)$_2$" refers to lithium aluminum dihydride diethoxide.
"Me" refers to methyl.
"MeOH" refers to methanol.
"NaOH" refers to sodium hydroxide.
"NBS" refers to N-bromosuccinimide.
"NMM" refers to N-methylmorpholine.
"2-PrPen" refers to 2-propylpentanoyl.
"TBTU" refers to 2-(1H-benzotriazol-1-yl)-1,1,3,3-tetramethyluronium tetrafluoroborate.
"TFA" refers to trifluoroacetic acid.
"THF" refers to tetrahydrofuran.
"THF" refers to tetrahydrofuran.
"TLC" refers to thin layer chromatography.
"TMSCN" or "TMSiCN" refers to trimethylsilyl cyanide.

BRIEF DESCRIPTION OF THE DRAWINGS

Figure 3A:
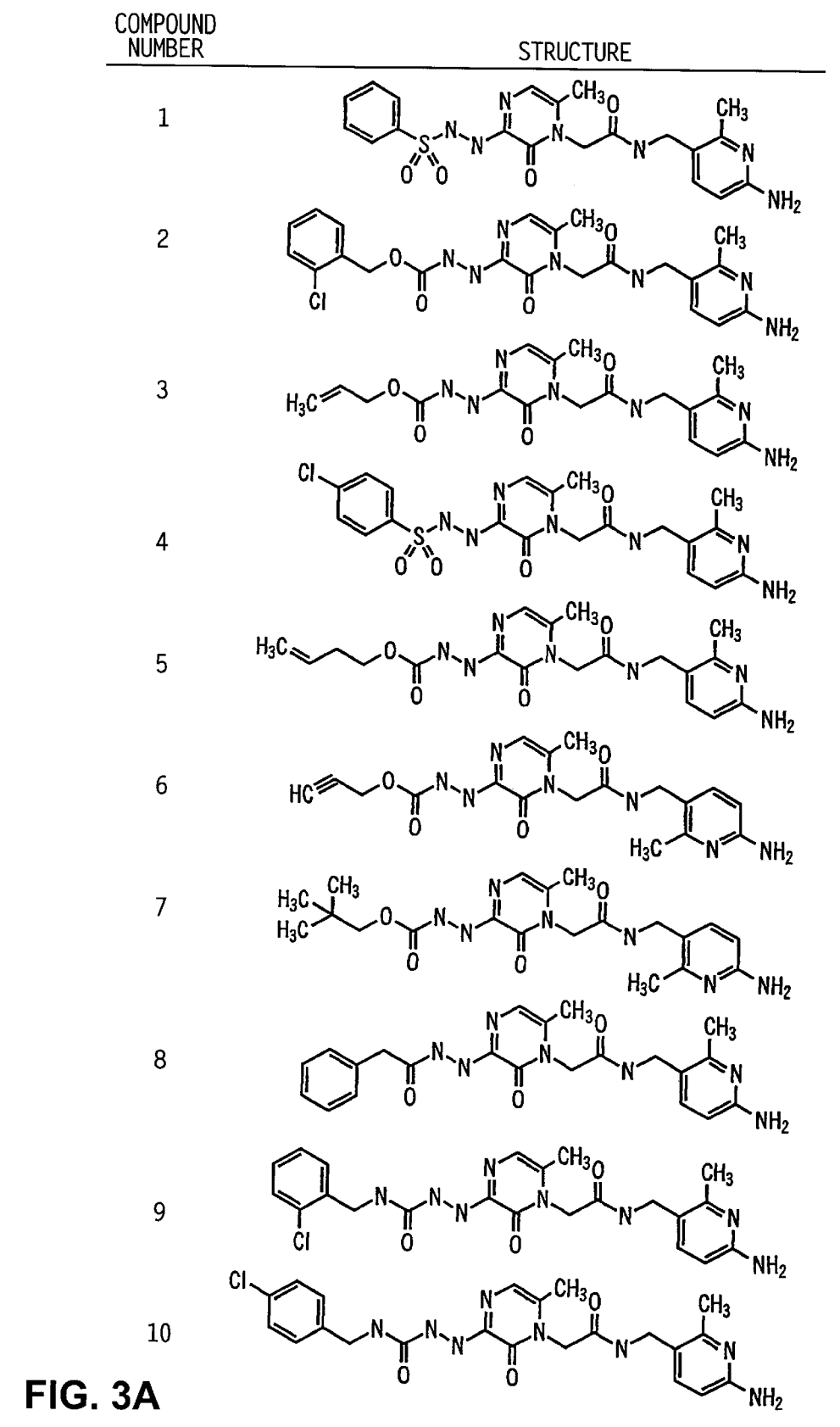
Figure 3B:
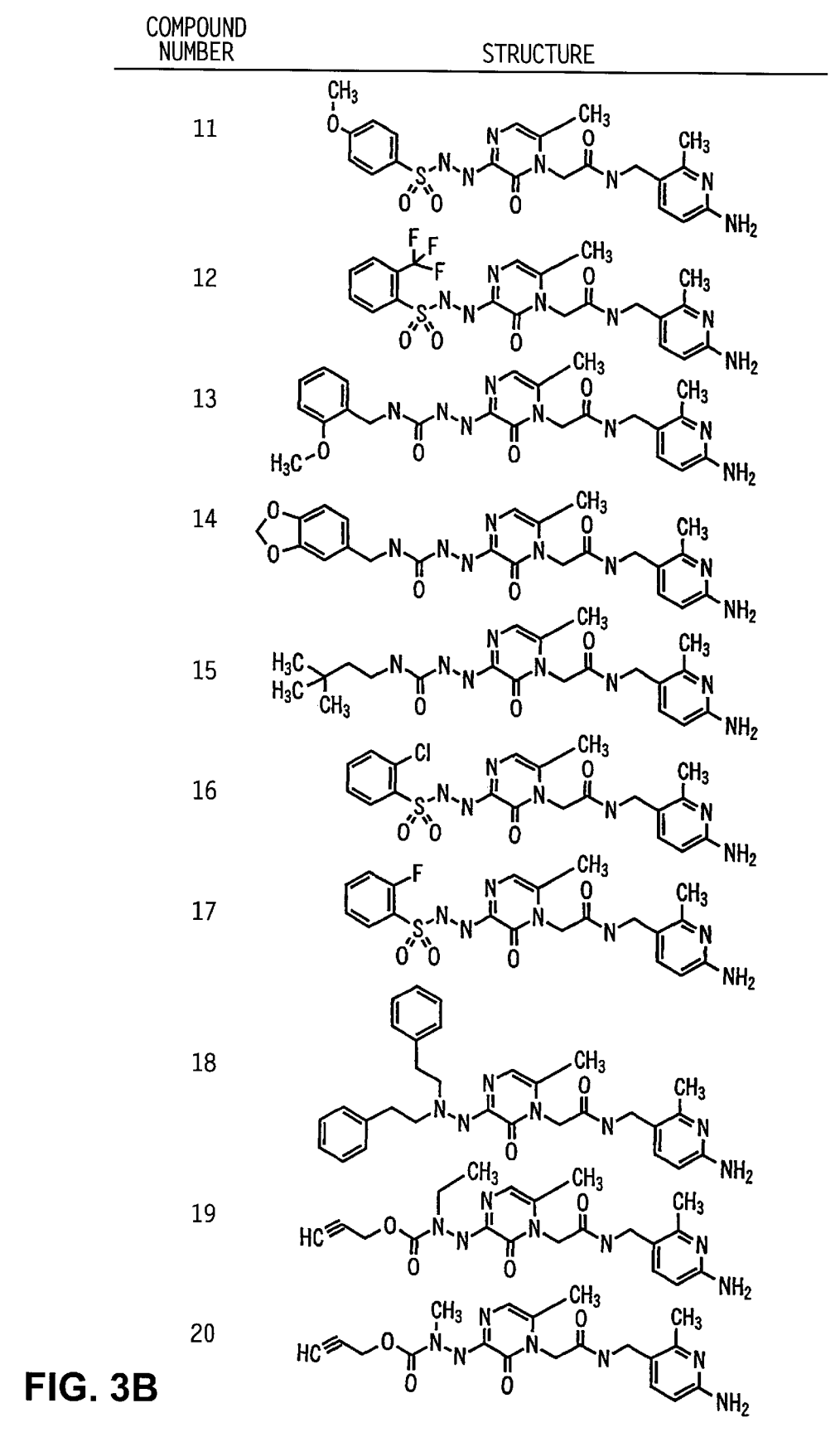

FIG. 3 depicts certain compounds having thrombin inhibitory activity.

FIG. 8 depicts a reaction scheme for the synthesis of an intermediate compound for preparing compounds having thrombin inhibitory activity. In this figure "i" through "vii" are defined as follows: i) NBS, benzoyl peroxide, CCl$_4$, reflux 6 hours; ii) NaN$_3$, DMF, room temperature 15 hours; iii) Ph$_3$P, THF, H$_2$O, 0° C., 0° C. to room temperature 15 hours, 0.25M HCl, neutralize with NaOH; iv) DCM, 1M Boc$_2$O in THF, room temperature 15 hours; v) t-BuOK, DMF, add 8-5, room temperature, 15 hours, then 65° C. 4 hours; vi) 2M HCl, methanal/dioxane, room temperature 4 hours; and vii) OH$^-$ resin, MeOH. These procedures are more fully described in Examples 81 to 86.

FIG. 9 depicts a reaction scheme for the synthesis of an intermediate compound for preparing compounds having thrombin inhibitory activity. In this figure, "i" through "vii" are defined as follows: i) NBS, benzoyl peroxide, CCl$_4$, reflux 6 hours; ii) NaN$_3$, DMF, room temperature 15 hours; iii) Ph$_3$P, THF, H$_2$O, room temperature, 15 hours; iv) DCM, 1M Boc₂O in THF, room temperature 15 hours; v) hydrazine, n-butanol, reflux 4 hours; vi) 2M HCl methanol/dioxane, room temperature 3 hours; and vii) OH⁻ resin, MeOH. These procedures are more fully described in Examples 87 to 91.

FIG. 12 depicts a reaction scheme for the synthesis of an intermediate for a compound having a 5-(aminomethyl) indazole at P1 which has thrombin inhibitory activity. In this figure, "i" through "viii" are defined as follows: i) 10% Pd/C, H₂ (10 psi), ethanol, room temperature 1.5 hours; ii) KOAc, Ac₂O, CHCl₃, reflux 3 hours; iii) cool to room temperature, isoamylnitrite, 18-crown-6, reflux 28 hours; iv) room temperature, Ac₂O, room temperature, 12 hours; v) aqueous 48% HBr, room temperature, 16 hours; vi) DHP, THF, reflux 2 hours, room temperature, 12 hours; vii) NaN₃, DMF, 90° C. 30 minutes and viii) LiAlH₄, THF, 0° C. one hour. These procedures are more fully described in Examples 100 to 106.

FIG. 13 depicts a reaction scheme for the synthesis of an intermediate compound for preparing compounds having thrombin inhibitory activity. In this figure, "i" through "iii" are defined as follows: i) CuCN, DMF, reflux 20 hours; ii) DMAP, Boc₂O, THF, room temperature 2 hours; and iii) 10% Pd/C, 1M HCl, ethanol, H₂ (50 psi), 16 hours. These procedures are more fully described in Examples 106 to 108.

DETAILED DESCRIPTION OF THE INVENTION

1. Preferred Compounds

Figure 1:
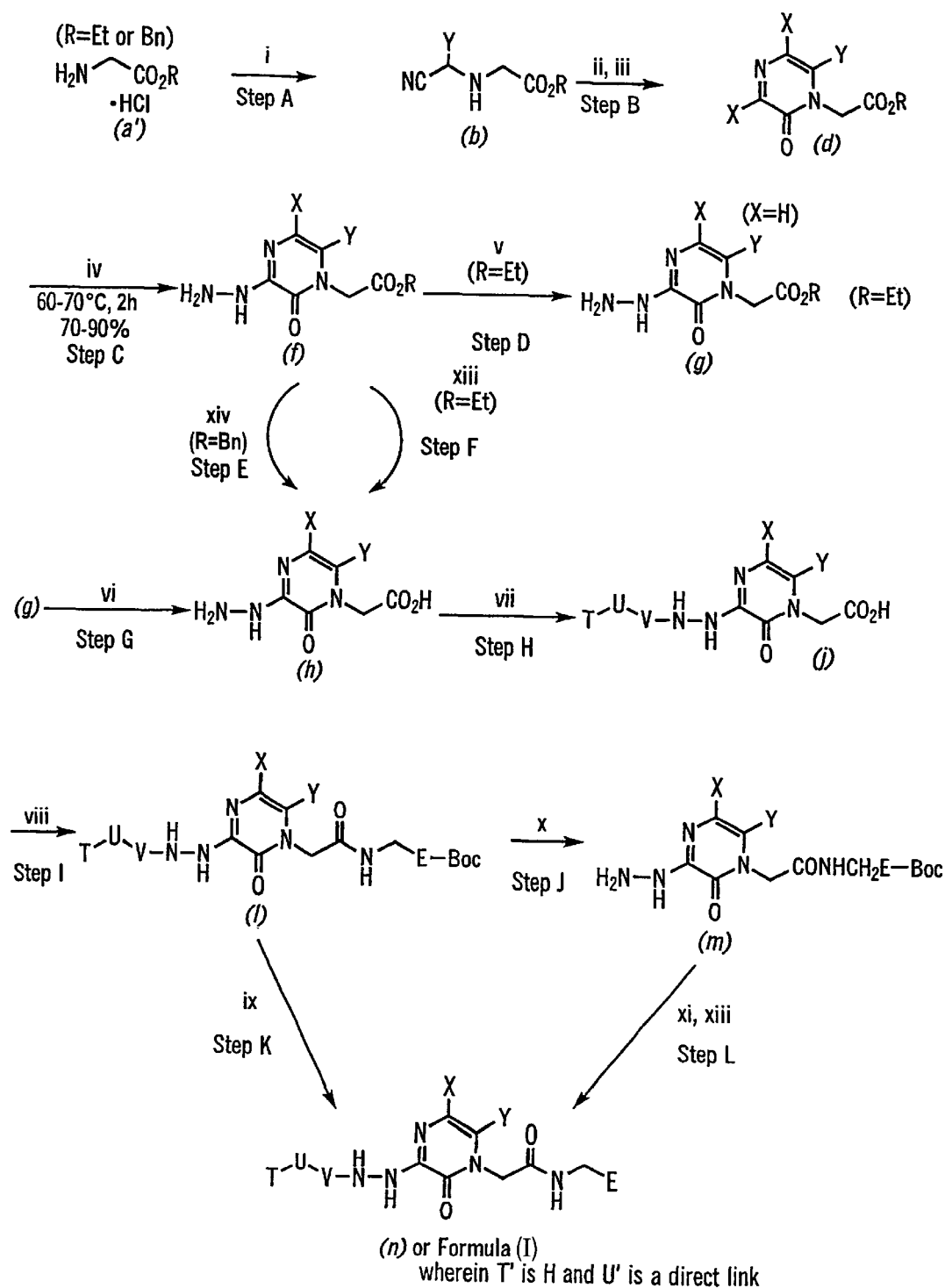
FIG. 1 depicts a reaction scheme for the synthesis of certain compounds having thrombin inhibitory activity. In this figure T, U, V and E are as defined in connection with formula (I) unless otherwise noted, X is Cl or H (as noted), Y is H or CH$_3$, R is ethyl or benzyl (as noted), T' is hydrogen, U' is a direct link, and E has an amino group. In this figure "i" through "xiv" are defined as follows: i) TMSiCN, YCHO (compound a), Et$_3$N, DCM, stirring at room temperature, 18 hours, 87% yield of compound b; ii) oxalylchloride ((COX)$_2$ where X is Cl) (compound c), 1,2-dichlorobenzene, 100° C. to 110° C., 18 hours; iii) quenching excess oxalylchloride with silica gel, 82% yield of compound d; iv) hydrazine (compound e), dioxane, 60 to 70° C., 2 hours, 70 to 90% yield of compound f; v) (R=ethyl) HCO$_2$NH$_4$, Pd/C, MeOH, reflux for 1 hour; vi) 6 M HCl, 60 to 70° C., 2 hours; vii) T—U—V—Cl (T=phenyl, U=CH$_2$, V=—OC(O)—) (compound i), NaHCO$_3$, dioxane, water, room temperature, 4 to 18 hours; viii) NH$_2$CH$_2$E—BOC (compound k), EDC, HOAt, NMM, DMF, room temperature, 18 to 20 hours; ix) TFA, DCM, room temperature, 1 hour; x) 1M HCl, Pd/C, MeOH, H$_2$ at 1 atm, 30 minutes to 1 hour; xi) T—U—V—Cl (T=phenyl, U=CH$_2$, V=—S(O)$_2$—) (compound i) (or T—U—N=C=O (compound i')), Et$_3$N, THF, room temperature, 1 hour; xii) TFA, DCM, room temperature, 1 hour; xiii) 6M HCl, 60 to 70° C., 2 hours; and xiv) (R=benzyl) HCO$_2$NH$_4$, Pd/C, MeOH, reflux, 1 hour.

According to one aspect, the present invention is directed to compounds of the formula:

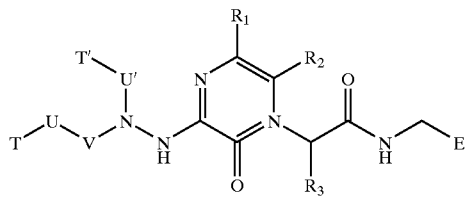

wherein:

(a) V is selected from the group consisting of —O—C(=O)—, —C(=O)—NH—C(=O)—, —NH—C(=O)—, —C(=O)—, —O—C(=S)—, —NH—S(O)₂—, —S(O)₂—, and a direct link;

(b) U and U' are independently selected from the group consisting of $C_{1-3}$ alkylene, $C_{1-3}$ alkylene substituted with $C_{1-3}$ alkyl and a direct link;

(c) T and T' are independently selected from the group consisting of
(1) $C_{1-6}$ alkyl, $C_{2-6}$ alkenyl, $C_{2-6}$ alkynyl,
(2) $C_{1-6}$haloalkyl, $C_{3-6}$haloalkenyl, $C_{3-6}$haloalkynyl;
(3) $C_{2-6}$oxaalkyl, $C_{3-6}$oxaalkenyl, $C_{3-6}$oxaalkynyl;
(4) $C_{1-6}$hydroxyalkyl, $C_{3-6}$hydroxyalkenyl, $C_{3-6}$hydroxyalkynyl;
(5) $C_{1-6}$carboxyalkyl, $C_{2-6}$carboxyalkenyl, $C_{2-6}$carboxyalkynyl;
(6) —$C_{1-3}$alkyl-carbonyl-$C_{1-3}$alkyl, —$C_{2-4}$alkenyl-carbonyl-$C_{2-4}$alkenyl, —$C_{2-4}$alkynyl-carbonyl-$C_{2-4}$ alkynyl;
(7) $C_{1-6}$nitroalkyl, $C_{2-6}$nitroalkenyl, $C_{2-6}$nitroalkynyl;
(8) $C_{1-6}$alkylamine, $C_{2-6}$alkenylamine, $C_{2-6}$alkynylamine;
(9) $C_{1-6}$alkylimine, $C_{2-6}$alkenylimine, $C_{2-6}$alkynylimine;
(10) $C_{1-6}$alkylamide, $C_{2-6}$alkenylamide, $C_{2-6}$alkynylamide;
(11) $C_{1-6}$alkylcarbamoyl, $C_{2-6}$alkenylcarbamoyl, $C_{2-6}$alkynylcarbamoyl;
(12) $C_{1-6}$alkylurea; $C_{2-6}$alkenylurea; $C_{2-6}$alkynylurea;
(13) $C_{1-6}$alkylhydrazine, $C_{2-6}$alkenylhydrazine, $C_{2-6}$alkynylhydrazine;
(14) $C_{1-6}$alkylnitrile, $C_{2-6}$alkenylnitrile, $C_{2-6}$alkynylnitrile;
(15) $C_{1-6}$alkylazide, $C_{2-6}$alkenylazide, $C_{2-6}$alkynylazide;
(16) $C_{1-6}$thioalkyl, $C_{3-6}$thioalkenyl, $C_{3-6}$thioalkynyl;
(17) $C_{1-6}$alkylthiol, $C_{2-6}$alkenylthiol, $C_{3-6}$alkynylthiol;
(18) $C_{3-6}$alkylisothiol, $C_{3-6}$alkenylisothiol, $C_{4-6}$alkynylisothiol;
(19) —$C_{1-6}$alkyl-thionyl-$C_{1-6}$alkyl, —$C_{2-6}$alkenyl-thionyl-$C_{2-6}$alkenyl, —$C_{2-6}$alkynyl-thionyl-$C_{2-6}$ alkynyl;
(20) —$C_{1-6}$alkyl-sulphuryl-$C_{1-6}$alkyl, —$C_{2-6}$alkenyl-sulphuryl-$C_{2-6}$alkenyl, —$C_{2-6}$alkynyl-sulphuryl-$C_{2-6}$ alkynyl;
(21) $C_{1-6}$alkylsulphonyl, $C_{2-6}$alkenylsulphonyl, $C_{2-6}$alkynylsulphonyl;
(22) $C_{1-6}$alkylsulphonamide, $C_{2-6}$alkenylsulphonamide, $C_{2-6}$alkynylsulphonamide;

(23) $C_{3-7}$cycloalkyl, halo-$C_{3-7}$cycloalkyl, $C_{3-7}$cycloalkyl-$C_{1-6}$alkyl, $C_{3-7}$cycloalkyl-di($C_{1-6}$alkyl), $C_{3-7}$cycloalkyl-$C_{3-6}$alkenyl, —$C_{3-7}$cycloalkyl-$C_{3-6}$alkynyl;

(24) heterocycloalkyl of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$ and/or $Y_3$; p2 (25) heterocyclo of 4 to about 10 ring atoms with the ring atoms selected from carbon and heteroatoms, wherein the heteroatoms are selected from the group consisting of oxygen, nitrogen, and $S(O)_i$, including

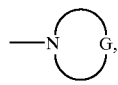

wherein

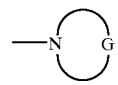

is a 5 to 7 member heterocycle of 3 to 6 ring carbon atoms, where G is —$CH_2$—, —O—, —S(=O)—, —$S(O)_2$— or —S—, which is optionally mono-, di-, or tri-substituted on the ring carbons with $Y_1$, $Y_2$ and/or $Y_3$;

(26) aryl of about 6 to about 14 carbon atoms which is optionally mono-, di- or tri-substituted with $Y_1$, $Y_2$, and/or $Y_3$;

(27) heteroaryl of about 5 to about 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$ and/or $Y_3$;

(28) aralkyl of about 7 to about 15 carbon atoms which is optionally substituted on the alkyl chain with hydroxy or halogen and mono-, di-, or tri-substituted in the aryl ring with $Y_1$, $Y_2$, and/or $Y_3$;

(29) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$, and/or $Y_3$;

(30) aralkenyl of about 8 to about 16 carbon atoms which is optionally mono-, di-, or tri-substituted on the aryl ring with $Y_1$, $Y_2$, and/or $Y_3$;

(31) heteroaralkenyl of 5 to 14 ring atoms with the ring atoms selected from carbon and heteroatoms, wherein the heteroatoms are selected from oxygen, nitrogen, and sulfur, and which is optionally mono-, di- or tri-substituted on the ring with $Y_1$, $Y_2$, and/or $Y_3$;

(32) fused carbocyclic of about 5 to about 13 carbon atoms, optionally substituted with $Y_1$, $Y_2$ and/or $Y_3$;

(33) fused carbocyclic alkyl of about 6 to about 16 carbon atoms, optionally substituted with $Y_1$, $Y_2$ and/or $Y_3$; and

(34) hydrogen;

(d)
(1) each $Y_1$, $Y_2$, and $Y_3$ is independently selected from the group consisting of halogen, cyano, nitro, tetrazolyl optionally substituted with alkyl of 1 to about 6 carbon atoms, guanidino, amidino, methylamino, methylguanidino, —$CF_3$, —$CF_2CF_3$, —CH$(CF_3)_2$, —C(OH)$(CF_3)_2$, —$OCF_3$, —$OCF_2CF_3$, —$OCF_2H$, —OC(O)$NH_2$, —OC(O)$NHZ_1$, —OC(O)$NZ_1Z_2$, —NHC(O)$Z_1$, —NHC(O)$NH_2$, —NHC(O)$NHZ_1$, —NHC(O)$NZ_1Z_2$, —C(O)OH, —C(O)$OZ_1$, —C(O)$NH_2$, —C(O)$NZ_1Z_2$, —P(O)$_3H_2$, —P(O)$_3(Z_1)_2$, —S(O)$_3$H, —S(O)$_pZ_1$, —$Z_1$, —$OZ_1$, —OH, —$NH_2$, —$NHZ_1$, —$NZ_1Z_2$, N-morpholino, nitro, —C≡N, and —S(O)$_p(CF_2)_qCF_3$, wherein p is 0, 1 or 2, q is an integer from 0 to 5, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 5 to about 14 ring atoms having about 3 to about 9 carbon atoms, or (2) $Y_1$ and $Y_2$ are selected together to be —O[C($Z_3$)($Z_4$)]$_r$O— or —O[C($Z_3$)($Z_4$)]$_{r+1}$—, wherein r is an integer from 1 to 4 and $Z_3$ and $Z_4$ are independently selected from the group consisting of hydrogen, alkyl or 1 to about 12 carbon atoms, aryl of about 6 to about 14 carbon atoms, heteroaryl of about 5 to about 14 ring atoms having 1 to about 9 carbon atoms, aralkyl of about 7 to about 15 carbon atoms, and heteroaralkyl of about 5 to about 14 ring atoms having about 3 to about 9 carbon atoms;

(e) $R_1$ is selected from hydrogen, halogen, and methyl;
(f) $R_2$ is selected from hydrogen, $C_{1-4}$alkyl, $C_{3-7}$Cycloalkyl, and $CF_3$;
(g) $R_3$ is hydrogen or $C_{1-4}$ alkyl; and
(h) E is:

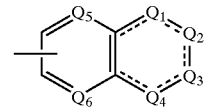

wherein
(1) $Q_1$ is $C(R_8)$, $C(R_9)(R_{9a})$, $N,N(R_{8a})$, or a direct link;
(2) $Q_2$ is $C(R_8)$, $C(R_{10})(R_{10a})$, $N,N(R_8)$, S, or O;
(3) $Q_3$ is $C(R_8)$, $C(R_{11})(R_{11a})$, N or $N(R_8a)$;
(4) $Q_4$ is $C(R_8)$, $C(R_{12})(R_{12a})$, $N,N(R_{8a})$, S, or O;
(5) $Q_5$ is $C(R_{13})$, $C(R_{13})(R_{13a})$ or N;
(6) $Q_6$ is $C(R_{14})$, $C(R_{14})(R_{14a})$ or N;
(7) $R_8$ is $NR_{15}R_{16}$ or —$OR_{15}$;
(8) $R_{8a}$ is hydrogen, alkyl of 1 to about 3 carbon atoms, $NR_{15a}R_{16a}$ or —$OR_{15a}$;
(9) $R_9$, $R_{10}$, $R_{11}$, $R_{12}$, $R_{13}$, and $R_{14}$ are independently selected from hydrogen, alkyl of 1 to about 3 carbon atoms substituted with alkoxy of 1 to about 3 carbon atoms, alkoxy of 1 to about 4 carbon atoms; halogen and trifluoromethyl;
(10) $R_{9a}$, $R_{10a}$, $R_{11a}$ $R_{12a}$, $R_{13a}$ and $R_{14a}$ are independently hydrogen or absent;
(11) $R_{15}$ and $R_{15a}$ are independently hydrogen, alkyl of 1 to about 3 carbon atoms, or —C(=O)$R_{17}$;
(12) $R_{16}$ and $R_{16a}$ are independently hydrogen or alkyl of 1 to about 3 carbon atoms;
(13) alternatively, $R_{15}$ and $R_{16}$ or $R_{15a}$ and $R_{16a}$ taken together form a divalent radical of the formula —(CH$_2$)$_w$—, where w is independently 3, 4 or 5; and

(14) $R_{17}$ is alkyl of 1 to about 6 carbon atoms or alkoxy of 1 to about 6 carbon atoms;

with the provisos that:

(i) no more than two of $Q_1$, $Q_2$, $Q_3$ and $Q_4$ can be $C(R_8)$ or $N(R_{8a})$;

(ii) at least one of $Q_1$, $Q_2$, $Q_3$ and $Q_4$, but not all, is N or $N(R_{8a})$;

(iii) only one of $Q_2$ and $Q_4$ can be O or S; and (iv) $Q_1$, $Q_2$, $Q_3$ and $Q_4$ are not all heteroatoms;

and pharmaceutically acceptable salts thereof.

For selection of T and T', suitable heterocycloalkyl, heterocyclo, heteroaryl, and heteroaralkyl groups include substituted or unsubstituted monovalent radicals of: furan, thiophene, thiazole, isothiazole, 2H-pyrrole, pyrrole, 2-pyrroline, 3-pyrroline, pyrrolidine, imidazole, 2-imidazoline, imidazolidine, 1,2,3-triazole, pyrazole, 2-pyrazoline, pyrazolidine, pyridine, piperidine, pyridazine, pyrimidine, pyrazine, piperazine, 1,3,5-triazine, 1,3-dioxolane, oxazole, isoxazole, 1,2,3-oxadiazole, 1,3,4-thiadiazole, 2H-pyran, 4H-pyran, 1,4-dioxane, morpholine, thiomorpholine, 1,4-dithiane, 1,2,5-trithiane, indolizine, indole, isoindole, 3H-indole, indoline, lH-indazole, benzimidazole, benzthiazole, purine, benzo[b]furan, benzo[b]thiophene, cinnoline, phthalazine, 4H-quinoline, quinoline, isoquinoline, quinazoline, quinoxaline, 1,8-naphthyridine, pteridine, carbazole, acridine, phenzaine, phenothiazine, and phenoxazine.

For T and T', suitable aryl and aralkyl groups include phenyl, substituted phenyl, benzyl, substituted benzyl, naphthalene, hydroxy$C_{1-3}$alkylnaphthalene and fluorene. Substituted phenyl groups include, for example, halophenyl, $C_{1-3}$alkylphenyl, halo-$C_{1-3}$alkylphenyl, $C_{3-4}$alkenylphenyl, $C_{1-3}$alkoxyphenyl, ($C_{1-3}$alkoxy)(monohalo)phenyl, ($C_{1-3}$alkyl)(monohalophenyl), ($C_{1-3}$ alkoxy)(nitro)phenyl, ($C_{1-3}$ alkyl)(nitro)phenyl, and (halo)(nitro)phenyl.

Preferred V groups include —O—C—(=O)—, —NH—C(=O), —C(=O), —S(O)$_2$— and a direct link. Especially preferred V groups include —O—C(=O)—, —NH—C(=O), —S(O)$_2$— and a direct link.

Preferred U groups include —CH$_2$—, —CH(CH$_3$)—, —CH$_2$CH$_2$, and a direct link. Especially preferred U groups include methylene, ethylene and a direct link.

Preferred U' groups include methylene, ethylene and a direct link.

When U is a direct link, preferred T groups include phenyl, substituted phenyl, benzyl, substituted benzyl, and alkyl. When U is methylene, preferred T groups include phenyl, substituted phenyl, alkenyl, alkyl, cycloalkyl and alkynyl. When U is ethylene, preferred T groups include phenyl and substituted phenyl.

When U' is a direct link, preferred T' groups include hydrogen. When U' is methylene, preferred T' groups include hydrogen. When U' is ethylene, preferred T' groups include hydrogen, phenyl and substituted phenyl.

Preferred E groups include those wherein $Q_1$ is a direct link. Preferably (a) $Q_2$ is $C(R_8)$ or $C(R_{10})(R_{10a})$, $Q_3$ is N and $Q_4$ is N; (b) $Q_2$ is $C(R_8)$ or $C(R_{10})(R_{10a})$, $Q_3$ is $C(R_{11})(R_{11a})$ and $Q_4$ is N; (C) $Q_2$ is 0, $Q_3$ is N and $Q_4$ is $C(R_8)$ ; (d) $Q_2$ is N, $Q_3$ is N and $Q_4$ is $C(R_8)$ or (e) $Q_2$ is N, $Q_3$ is $C(R_8)$ or $C(R_{11})(R_{11a})$ and $Q_4$ is N. Especially preferred E groups include those where $Q_6$ is $C(R_{14})$ or $C(R_{14})$ ($R_{14a}$).

Preferred $R_1$ groups include hydrogen and chloro; more preferably $R_1$ is hydrogen.

Preferred $R_2$ groups include methyl.

Preferred $R_3$ groups include hydrogen.

According to one preferred embodiment, provided are compounds wherein V is —S(O)$_2$—, —O—C(=O)—, —NHC(=O)— or —C(=O)—; U and U' are both direct links; T is phenyl, substituted phenyl, benzyl or substituted benzyl; T' is hydrogen; E is selected from

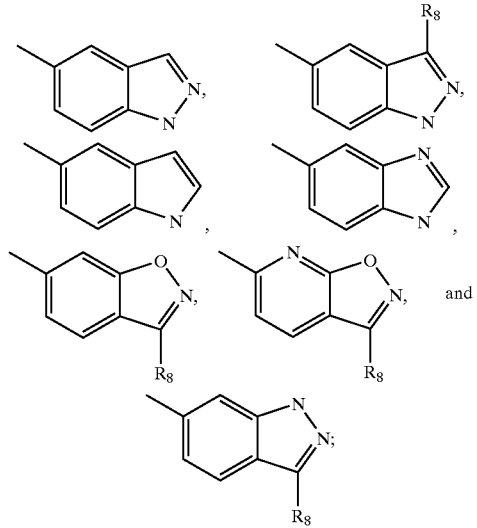

$R_1$ is hydrogen; $R_2$ is methyl; and $R_3$ is hydrogen. When T is substituted benzyl, preferred substituted benzyl groups include benzyl mono- or di-substituted with halogen, alkoxy, or trifluoromethyl or two substituents taken together are —O—CH$_2$CH$_2$O— to give piperonyl group. According to a preferred aspect of this embodiment, V is —S(O)$_2$— and T is preferably phenyl or substituted phenyl. According to this aspect, especially preferred T groups include phenyl mono-substituted with $X_1$ where $X_1$ is preferably alkoxy, trifluoromethyl or halogen, more preferably in the ortho or para position of the phenyl ring. According to an alternate preferred aspect of this embodiment, V is —O—C(=O)— or —NH—C(=O)— and T is preferably benzyl or substituted benzyl. According to this aspect, especially preferred T groups include benzyl optionally mono- or di-substituted with $X_1$ and/or $X_2$ where $X_1$ and $X_2$ are preferably halogen or alkoxy, or $X_1$ and $X_2$ selected together are —OCH$_2$CH$_2$— to give a piperonyl ring. Especially preferred E groups include

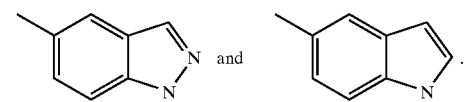

According to another preferred embodiment, provided are compounds wherein V is —O—C(=O)— or —NH—C(=O)—; U is methylene or ethylene; U' is a direct link, methylene or ethylene; T is alkyl, alkenyl or alkynyl; T' is hydrogen; E is selected from

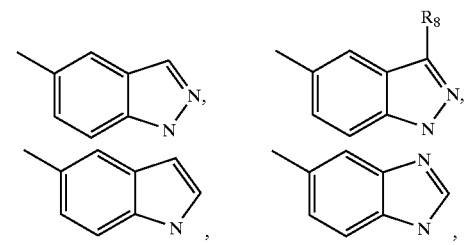

-continued

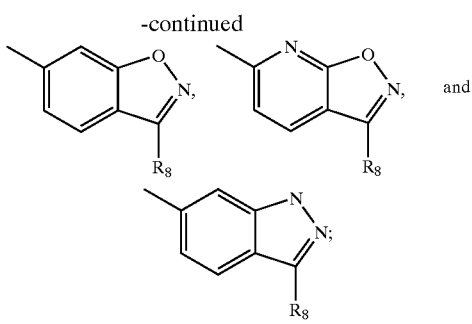

$R_1$ is hydrogen; $R_2$ is methyl; and $R_3$ is hydrogen. According to a preferred aspect of this embodiment, V is —O—C(=O)— and T is alkenyl or alkynyl, preferably having the double or triple bond (respectively) between the two terminal carbon atoms. According to an alternate preferred aspect of this embodiment, V is —O—C(=O)— or —NH—C(=O)— and T is alkyl group which includes tertiary butyl moiety. Such alkyl groups include, but are not limited to, tertiary butyl and 2-dimethylpropyl groups. Especially preferred E groups include

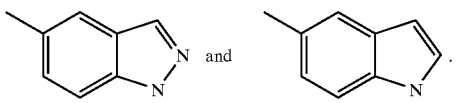

According to a further preferred embodiment, provided are compounds where V is a direct link, U and U' are alkylene, T and T' are phenyl or substituted phenyl; E is selected from

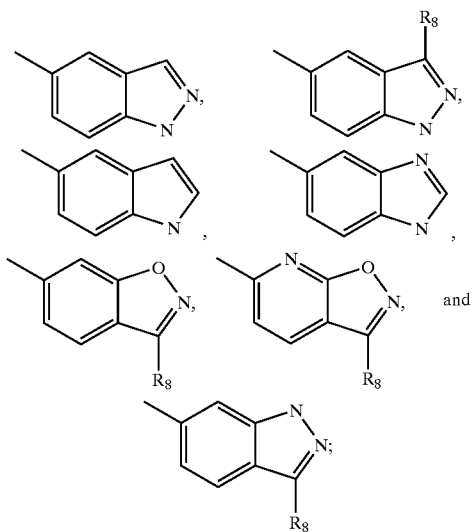

$R_1$ is hydrogen, $R_2$ is methyl, and $R_3$ is hydrogen.
Especially preferred E groups include

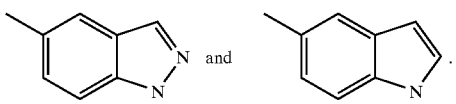

$R_1$ is hydrogen, $R_2$ is methyl, and $R_3$ is hydrogen.
Preferred compounds of the present invention include those depicted in FIGS. 17A to 17C. Especially preferred are those compounds depicted in FIG. 17C.

For any given variable having a value of 0, the bond attached to the variable is not present, for example, with the group —(R$^6$)$_n$, if n is 0, then the single bond that would attach to R$^6$ is also not present.

Description of compounds of the present invention are limited by principles of chemical bonding known to those skilled in the art.

The compounds of present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

2. Preparation of Preferred Compounds
   A. General Procedures

The symbols and conventions used in the processes, schemes and examples herein are consistent with the usage in the contemporary scientific literature: for example, the *Journal of the American Chemical Society* or the *Journal of Biological Chemistry*. Amino acid residues are designated by standard single-letter or three-letter abbreviations, and are assumed to be in the L-configuration unless otherwise noted. Unless otherwise noted, all starting materials were obtained from commercial suppliers and used without further purification. Specifically, the following abbreviations may be used in the examples and throughout the specification: g (grams); mg (milligrams); L (liters); mL (milliliters); μL (microliters); psi (pounds per square inch); M (molar); mmol (millimolar); i. v. (intravenous); Hz (Hertz); MHz (megahertz); mol (moles); mmol (millimoles); eq (equivalents); RT (room temperature); min (minutes); h (hours); mp (melting point); TLC (thin layer chromatography); HPLC (high pressure liquid chromatography); R$_t$ (retention time); RP (reverse phase); and atm (atmosphere). All references to ether are to diethyl ether; brine refers to a saturated aqueous solution of NaCl. Unless otherwise indicated, all temperatures are expressed in °C. (degrees Celsius). All reactions were conducted under an inert atmosphere at room temperature unless otherwise noted.

$^1$H NMR spectra were recorded on a Varian Unity-400 spectrometer. Chemical shifts are expressed in parts per million (ppm) relative to TMS (δ). Coupling constants are in hertz (Hz). The apparent multiplicities of the peaks are designated as s (singlet), d (doublet), t (triplet), q (quartet), m (multiplet), and br (broad).

Low-resolution mass spectra (MS) were recorded on a Perkin Elmer SCIE API1 spectrometer. All reactions were monitored by thin-layer chromatography on 0.25 mm E. Merck silica gel plates (60F-254), and visualized with UV light or 5% ethanolic phosphomolybdic acid. Silica gel for flash column chromatography was 230–400 mesh (Merck).

B. Description of Compound Syntheses

In the following schemes and examples, protecting groups for sensitive or reactive groups are employed where necessary in accordance with generally understood principles of chemistry. Protecting groups are manipulated according to standard methods of organic synthesis (T. W. Green and P. G. M. Wuts, *Protecting Groups in Organic Synthesis*, John Wiley & Sons, 1991). These groups are removed at convenient stages of the compound's synthesis using methods that are readily apparent to those skilled in the art.

Those skilled in the art will recognize that when compounds of formula I contain one or more stereocenters, single stereoisomers (enantiomers or diastereomers) can be synthesized by stereospecific synthesis, or resolution of the final product or any convenient intermediate. Any suitable method known in the art may be used to resolve a final product, intermediate, or starting material. See, for example, *Stereochemistry of Organic Compounds*, E. L. Eliel, S. H. Wilen, and L. N. Mander (Wiley-Interscience, 1994).

C. Syntheses of Pyrazinone Hydrazine Derivatives (i) FIG. 1

Certain compounds can be prepared according to the synthetic sequence shown in FIG. 1. In FIG. 1, T, U, V, and E are as defined, unless otherwise noted, for Formula (I), and R is Et or Bn, and X is halogen or H (where indicated), Y is $CH_3$, T' is hydrogen, U' is a direct link and E has an amino group ($R_8$ is amino). Thus, unless otherwise specified, the variable groups of the compounds in FIG. 1 correspond to those defined in connection with Formula (I). In step A, an appropriate ester of glycine (a'), is condensed with a suitable aldehyde, YCHO, (a) and trimethylsilyl cyanide to provide the aminonitrile (b). In step B, product (b) is reacted with an appropriate oxalyl halide, $(COX)_2$ (c) in 1,2-dichlorobenzene at 100° C. to give the pyrazinone (d). In step C, the substituent at the 3-position (X) is displaced by the appropriate amine derivative, $NH_2$—$NH_2$ (e) under reaction conditions which include dioxane, and 60 to 70° C. for 2 hours to yield (f).

Catalytic transfer hydrogenation of (f) (R=Et) in step D using ammonium formate and palladium on carbon in refluxing methanol affords the reduced derivative (g). The resulting alkyl ester is hydrolyzed in step G using HCl (6M) at 60° C. The corresponding 5-halo derivative (h) is synthesized by acid hydrolysis of intermediate (f) as described in step F. Catalytic transfer hydrogenation of (f) where R=Bn directly provides reduced acid (h) as described in step E. The resulting amino acid is condensed in step H with an appropriate group T—U—V—Cl, (i) or, T—U—N=C=O (i') (where T is phenyl, Cl is $CH_2$ and V is —OC(=O)—) affording (j). In Step I, acid (j) is coupled with the appropriate amine using EDC and HOAt in a suitable solvent (e.g. DMF) affording (1). Acid deprotection in Step K affords the desired product (n).

Where (i) is benzyl chloroformate, intermediate (1) may be hydrogenated as reported in step J to afford free hydrazine (m). Condensation with a suitable group ((i) or (i')) followed by acid work-up affords final product (n) as described in step L.

Figure 2:
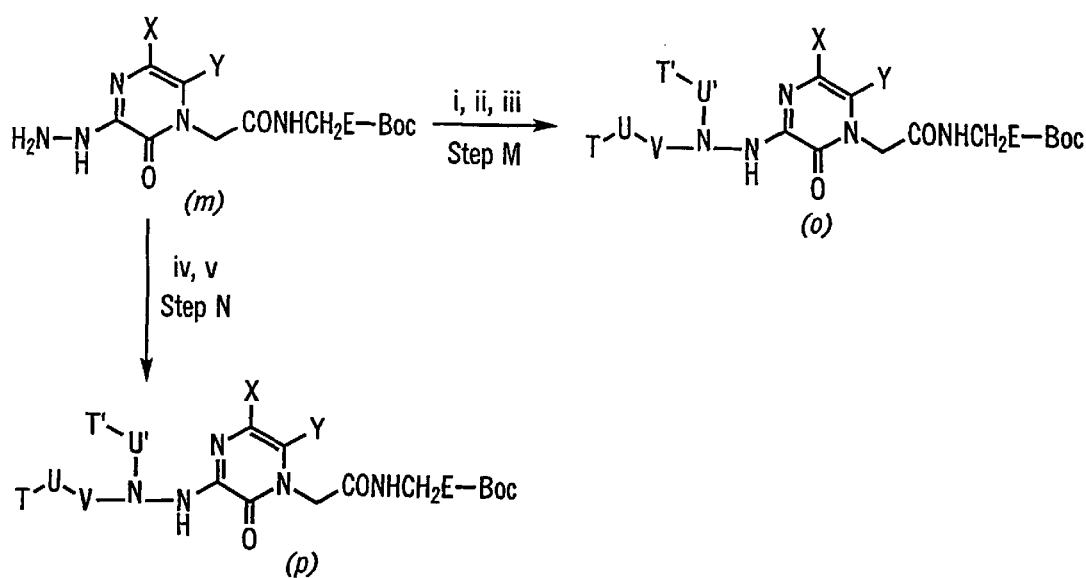
FIG. 2 depicts a reaction scheme for the synthesis of certain compounds having thrombin inhibitory activity. In this figure, T, T', U, V and E are as defined in connection with formula I unless otherwise noted; U" is C$_{1-2}$ alkyl-L, C$_{1-2}$ alkylene substituted with C$_{1-3}$ alkyl-L or a direct link; L is —CHO or —CO—C$_{1-3}$ alkyl; X is R$_1$, Y is R$_2$ and E has an amino group. In this figure "i" through "v" are defined as follows: i) T'—U"—L, NaCNBH$_3$ or NaBH(OAc)$_3$, MeOH or DCE; ii) compound i (T—U—V—Cl) or compound i' (T—U—N=C=O), Et$_3$N, THF, room temperature, 2 to 18 hours; iii) TFA, DCM, room temperature, 1 hour; iv) T—U"—L, NaCNBH$_3$ or NaBH(OA$_c$)$_3$, MeOH or DCE, room temperature, 1 hour; and v) TFA, DCM, room temperature, 1 hour.
Figure 4:
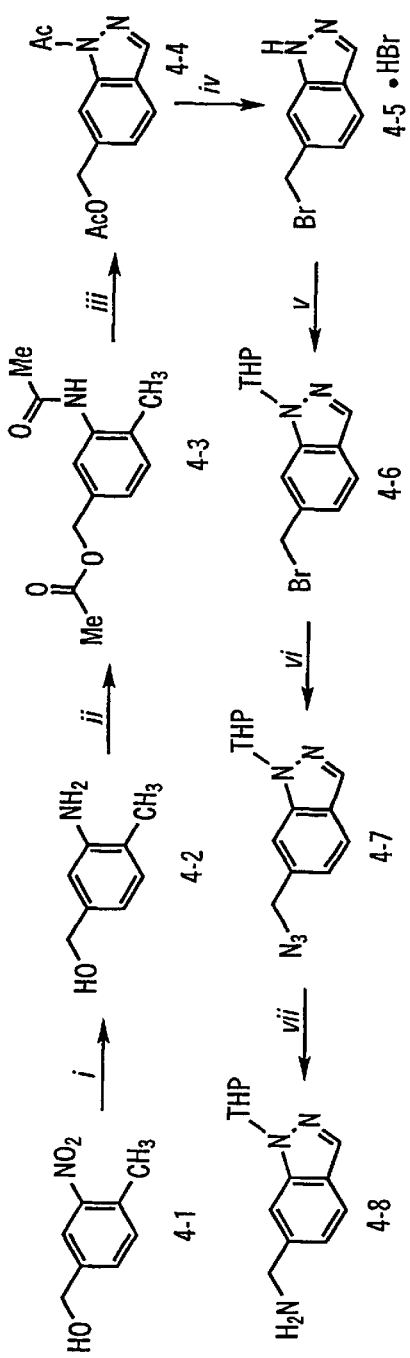
FIG. 4 depicts a reaction scheme for the synthesis of an intermediate compound for preparing compounds having thrombin inhibitory activity. In this figure "i" through "vii" are defined as follows: i) H$_2$ 1 Atm, 10% Pd/C, EtOAc, room temperature 48 hours, 51% yield; ii) Ac$_2$O, KOAc, CHCl$_3$, reflux 2 hours, 92% yield; iii) isoamylnitrite, KOAc, catalytic amount 18-crown-6, Ac$_2$O, CHCl$_{13}$, reflux 28 hours, 95% yield; iv) aqueous 48% HBr, room temperature 46 hours, 84% yield; v) DHP, THF, reflux 2 hours, 72% yield; vi) NaN$_3$, DMF, 90° C. 0.5 hour, 83% yield; and vii) LiAlH$_4$, THF, 0° C. 1 hour. These procedures are more fully described in Examples 61 to 67.
Figure 5:
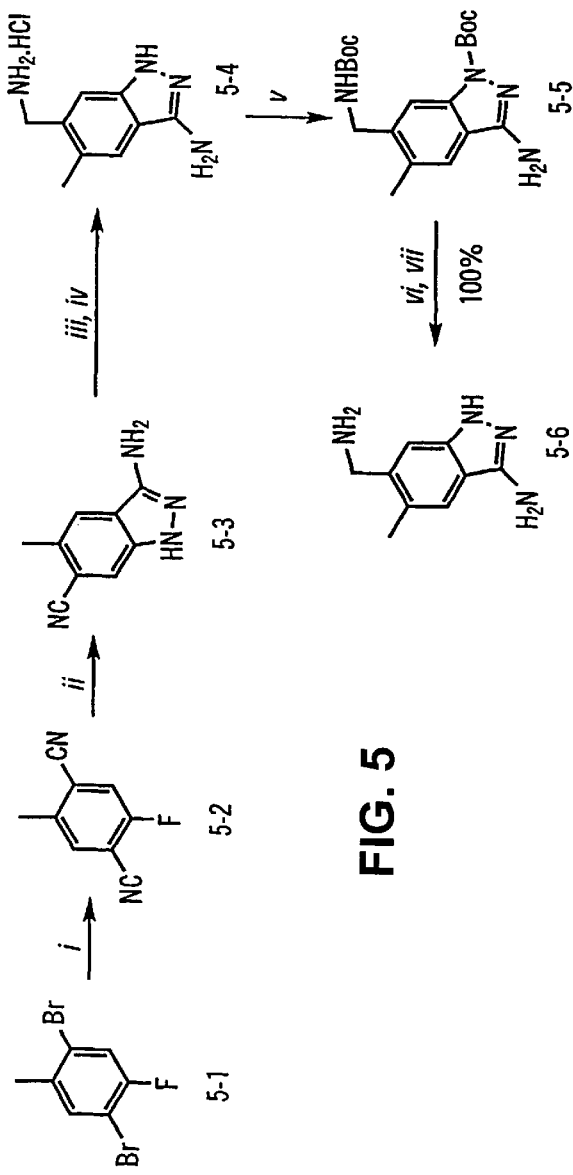
FIG. 5 depicts a reaction scheme for the synthesis of an intermediate compound for preparing compounds having thrombin inhibitory activity. In this figure "i" through "vii" are defined as follows: i) CuCN, DMF, reflux 6 hours, 76% yield; ii) NH$_2$NH$_2$, ethanol, reflux, N$_2$, 17 hours, 91% yield; iii) BH$_3$.THF, 0° C. to room temperature, 15 hours; iv) 6N HCl, water and methanol, room temperature, 6 hours; v) Boc$_2$O in THF, THF/methanol, room temperature, 15 hours, 60% yield; vi) 2N HCl, methanol/dioxane, room temperature 4 hours; and vii) OH$^-$ resin, MeOH. These procedures are more fully described in Examples 68 to 71.
Figure 6:
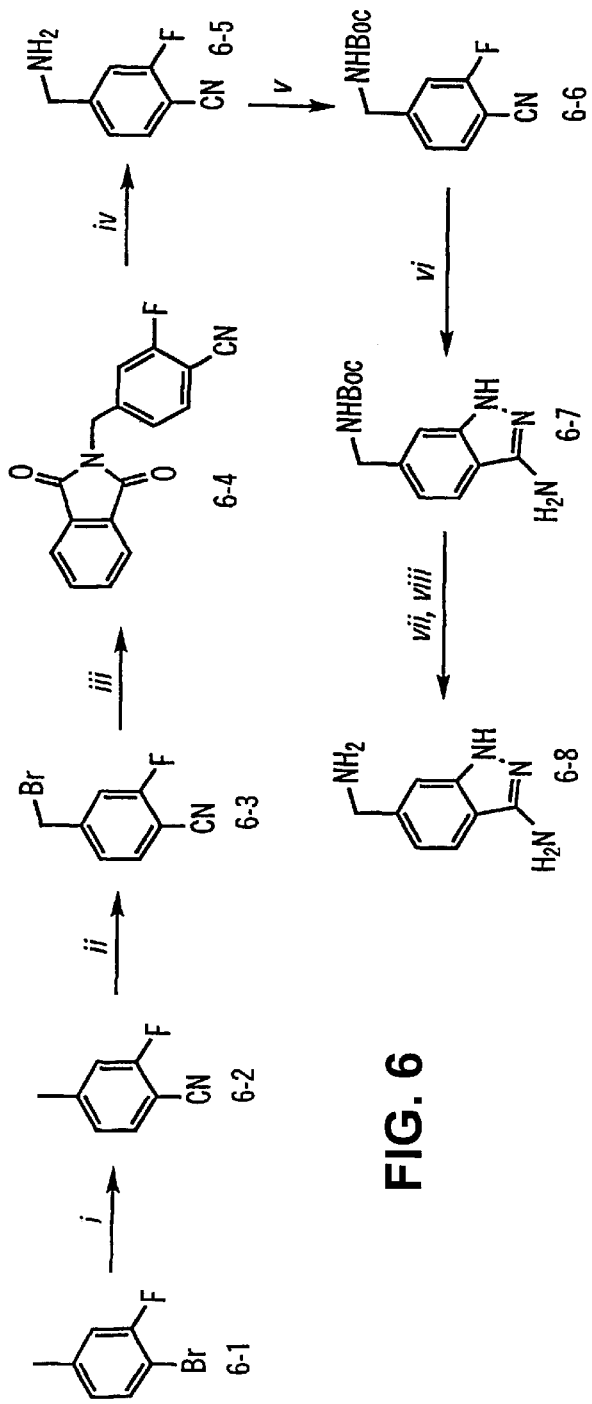
FIG. 6 depicts reaction schemes for the synthesis of an intermediate compound for preparing compounds having thrombin inhibitory activity. In this figure, "i" through "viii" are defined as follows: i) CuCN, DMF, reflux 5 hours; ii) NBS, AIBN, CCl$_4$, reflux 4.5 hours; iii) phthalimide, CS$_2$CO$_3$, DMF, room temperature 0.5 hour; iv) hydrazine, n-butanol, reflux 5 minutes; v) Boc$_2$O, DCM, room temperature 1 hour; vi) hydrazine, n-butanol, reflux 22 hours; vii) 2M HCl in dioxane, room temperature 0.5 hour; and viii) OH$^-$ resin, MeOH. These procedures are more fully described in Examples 72 to 77.
Figure 7:
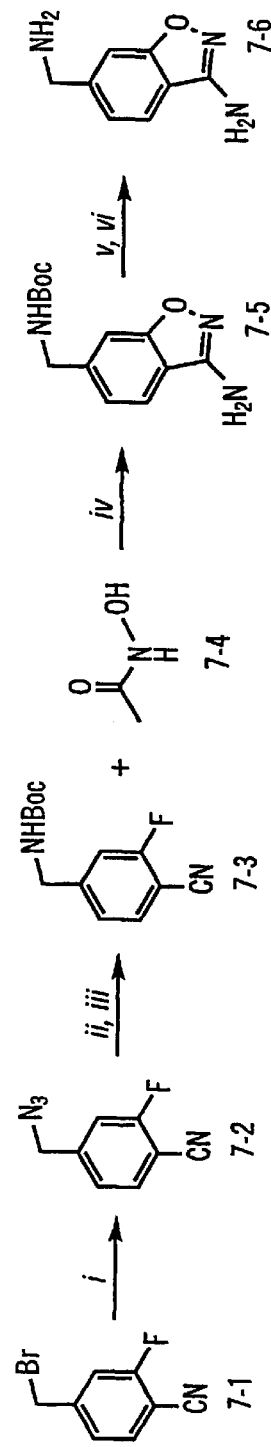
FIG. 7 depicts a reaction scheme for the synthesis of an intermediate compound for preparing compounds having thrombin inhibitory activity. In this figure "i" through "vi" are defined as follows: i) NaN$_3$, DMF, room temperature, 15 hours; ii) Ph$_3$P, THF/H$_2$O, room temperature, 15 hours; iii) Boc$_2$O in DMF, room temperature, 18 hours; iv) t-BuOK, DMF, add 7-3, room temperature, 15 hours, then 70° C., 24 hours; v) 2N HCl, methanol/dioxane, room temperature 0.5 hour; and vi) OH$^-$ resin, MeOH. These procedures are more fully described in Examples 78 to 80.
Figure 10:
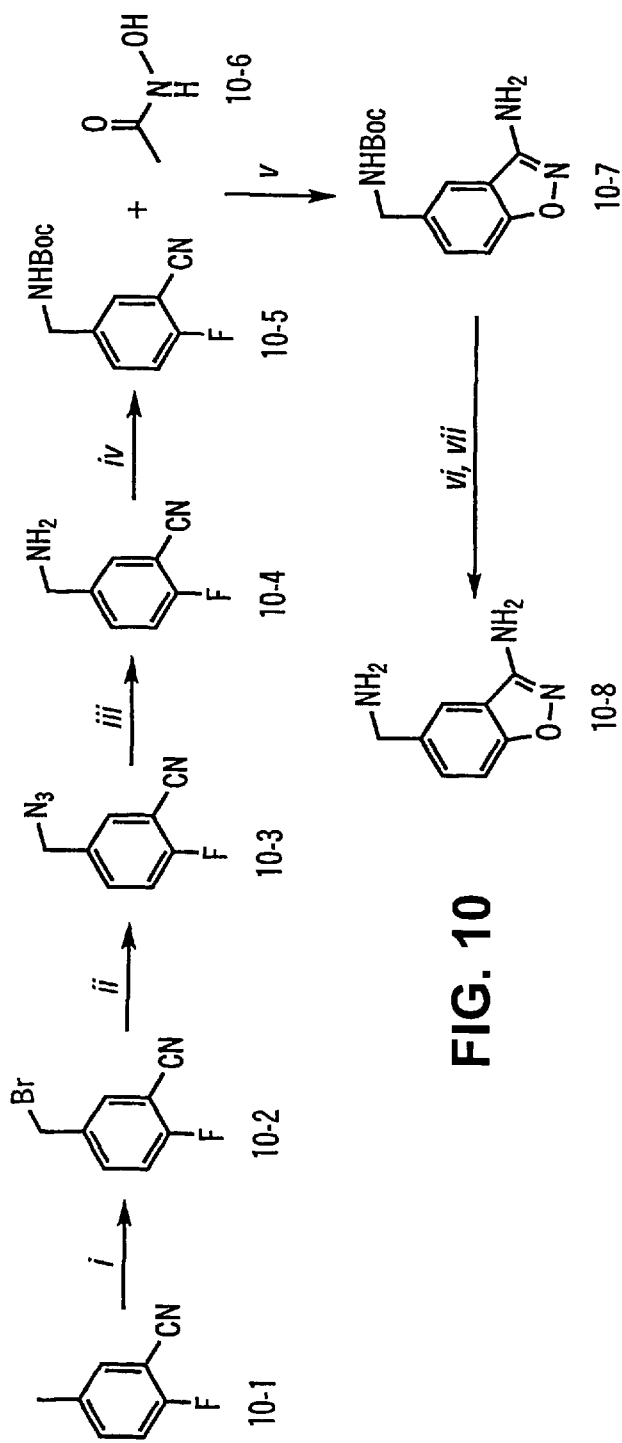
FIG. 10 depicts a reaction scheme for the synthesis of an intermediate for preparing compounds having thrombin inhibitory activity. In this figure, "i" through "vii" are defined as: i) NBS, AIBN, CCl₄, reflux 8 hours; ii) NaN₃, DMF, room temperature 15 hours; iii) Ph₃P, THF, H₂O, room temperature, 15 hours; iv) Boc₂O, DCM, room temperature 2 hours; v) t-BuOK, DMF, room temperature 15 hours; vi) 2N HCl, methanol/dioxane, room temperature 5 hours; and vii) OH⁻ resin, MeOH. These procedures are described more fully in Examples 92 to 97.
Figure 11:
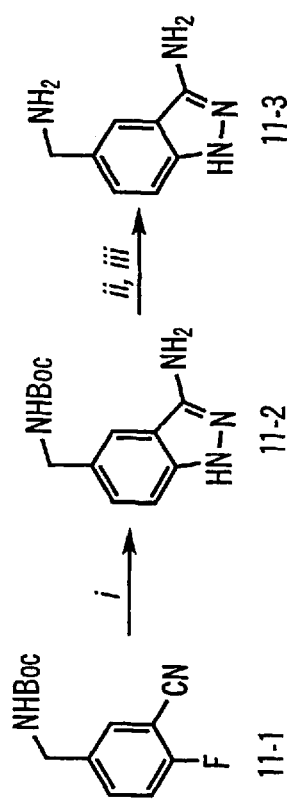
FIG. 11 depicts a reaction scheme for the preparation of an intermediate compound for preparing compounds having thrombin inhibitory activity. In this figure, "i" through "iii" are defined as follows: i) hydrazine, n-butanol, reflux 22 hours; ii) 2M HCl in dioxane, room temperature 3 hours; and iii) OH⁻ resin, MeOH. These procedures are more fully described in Examples 98 to 99.
Figures 14, 15, 16:
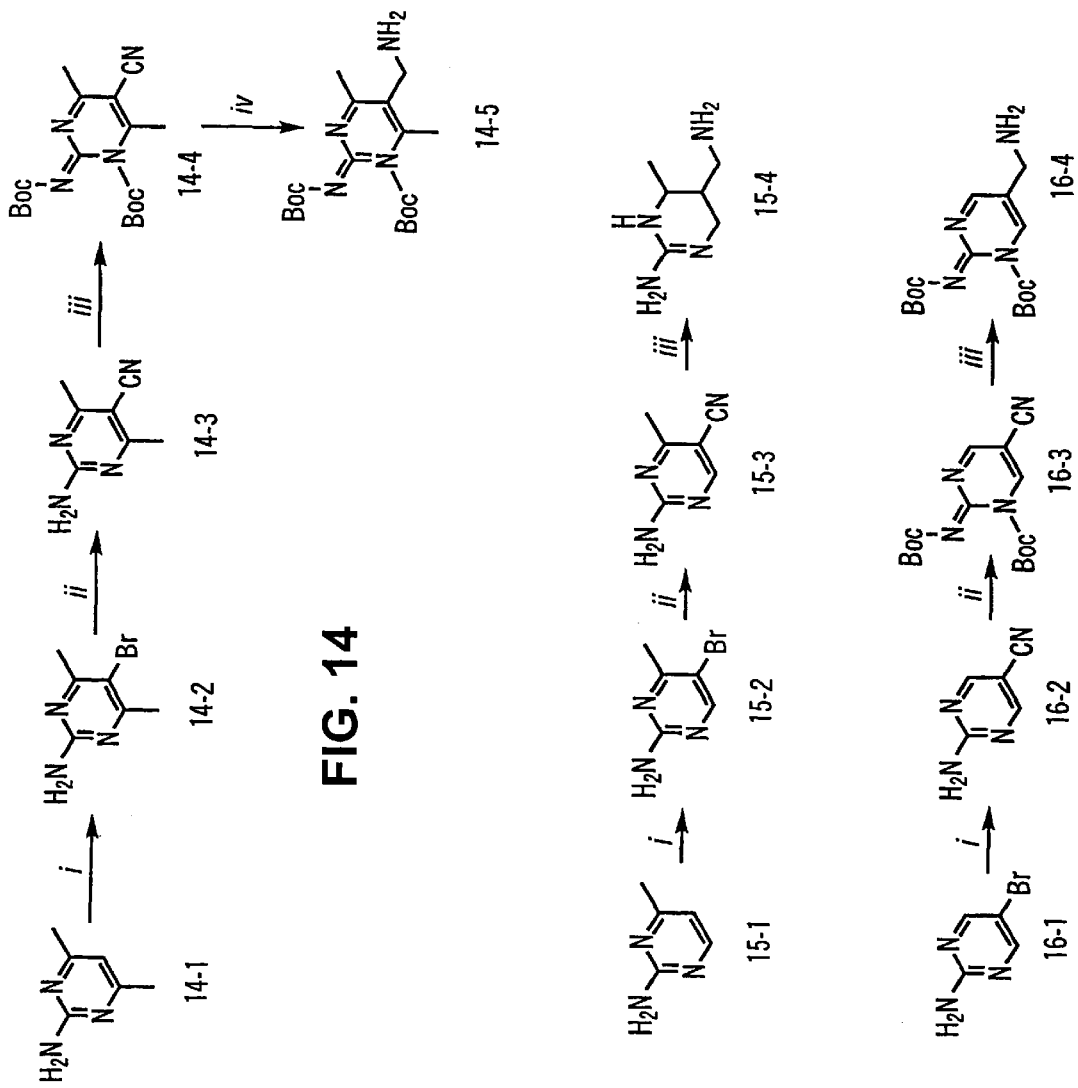
FIG. 14 depicts a reaction scheme for the synthesis of an intermediate compound for preparing compounds having thrombin inhibitory activity. In this figure, "i" through "iv" are defined as follows: i) HOAc, Br₂, 0° C., 30 minutes; ii) CuCN, DMF, reflux 20 hours; iii) Boc₂O, DMAP, THF, room temperature 2 hours; and iv) 10% Pd/C, 1M HCl, EtOH, H₂(45 psi), 16 hours. These procedures are more fully described in Examples 109 to 112.
FIG. 15 depicts a reaction scheme for the synthesis of an intermediate compound for preparing compounds having thrombin inhibitory activity. In this figure, "i" through "iii" are defined as follows: i) NaHCO₃, water, Br₂, 65° C., 1.5 hours; ii) CuCN, DMF, 185° C. reflux 20 hours; and iii) 10% Pd/C, 1M HCl (aq), EtOH, THF, H₂(20 psi), 16 hours. These procedures are more fully described in Examples 113 to 115.
FIG. 16 depicts a reaction scheme for the synthesis of an intermediate compound for preparing compounds having thrombin inhibitory activity. In this figure, "i" through "iii" are defined as follows: i) CuCN, DMF, reflux 20 hours; ii) Boc₂O, DMAP, THF, room temperature, 2 hours; and iii) 10% Pd/C, 1M HCl (aq), EtOH, H₂(50 psi), room temperature 16 hours. These procedures are more fully described in Examples 116 to 118.

(ii) FIG. 2

Disubstituted hydrazines can be obtained as shown in FIG. 2. In this figure, T, T', U, V and E are as defined in connection with formula (I) unless otherwise noted; U" is $C_{1-2}$ alkyl-L, $C_{1-2}$ alkylene substituted with $C_{1-3}$ alkyl-L or a direct link, L is —CHO or —CO—$C_{1-3}$ alkyl, X is $R_1$, Y is $R_2$ and E has an amino group ($R_8$ is amino). As described in step M, reductive alkylation of hydrazine derivative (m) using 1 equivalent of the appropriate carbonyl derivative and sodium cyanoborohydride as the reducing agent produces the desired mono-alkyl hydrazine. Without further purification, this intermediate is subsequently treated with a suitable group ((i) or (i')), followed by acid work up to afford final product o as described in step M. Using 2 equivalents of the carbonyl derivative results in the preparation of the dialkyl (or diarylalkyl) hydrazine as described in step N.

D. General Synthetic Methods

Preferred means of chemically coupling (as for example, amide bond function) include formation of a peptide bond by using conventional coupling reagents known in the art. See Bodanszky, N., *Peptide Chemistry*, pp. 55–73, Springer-Verlag, New York (1988) and references cited therein. The chemical coupling may be either by means of one-step or two-step coupling. In one-step coupling, the two coupling partners are coupled directly. Preferred coupling reagents for one-step coupling of the include DCC with HOBt, EDC with HOBt, HBTU or TBTU. In two-step coupling, an activated ester or anhydride of the C-terminal carboxy group of one coupling partner is formed prior to its coupling to the other coupling partner.

For preparation of certain compounds having hydrogenation sensitive substituent groups, it is preferred to avoid the use of hydrogen gas with palladium on carbon for hydrogenation steps. Another preferred method for preparing compounds of the present invention containing hydrogenation sensitive groups such as alkenyl or aryl moieties substituted with halogen, cyano, nitro, or —S—$Z_1$, is to use boron tris(trifluoroacetate), $B(OCOCF_3)_3$, to cleave protecting groups such as the $N^g$-nitro of a guanidino group. The reagent is prepared by the reaction of $BBr_3$ and $CF_3COOH$ in dichloromethane at 0° C. The reagent is also commercially available. Generally, the $N^g$-nitro compound is treated with boron tris(trifluoroacetate) in trifluoroacetic acid at 0° C. See, e.g., Fieser, M. and Fieser, L. F., *Reagents for Organic Synthesis*, p. 46, John Wiley & Sons, New York (1974); Pless, J., and Bauer, W. *Angew. Chem., Internat. Ed.*, 12, 147 (1973).

In addition, another preferred reagent for selective nitro group cleavage is titanium trichloride. This reagent is commercially available. The $N^g$ nitro compound is treated with titanium trichloride in aqueous methanol containing an ammonium acetate buffer followed by exposure of the reaction mixture to air or dimethyl sulfoxide. Freidinger, R. M., Hirschmann, R., and Veber, D. F., *J. Org. Chem.*, 43, 4800 (1978).

3. Selection of Preferred Compounds

The compounds of the present invention are screened for their ability to inhibit some or all of thrombin, factor Xa, plasmin, recombinant tissue plasminogen activator (rt-PA), activated protein C (aPC), chymotrypsin, and trypsin as set forth below. Certain of the preferred compounds are distinguished by their ability to inhibit thrombin, while not substantially inhibiting some or all of plasmin, tissue plasminogen activator (t-PA), activated protein C (aPC), chymotrypsin, and trypsin. With respect to thrombin and the other enzymes and as used herein, the term "not substantially inhibiting" means that the $IC_{50}$ (or $K_i$) for plasmin, t-PA, aPC, chymotrypsin, and trypsin for a given compound is greater than or equal to its $IC_{50}$ (or $K_i$, respectively) for thrombin. Preferably the ratio of $IC_{50}$'S for plasmin, and the other enzymes, to $IC_{50}$ for thrombin will be at least about 25 or greater, more preferably about 100 or greater. It is believed that the ability to selectively inhibit thrombin will result in therapeutic benefits to patients.

With respect to compounds within the present invention that inhibit members within the trypsin/chymotrypsin family, including trypsin, chymotrypsin, elastase, and serine proteases involved in the coagulation cascade, "not specifically inhibiting" means the $IC_{50}$ or $K_i$ for the target enzyme is less than or equal to the $IC_{50}$ or $K_i$ for non-target enzymes contacted with the inhibitor.

For screening compounds using these assays, the compounds of the present invention are dissolved in buffer to give solutions containing concentrations such that assay concentrations range from 0 to 100 micromolar. In the assays for thrombin, plasmin, t-PA, aPC, chymotrypsin, and trypsin, a chromogenic synthetic substrate is added to a solution containing test compound and the enzyme of interest and the residual catalytic activity of that enzyme is determined spectrophotometrically. The $IC_{50}$ -of a compound of the present invention is determined from the rate of substrate turnover caused by the specific enzyme being measured. $IC_{50}$ is the concentration of test compound which gives 50% inhibition of the rate of substrate turnover. Likewise, the $K_i$ of a compound of the present invention is determined from the rate of substrate turnover caused by the specific enzyme being measured at various enzyme concentrations. Example A provides exemplars of in vitro assays used to select the compounds of the present invention.

Certain of the preferred compounds of the present invention have a $K_i$ of about 0.001 to about 200 nM in the thrombin assay. Especially preferred compounds have a $K_i$ of about 0.001 to about 50 nM. The more especially preferred compounds have a $K_i$ of about 0.001 to about 10 nM.

Certain of the preferred compounds of the present invention have a $IC_{50}$ for plasmin, t-PA, aPC, chymotrypsin, and trypsin which is at least 10 times greater than its $IC_{50}$ for thrombin. Especially preferred compounds have an $IC_{50}$ for plasmin, t-PA, aPC, chymotrypsin, and trypsin which is about 20 to about 100,000 times greater than its $IC_{50}$ for thrombin. More especially preferred compounds have an $IC_{50}$ for plasmin, t-PA, aPC, chymotrypsin, and trypsin which is about 100 to about 1,000,000 times greater than its $IC_{50}$ for thrombin. In the event that a compound of the present invention has an $IC_{50}$ with respect to plasmin, t-PA, aPC, chymotrypsin, or trypsin which is greater than the highest concentration of compound tested, the highest concentration of compound tested is considered to be the reported $IC_{50}$.

The compounds of the present invention are dissolved in buffer to give solutions containing concentrations such that assay concentrations range from 0 to 100 micromolar. In the assays for factor Xa, thrombin, plasmin, t-PA, aPC, chymotrypsin, and trypsin, a chromogenic synthetic substrate is added to a solution containing test compound and the enzyme of interest, and the residual catalytic activity of that enzyme is determined spectrophotometrically. The $IC_{50}$ of a compound of the present invention is determined from the rate of substrate turnover caused by the specific enzyme being measured. $IC_{50}$ is that concentration of test compound giving 50% inhibition of the rate of substrate turnover. Likewise, the $K_i$ of a compound of the present invention is determined from the rate of substrate turnover caused by the specific enzyme being measured at various enzyme concentrations. Example A provides an example of the in vitro assays used to select the preferred compounds of the present invention.

Example A provides a method for identifying and selecting compounds of the present invention that inhibit thrombin, plasmin, t-PA, aPC, chymotrypsin and trypsin to a greater extent than they inhibit factor Xa and, thus, have utility as inhibitors of those proteases.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

The therapeutically effective amount of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

5. Utility and Methods

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent, inhibit and/or attenuate thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vacuum therein as a means to draw blood obtained by venipuncture into the tube is well known in the medical arts. Kasten, B. L., "Specimen Collection", *Laboratory Test Handbook*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of thrombin, and as such, can be incorporated into blood collection tubes to prevent clotting of the mammalian blood drawn into them.

The compounds of the present invention are used alone, in combination with other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as a pharmaceutical agent for preventing, inhibiting and/or attenuating thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets capsules or elixirs taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a "therapeutically effective amount" of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

Certain compounds of the present invention have utility as inhibitors of proteases within the trypsin/chymotrypsin class of enzymes. Members of that class include, but are not limited to, elastase, chymotrypsin, and the serine proteases trypsin, thrombin, factor Xa, and factor VIIa. With respect to the inhibitors within the present invention directed at serine proteases acting within the coagulation cascade, e.g. inhibitors of thrombin, factor Xa and factor V11a, such have in vitro and in vivo utilities as provided hereinabove for thrombin inhibitors.

Elastase has been implicated in a variety of conditions, including pulmonary hypertension (Rabinovitch, M., *Acta Paediatr. Jpn* 37:657–666 (1995)), idiopathic pulmonary fibrosis, rheumatoid arthritis, adult respiratory distress syndrome, cystic fibrosis, and other inflammatory diseases and conditions (Doring, G., *Am. J. Respir. Crit. Care Med.* 150:S114–S117 (1994)). Inhibition of elastase was shown to prevent or retard progression of pulmonary hypertension (Rabinovitch). Thus, inhibitors of the present invention directed toward elastase are useful as pharmaceutical compositions for the inhibition of elastase in conditions where elastase activity is associated with a pathological condition.

Elevated levels of chymotrypsin and trypsin are associated with the pathological effects resulting from pancreatitis (see U.S. Pat. No. 5,534,498). Animal studies of chemically-induced pancreatitis suggest that the disorder is rooted in the inability of pancreatic acinar cells to excrete digestive proenzymes, resulting in activation of trypsinogen to trypsin by lysosomal hydrolases within the cell. The amount of trypsin produced exceeds protective levels of protease inhibitor normally available.

The elevated levels of trypsin then cause activation of the other digestive enzymes co-localized with trypsin in the lysosome, such as chymotrypsin. The net effect of the enzyme activation is pancreatitis, which is characterized by damage to the pancreas and surrounding tissues from auto-digestion of the cells by the various digestive enzymes. These activated digestive enzymes also cause edema, interstitial hemorrhage, vascular damage, coagulation necrosis, fat necrosis and parenchymal cell necrosis.

Inhibitors of the present invention directed toward either trypsin or chymotrypsin, or other members of the trypsin/chymotrypsin family that contribute to the deleterious effects of pancreatitis, are useful for the prevention and treatment of pancreatitis in mammals.

In addition to the in vivo utilities, inhibitors of the present invention also find utility in vitro. Inhibitors of enzymes within the coagulation cascade are useful inhibitors of blood coagulation in vitro, as described hereinabove. Inhibitors of other enzymes within the trypsin/chymotrypsin family, including trypsin, chymotrypsin, and elastase, are useful reagents in in vitro assays designed to measure the activity of such enzymes.

For instance, to determine or confirm the presence of active trypsin, chymotrypsin, or elastase in a sample, the activity of the enzyme in the sample is determined in the presence and absence of the specific inhibitor (which may be labeled using a radioactive or other detectable label). Lower activity measured in the presence of inhibitor as compared to in the absence of inhibitor demonstrates inhibition of the enzyme and, thus, its presence in the sample.

Similarly, the level of activity of an enzyme present in a sample is determined by adding inhibitor to the sample in a range of titrating doses, and calculating activity of the enzyme at each escalating dose of inhibitor. The concentration of inhibitor that completely inhibits the enzyme in the assay, along with knowledge of the assay parameters and characteristic of enzyme inhibition, allows one to calculate the activity of the enzyme in the sample.

The level of chymotrypsin measured in stool samples in vitro is used as an indicator of pancreatitis (Riedel, L. et al., *Gut* 32:321–324 (1991); Chari, S., *Trop. Gastroenterol.,* 11:144–147 (1990)). Chymotrypsin inhibitors of the present invention are useful in such assays to evaluate the level of active chymotrypsin in such a sample, according to protocols such as those outlined hereinabove.

An additional use of the inhibitors of the present invention is their use to quench enzymatic reactions effected by the target enzyme. Thus, to control or prevent digestion of a sample with trypsin or chymotrypsin, an inhibitor of trypsin or chymotrypsin, respectively, is added in inhibit the target enzyme and, thus, control or prevent digestion by that enzyme.

Certain compounds of the present invention can also be useful inhibitors of elastase, and are. therefore useful pharmaceutical agents for the control of inflammation.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

I. Preparation of 1-[5-(2-Amino-6-methylpyridyl) methylcarboxamido-methyl]-3-(2-benzyloxycarbonylhydrazino)-6-methylpyrazinone, Hydrotrifluoroacetate (Examples 1 to 8)

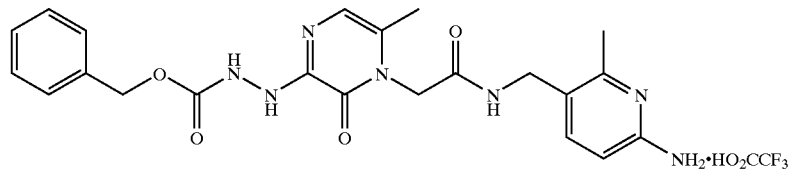

Example 1

Preparation of Ethyl N-(1-cyanoethyl)glycine (Step A)

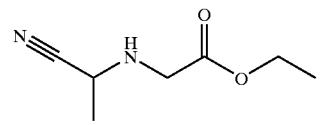

To a suspension of glycine ethyl ester hydrochloride (3.0 g, 0.021 mol) in DCM (80 mL) was added $Et_3N$ (3.0 mL, 0.021 mol). The resulting mixture was stirred at room temperature for 10 minutes, then acetaldehyde (1.2 mL, 0.021 mol) was added, followed by the drop-wise addition of TMSCN (2.86 mL, 0.021 mol). The resulting homogeneous solution was stirred at room temperature for 18 hours, then was diluted with DCM (100 mL) and washed with brine (100 mL), dried ($Na_2SO_4$), and concentrated in vacuo. The crude mixture was purified by flash column chromatography on silica gel (7:3 EtOAc/hexane). The title compound (3.5 g, 87%) was isolated as its white, solid, hydrochloride salt. TLC $R_f$ (free base) 0.8 (EtOAc). $^1$H NMR (methanol-$d_4$) δ1.34 (t, J=7.2 Hz, 3H), 1.73 (d, J=7.2 Hz, 3H), 4.16 (d, J=4 Hz, 2H), 4.33 (q, J=7.2 Hz, 2H), 4.70 (q, J=7.2 Hz, 1H).

Example 2

Preparation of 3,5-dichloro-1-ethoxycarbonylmethyl-6-methylpyrazinone (Step B)

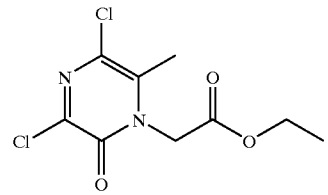

To a suspension of the compound of Example 1 (3.5 g, 0.018 mol) in 1,2-dichlorobenzene (20 mL), was added oxalyl chloride (6.34 mL, 0.074 mol). After stirring the resulting mixture at 110° C. for 18 hours, the excess oxalyl chloride was quenched by adding coarse silica gel. The resulting mixture was purified by flash column chromatography on silica gel (DCM followed by 1:1 EtOAc/hexane) to afford the title compound (3.7 g, 82%) as a dark oil. TLC $R_f$ 0.6 (1:1 EtOAc/hexane). $^1$H NMR ($CDCl_3$) δ1.32 (t, J=7.6 Hz, 3H), 2.41 (s, 3H), 4.28 (q, J=7.6 Hz, 2H), 4.84 (s, 2H).

Example 3

Preparation of 5-chloro-1-ethoxycarbonylmethyl-3-hydrazino-6-methylpyrazinone (Step C)

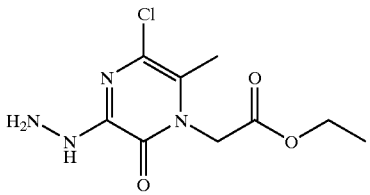

To a solution of the compound of Example 2 (9.4 g, 0.036 mol) in dioxane (100 mL), was added hydrazine (3.35 mL, 0.107 mol). The resulting mixture was heated at 60 to 70° C. After 2 hours, the reaction mixture was diluted with water (200 mL) and extracted with EtOAc (3×150 mL). The combined organic phases were washed with brine (300 mL), dried ($Na_2SO_4$), and concentrated under reduced pressure to afford the title compound (7.3 g, 80%) as a pale yellow solid. TLC $R_f$ 0.8 (EtOAc). $^1$H NMR ($CDCl_3$) δ1.30 (t, J=6.8 Hz, 3H), 2.28 (s, 3H), 3.9 (br s, 2H), 4.25 (q, J=6.8 Hz, 2H), 4.76 (s, 2H), 7.1 (br s, 1H).

Example 4

Preparation of 1-ethoxycarbonylmethyl-3-hydrazino-6-methylpyrazinone (Step D)

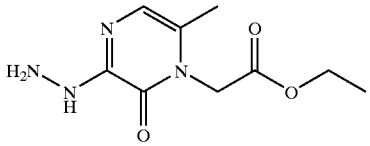

A mixture of the compound of Example 3 (7.3 g, 0.028 mol), ammonium formate (7.1 g, 0.112 mol), and Pd/C (10%, 2.0 g) in MeOH (50 mL) was refluxed for 1 hour. The reaction mixture was filtered through Celite and evaporated in vacuo to afford the title compound as a pale yellow solid which used in the next step without further purification. $^1$H NMR (methanol-$d_4$) δ1.29 (t, J=7.6 Hz, 3H), 2.20 (s, 3H), 4.24 (q, J=7.6 Hz, 2H), 4.83 (s, 2H), 6.71 (s, 1H). HPLC $R_t$ 5.41 minutes (water/ACN/TFA, 5 to 75%, 0.1% TFA, 20 minutes).

Example 5

Preparation of 1-carboxymethyl-3-hydrazino-6-methylpyrazinone (Step G)

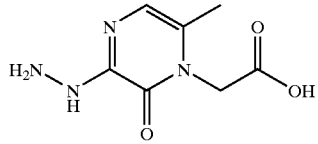

A solution of the compound of Example 4 (6.3 g, 0.028 mol) in HCl (6N, 160 mL) was heated at 60 to 70° C. for 2 hours. The reaction mixture was concentrated under vacuum to afford the title compound (5.0 g, 91%) as a yellow solid, which used in the next step without further purification. $^1$H NMR ($D_2O$) δ2.18 (s, 3H), 4.8 (s, 2H), 6.71 (s, 1H).

Example 6

Preparation of 3-(2-benzyloxycarbonylhydrazino)-1-carboxymethyl-6-methylpyrazinone (Step H)

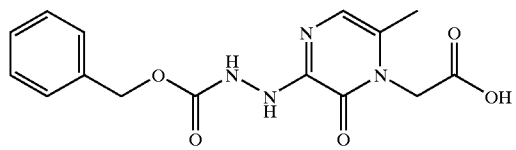

To a solution of the compound of Example 5 (Step G) (5.0 g, 0.025 mol) and $NaHCO_3$ (9.4 g, 0.112 mol) in water (180 mL), was added drop-wise a solution of benzylchloroformate (6.0 mL, 0.042 mol) in dioxane (300 mL). The resulting mixture was stirred at room temperature for 4 hours, diluted with water (200 mL), and washed with ether (200 mL). The aqueous phase was acidified with aqueous 2M $KHSO_4$ and extracted with EtOAc (3×300 mL). The combined organic phases were washed with brine (400 mL), dried ($Na_2SO_4$), and concentrated in vacuo. The crude mixture was purified by flash chromatography on silica gel to afford the title compound (7.35 g, 90%) as a pale brown solid. $^1$H NMR (DMSO-$d_4$) δ2.15 (s, 3H), 4.3 (br s, 1H), 4.73 (s, 2H), 5.12 (s, 2H), 6.76 (s, 1H), 7.20–7.50 (m, 5H), 9.7 (br s, 1H), 10.0 (br s, 1H). HPLC $R_t$ 8.10 minutes (water/ACN/TFA, 5 to 75%, 0.1% TFA, 20 minutes).

Example 7

Preparation of 3-(2-benzyloxycarbonylhydrazino)-1-[5-(2-tert-butoxycarbonylamino-6-methylpyridyl)methylcarboxamidomethyl]-6-methylpyrazinone (Step I)

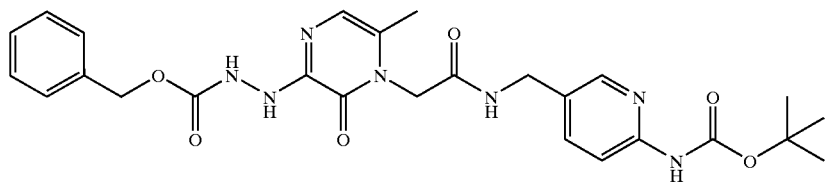

4-NMM (1.9 mL, 17.2 mmol) was added to a solution of the compound of Example 6 (Step H) (1.9 g, 5.7 mmol), 2-tert-butoxycarbonylamino-5-aminomethyl-6-methyl-pyridine (1.63 g, 6.86 mmol), EDC (1.32 g, 6.86 mmol), and HOAt (0.93 g, 6.86 mmol) in DMF (50 mL). After stirring at room temperature for 18 hours, the solution was concentrated in vacuo. The resulting mixture was diluted with EtOAc (100 mL) and washed with saturated aqueous ammonium chloride (50 mL), saturated aqueous NaHCO₃ (50 mL), and brine (50 mL); then, dried (Na₂SO₄) and concentrated in vacuo. The crude material was purified by flash chromatography on silica gel (EtOAc followed by 95:5 DCM/MeOH) affording the title compound (1.5 g, 50%) as a white solid. TLC R$_f$ 0.2 (EtOAc). ¹H NMR (DMSO-d₄) δ1.45 (s, 9H), 2.10 (s, 3H), 2.36 (s, 3H), 4.25 (d, J=5.2 Hz, 2H), 4.65 (s, 2H), 5.08 (s, 2H), 6.68 (s, 1H), 7.20–7.40 (m, 5H), 7.50–7.60 (m, 2H), 8.66 (br s, 2H), 9.08 (br s, 1H), 9.59 (br s, 1H).

Example 8

Preparation of 1-[5-(2-amino-6-methylpyridyl) methylcarboxamidomethyl]-3-(2-benzyloxycarbonylhydrazino)-6-methylpyrazinone, Hydrotrifluoroacetate (Step K)

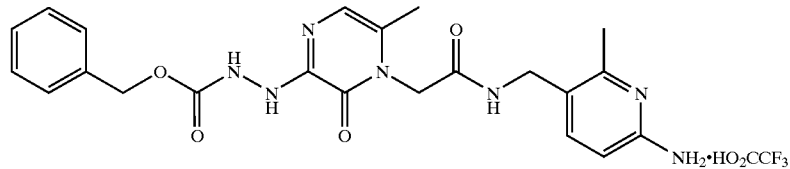

TFA (10 mL) was added to a solution of the compound of Example 7 (Step I) (0.21 g, 0.38 mmol) in DCM (10 mL). This clear solution was stirred at room temperature for 1 hour, then concentrated in vacuo. The crude residue was purified by preparative RP-HPLC (water/ACN/TFA 0 to 50% gradient, 0.1% TFA) to afford the title compound as a white solid. ¹H NMR (methanol-d₄) δ2.21 (s, 3H), 2.51 (s, 3H), 4.30–4.36 (m, 2H), 4.76 (s, 2H), 5.20 (s, 2H), 6.67 (s, 1H), 6.81 (d, J=9.2 Hz, 1H), 7.30–7.42 (m, 5H), 7.84 (d, J=9.2 Hz, 1H), 8.8 (br s, 1H); MS (m/z) 452.2 (M+1); HPLC R$_t$ 11.0 minutes (water/ACN/TFA, gradient 0 to 50%, 0.1% TFA, 20 minutes).

II. Preparation of 1-[5-(2-Amino-6-methylpyridyl) methylcarboxamidomethyl]-3-(2-benzylsulfonylhydrazino)-6-methylpyrazinone, Hydrotrifluoroacetate (Examples 9 to 10)

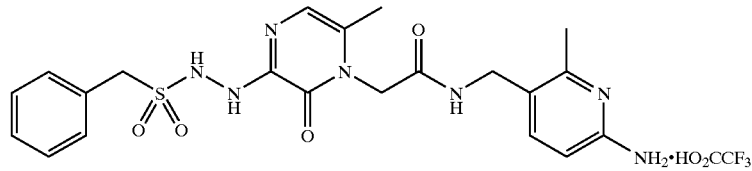

Example 9

Preparation of 1-[5-(2-tert-butoxycarbonylamino-6-methylpyridinyl)methylcarboxamidomethyl]-3-hydrazino-6-methylpyrazinone Hydrochloride (Step J)

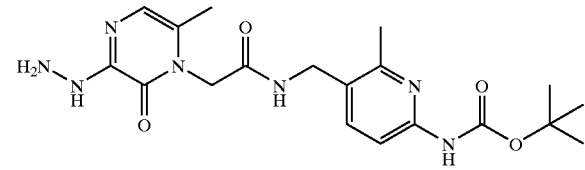

A mixture of the compound of Example 7 (0.85 g, 1.54 mmol), hydrochloric acid (1 M, 1.54 mL, 1.54 mmol) and Pd/C (10%, 0.4 g) in MeOH (50 mL) was hydrogenated at atmospheric pressure for 1 hour. The reaction mixture was filtered through Celite and was evaporated in vacuo to afford the title compound (0.65 g, 93%) as a pale yellow solid. ¹H NMR (methanol-d₄) δ1.52 (s, 9H), 2.20 (s, 3H), 2.46 (s, 3H), 4.38 (s, 2H), 4.79 (s, 2H), 6.65 (s, 1H), 7.60 (d, J=8.4 Hz, 1H), 7.68 (d, J=8.4 Hz, 1H). HPLC R$_t$ 6.89 minutes (water/ACN/TFA, 5 to 75%, 0.1% TFA, 20 minutes).

Example 10

Preparation of 1-[5-(2-amino-6-methylpyridyl)methylcarboxamidomethyl]-3-(2-benzylsulfonylhydrazino)-6-methylpyrazinone, Hydrotrifluoroacetate (Step L)

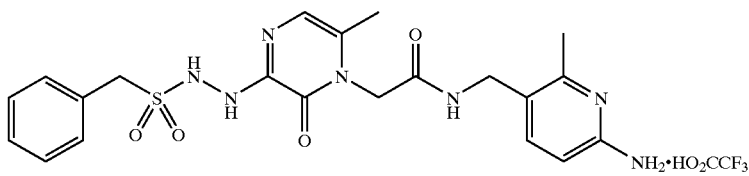

To a mixture of the compound of Example 9 (0.28 g, 0.4 mmol) and $Et_3N$ (0.17 mL, 1.2 mmol) in THF (20 mL) was added α-toluenesulfonyl chloride (84 mg, 0.43 mmol). The resulting mixture was stirred at room temperature for 1 hour, then was concentrated in vacuo. The crude residue was diluted with DCM (10 mL), and then TFA (10 mL) was added. This clear solution was stirred at room temperature for 1 hour then was concentrated under reduced pressure. The crude residue was purified by preparative RP-HPLC (water/ACN/TFA) to afford the title compound (0.1 g) as a white solid. $^1H$ NMR (methanol-$d_4$) δ2,21 (s, 3H), 2.52 (s, 3H), 4.30–4.35 (m, 2H), 4.46 (s, 2H), 4.76 (s, 2H), 6.80 (s, 1H), 6.83 (d, J=9.2 Hz, 1H), 7.31–7.50 (m, 5H), 7.85 (d, J=9.2 Hz, 1H), 8.8 (br s, 1H) ; MS (m/z) 472.2 (M+1). HPLC $R_t$ 10.9 minutes (water/ACN/TFA, 0 to 50%, 0.1% TFA, 20 minutes).

III. Preparation of Other Substituted-Pyrazinones (Examples 11 to 13)

Example 11

Preparation of 1-[5-(2-amino-6-methylpyridyl)methylcarboxamidomethyl]-3-(2-benzylaminocarbonylhydrazino)-6-methylpyrazinone, Hydrotrifluoroacetate

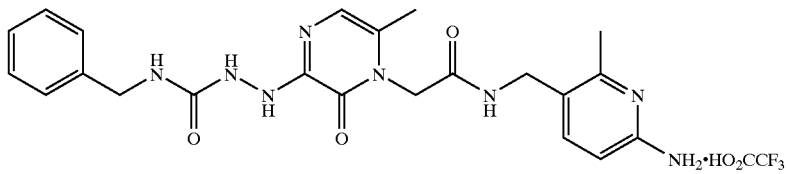

The title compound was prepared from the compound of Example 9 (100 mg, 0.22 mmol) and benzylisocyanate (0.033 mL; 0.26 mmol) using the procedure of Example 10 (Step L). $^1H$ NMR (methanol-$d_4$) δ2.21 (s, 3H), 2.51 (s, 3H), 4.29–4.33 (m, 2H), 4.37 (s, 2H), 4.76 (s, 2H), 6.69 (s, 1H), 6.81 (d, J=9.2 Hz, 1H), 7.20–7.35 (m, 5H), 7.84 (d, J=9.2 Hz, 1H), 8.8 (br s, 1H); MS (m/z) 451.2 (M+1). HPLC $R_t$ 9.67 minutes (water/ACN/TFA, 0 to 50%, 0.1% TFA, 20 minutes).

Example 12

Preparation of 1-[5-(2-amino-6-methylpyridyl)methylcarboxamidomethyl]-6-methyl-3-(2-phenylacetylhydrazino)pyrazinone, Hydrotrifluoroacetate

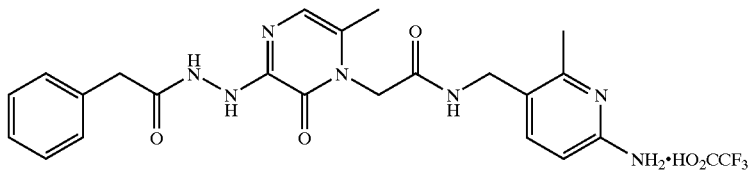

The title compound was prepared from the compound of Example 9 (100 mg, 0.22 mmol) and phenylacetyl chloride (0.032 mL, 0.24 mmol) using the procedure of Example 10 (Step L). $^1$H NMR (methanol-$d_4$) δ2.18 (s, 3H), 2.49 (s, 3H), 3.63 (s, 2H), 4.29 (s, 2H), 4.71 (s, 2H), 6.73 (s, 1H), 6.80 (d, J=9.2 Hz, 1H), 7.20–7.40 (m, 5H), 7.83 (d, J=9.2 Hz, 1H).

Example 13

Preparation of 1-[5-(2-amino-6-methylpyridyl)methylcarboxamidomethyl]-3-(2-benzoylhydrazino)-6-methylpyrazinone, Hydrotrifluoroacetate

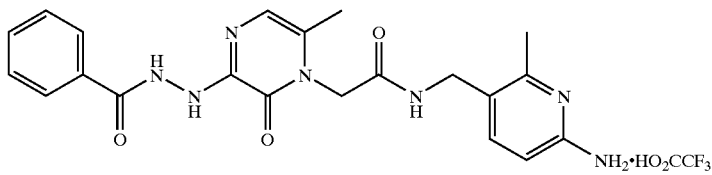

The title compound was prepared from the compound of Example 9 (0.2 g, 0.49 mmol) and benzoyl chloride (0.061 mL, 0.53 mmol) using the procedure of Example 10 (Step L). $^1$H NMR ($D_2O$) δ2.17 (s, 3H), 2.46 (s, 3H), 4.41 (s, 2H), 4.83 (s, 2H), 6.76 (s, 1H), 6.81 (d, J=8.8 Hz, 1H), 7.50–7.90 (m, 6H). MS (m/z) 422.2 (M+1). HPLC $R_t$ 8.8 minutes. (water/ACN/TFA, 0 to 50%, 0.1% TFA, 20 minutes).

IV. Preparation of 1-[5-(2-Amino-6-methylpyridyl)methylcarboxamidomethyl]-3-(2-benzyloxycarbonylhydrazino)-5-chloro-6-methylpyrazinone, Hydrotrifluoroacetate (Examples 14 to 17)

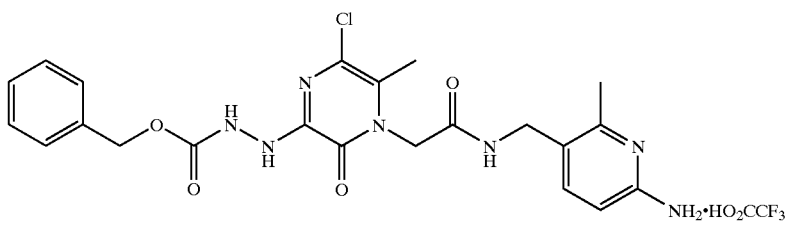

Example 14

Preparation of 1-carboxymethyl-5-chloro-3-hydrazino-6-methylpyrazinone (Step F)

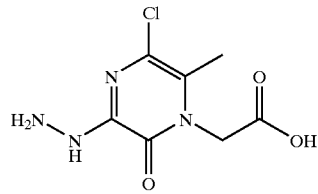

A solution of the compound of Example 3 (2.15 g, 8.26 mmol) in HCl (6 N, 160 mL) was heated at 60 to 70° C. After 2 hours the reaction mixture was concentrated in vacuo to afford the title compound as a red-yellow solid, which used in the next step without further purification. $^1$H NMR (D$_2$O) δ2.40 (s, 3H), 4.94 (s, 2H). HPLC R$_t$ 4.46 minutes (water/ACN/TFA, 5 to 75%, 0.1% TFA, 20 minutes).

Example 15

Preparation of 3-(2-benzyloxycarbonylhydrazino)-1-carboxymethyl-5-chloro-6-methylpyrazinone (Step H)

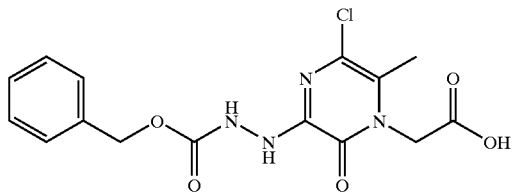

To a solution of the compound of Example 14 (1.9 g, 8.26 mmol) and NaHCO$_3$ (2.08 g, 24.75 mmol) in water, (60 mL) was added drop-wise a solution of benzyl chloroformate (1.9 mL, 13.21 mmol) in dioxane (100 mL). The resulting mixture was stirred at room temperature for 4 hours, then was diluted with water (60 mL) and washed with ether (100 mL). The aqueous solution was acidified with 2 M KHSO$_4$ and extracted with EtOAc (3×100 mL). The combined organic phases were washed with brine (200 mL), dried (Na$_2$SO$_4$), and concentrated in vacuo. The crude mixture was purified by flash chromatography on silica gel (1:1 EtOAc/hexane, then 9:1 DCM/MeOH) to afford the title compound (1.6 g, 53%) as a pale yellow solid. $^1$H NMR (DMSO-d$_4$) δ2.24 (s, 2H), 4.64 (s, 2H), 5.13 (s, 2H), 7.20–7.45 (m, 5H), 9.22 (s, 1H), 9.29 (s, 1H). HPLC R$_t$ 11.4 minutes (water/ACN/TFA, 5 to 75%, 0.1% TFA, 20 minutes).

Example 16

Preparation of 3-(2-benzyloxycarbonylhydrazino)-1-[5-(2-tert-butoxycarbonylamino-6-methylpyridyl)methylcarboxamidomethyl]-5-chloro-6-methylpyrazinone (Step I)

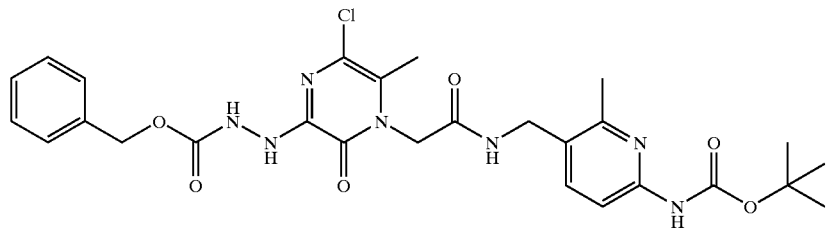

4-NMM (0.18 mL, 1.63 mmol) was added to a solution of the compound of Example 15 (0.20 g, 0.54 mmol), 5-aminomethyl-2-tert-butoxycarbonylamino-6-methylpyridine (0.16 g, 0.65 mmol), EDC (0.13 g, 0.65 mmol), and HOAt (0.09 g, 0.65 mmol) in DMF (10 mL). The resulting solution was stirred at room temperature for 18 hours, then concentrated in vacuo. The resulting mixture was diluted with EtOAc (50 mL), and the resulting solution washed successively with saturated aqueous ammonium chloride (50 mL), saturated aqueous NaHCO$_3$ (50 mL), and brine (50 mL), then dried (Na$_2$SO$_4$) and concentrated in vacuo. The crude material was purified by flash chromatography on silica gel (7:3 EtOAc/hexane) to afford the title compound (0.12 g, 40%) as a white solid. TLC R$_f$ 0.25 (7:3 EtOAc/hexane). $^1$H NMR (DMSO-d$_6$) δ1.45 (s, 9H), 2.22 (s, 3H), 2.36 (s, 3H), 4.25 (d, J=5.2 Hz, 2H), 4.72 (s, 2H), 5.13 (s, 2H), 7.20–7.45 (m, 5H), 7.50–7.60 (m, 2H), 8.7 (br s, 1H), 9.26 (s, 1H), 9.30 (s, 1H), 9.59 (s, 1H).

Example 17

Preparation of 1-[5-(2-amino-6-methylpyridyl)methylcarboxamidomethyl]-3-(2-benzyloxycarbonylhydrazino)-5-chloro-6-methylpyrazinone, Hydrotrifluoroacetate (Step K)

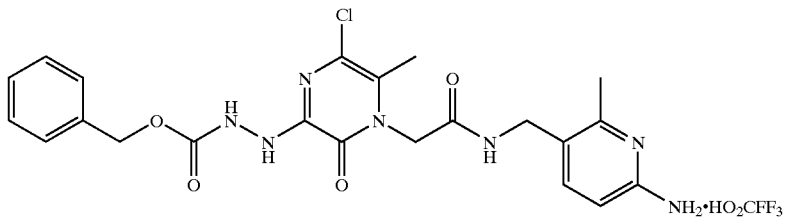

TFA (10 mL) was added to a suspension of the compound of Example 16 (0.24 g, 0.41 mmol) in DCM (10 mL). This clear solution was stirred at room temperature for 1 hour, then concentrated in vacuo. The crude residue was purified by preparative RP-HPLC (water/ACN/TFA) to afford the title compound (0.1 g, 50%) as a white solid. $^1$H NMR (DMSO-d$_6$) δ2.20 (s, 3H), 2.43 (s, 3H), 4.17 (d, J=5.2 Hz, 2H), 4.69 (s, 2H), 5.13 (s, 2H), 6.80 (d, J=9.2 Hz, 1H), 7.20–7.40 (m, 5H), 7.73 (br s, 1H), 7.77 (d, J=9.2 Hz, 1H), 8.8 (br s, 1H), 9.23 (br s, 1H), 9.3 (br s, 1H); MS (m/z) 486.0 (M+1). RP-HPLC R$_t$ 13.3 minutes (water/ACN/TFA, 5 to 50%, 0.1% TFA, 20 minutes).

V. Preparation of 1-[5-(2-Amino-6-methylpyridyl)methylcarboxamidomethyl]-6-methyl-3-(2-phenylsulfonylhydrazino)pyrazinone, Hydrotrifluoroacetate (Examples 18 to 22)

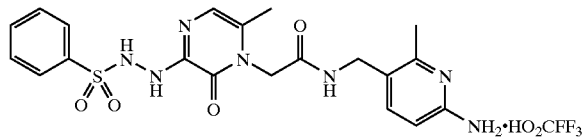

Example 18

Preparation of benzyl N-(1-cyanoethyl)glycine (Step A)

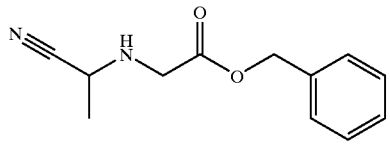

To a suspension of glycine benzyl ester hydrochloride (50.7 g, 0.252 mol) in DCM (1.2 L), was added Et$_3$N (35.1 mL, 0.252 mol). The resulting mixture was stirred at room temperature for 10 minutes, then acetaldehyde (14.1 mL, 0.252 mol) was added, followed by the drop-wise addition of TMSCN (33.6 mL, 0.252 mol). The resulting homogeneous solution was stirred at room temperature for 18 hours, then diluted with DCM (0.5 L). The resulting solution was washed with brine (1 L), dried (Na$_2$SO$_4$), and concentrated in vacuo. The crude mixture was purified by flash column chromatography on silica gel (7:3 EtOAc/hexane). The title compound (43.7g, 68.3%) was isolated as the hydrochloride salt (white solid). TLC R$_f$ (free base) 0.8 (EtOAc). $^1$H NMR (methanol-d$_4$) δ1.63 (d, J=7.2 Hz, 3H), 4.04 (q, J=8.8 Hz, 2H), 4.46 (q, J=6.8 Hz, 1H), 5.27 (s, 2H), 7.30–7.40 (m, 5H).

Example 19

Preparation of 1-benzyloxycarbonylmethyl-3,5-dichloro-6-methylpyrazinone (Step B)

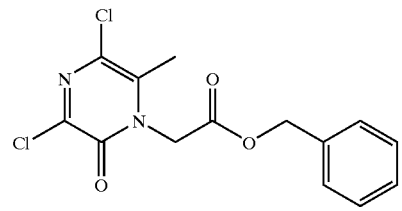

To a suspension of the compound of Example 18 (43.7 g, 0.172 mol) in 1,2-dichlorobenzene (250 mL) was added oxalyl chloride (60 mL, 0.687 mol). The resulting mixture was stirred at 110° C. for 18 hours, then the excess oxalyl chloride was quenched by the addition of coarse silica gel. The resulting mixture was purified by flash column chromatography on silica gel (DCM followed by 1:1 EtOAc/hexane) to afford the title compound (41.6 g, 74%) as a dark oil. TLC R$_f$ 0.6 (1:1 EtOAc/hexane). $^1$H NMR (CDCl$_3$) δ2.35 (s, 3H), 4.88 (s, 2H), 5.23 (s, 2H), 7.30–7.45 (m, 5H).

Example 20

Preparation of 1-benzyloxycarbonylmethyl-5-chloro-3-hydrazino-6-methylpyrazinone (Step C)

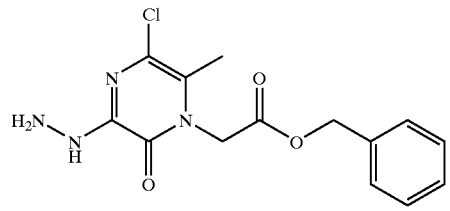

To a solution of the compound of Example 19 (10.0 g, 0.031 mol) in dioxane (100 mL) was added hydrazine (2.89 mL, 0.092 mol). The resulting mixture was heated at 60 to 70° C. for 2 hours, then the reaction mixture was diluted with water (200 mL) and extracted with EtOAc (3×150 mL). The combined organic phases were washed with brine (300 mL), dried (Na$_2$SO$_4$), and concentrated under reduced pressure to afford the title compound (8.8 g, 90%) as a white solid. TLC R$_f$ 0.2 (1:1 EtOAc/hexane). $^1$H NMR (CDCl$_3$) δ2.23 (s, 3H), 3.9 (br s, 2H), 4.81 (s, 2H), 5.22 (s, 2H), 7.1 (br s, 1H), 7.30–7.45 (m, 5H).

Example 21

Preparation of 1-carboxymethyl-3-hydrazino-6-methylpyrazinone (Step E)

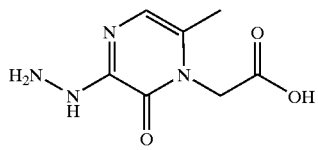

A mixture of the compound of Example 20 (0.5 g, 1.56 mmol), ammonium formate (0.39 g, 6.52 mmol), and Pd/C (10%, 0.2 g) in MeOH (20 mL) was heated at reflux for 1 hour. The reaction mixture was filtered through Celite, then evaporated in vacuo to afford the title compound in quantitative yield as a white solid, which was used in the next step without further purification. $^1$H NMR (D$_2$O) δ2.18 (s, 3H), 4.8 (s, 2H), 6.71 (s, 1H).

Example 22

Preparation of 1-[5-(2-amino-6-methylpyridyl)methylcarboxamidomethyl]-6-methyl-3-(2-phenylsulfonylhydrazino)pyrazinone, Hydrotrifluoroacetate (Step L)

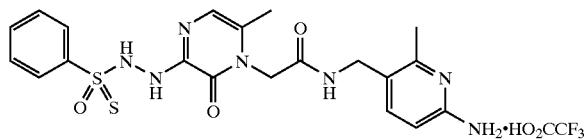

To a mixture of the compound of Example 9 (0.07 g, 0.154 mmol) and Et$_3$N (0.054 mL, 2.5 mmol) in THF (5 mL), was added benzenesulfonyl chloride (0.02 mL, 0.154 mmol). The resulting mixture was stirred at room temperature for 1 hour, then was concentrated in vacuo. The crude residue was diluted with DCM (4 mL) and TFA (4 mL) was added. This clear solution was stirred at room temperature for 1 hour, then was concentrated under reduced pressure. The crude residue was purified by preparative RP-HPLC (eluting with water/ACN/TFA) to afford the title compound (0.1 g) as a white solid. $^1$H NMR (D$_2$O) δ2.16 (s, 3H), 2.49 (s, 3H), 4.34 (s, 2H), 4.78 (s, 2H), 6.72 (s, 1H), 6.84 (d, J=8.8 Hz, 1H), 7.63 (t, J=7.6 Hz, 2H), 7.70–7.85 (m, 2H), 7.93 (d, J=8.4 Hz, 2H). MS (m/z) 458 (M+1). RP-HPLC HPLC R$_t$ 9.62 minutes (water/ACN/TFA, 0 to 50%, 0.1% TFA, 20 minutes).

VI. Preparation of Certain Substituted Pyrazinones (Examples 23 to 57)

Example 23

Preparation of 1-[5-(2-amino-6-methylpyridyl)methylcarboxamidomethyl]-3-[2-cyclopentylacetylhydrazino]-6-methylpyrazinone, Hydrotrifluoroacetate

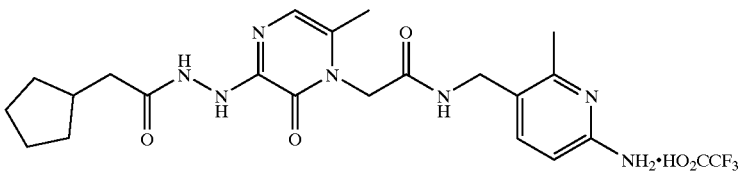

The title compound was prepared from the compound of Example 9 (50 mg, 0.11 mmol) and cyclopentylacetyl chloride (18 mg, 0.12 mmol) following the procedure of Example 22 (Step L). $^1$H NMR (methanol-d$_4$) δ1.20–1.30 (m, 2H), 1.52–1.75 (m, 4H), 1.80–1.94 (m, 2H), 2.20 (s, 3H), 2.22–2.40 (m, 3H), 2.51 (s, 3H), 4.41 (s, 2H), 4.75 (s, 2H), 6.70 (s, 1H), 6.82 (d, J 8.8 Hz, 1H), 7.84 (d, J=8.8 Hz, 1H). MS (m/z) 428.4 (M+1). RP-HPLC R$_t$ 10.2 minutes (water/ACN/TFA, 0 to 50%, 0.1% TFA, 20 minutes).

Example 24

Preparation of 1-[5-(2-amino-6-methylpyridyl)methylcarboxamidomethyl]-3-[2-(2-chlorobenzyloxycarbonyl)hydrazino]-6-methylpyrazinone, Hydrotrifluoroacetate

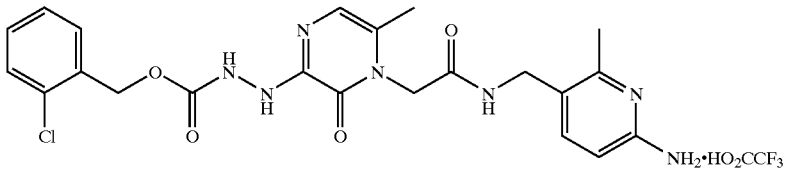

The title compound was prepared from the compound of Example 9 (52 mg, 0.12 mmol) and 2-chlorobenzyl chloroformate (0.018 mL, 0.12 mmol) following the procedure of Example 22 (Step L). $^1$H NMR (methanol-d$_4$) δ2.21 (s, 3H), 2.51 (s, 3H), 4.31 (s, 2H), 4.76 (s, 2H), 5.31 (s, 2H), 6.70 (s, 1H), 6.81 (d, J=9.2 Hz, 1H), 7.30–7.60 (m, 4H), 7.84 (d, J=9.2 Hz, 1H). MS (m/z) 486.9 (M+1). RP-HPLC R$_t$ 12.1 minutes (water/ACN/TFA, 0 to 50%, 0.1% TFA, 20 minutes).

Example 25

Preparation of 3-(2-allyloxycarbonylhydrazino)-1-[5-(2-amino-6-methylpyridyl)methylcarboxamidomethyl]-6-methylpyrazinone, Hydrotrifluoroacetate

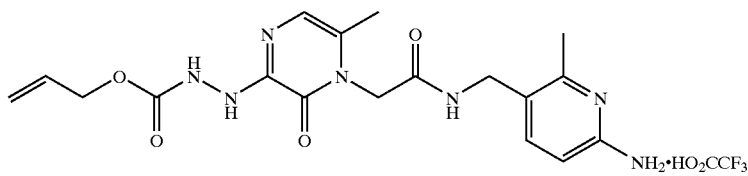

The title compound was prepared from the compound of Example 9 (100 mg, 0.22 mmol) and allyl chloroformate (0.023 mL, 0.22 mmol), following the procedure of Example 22 (Step L). $^1$H NMR (methanol-d$_4$) δ2.20 (s, 3H), 2.51 (s, 3H), 4.31 (s, 2H), 4.64 (d, J=5.2 hz, 2H), 4.75 (s, 2H), 5.23 (d, J=10.0 Hz, 1H), 5.36 (br d, J=16.8 Hz, 1H), 5.90–6.05 (m, 1H), 6.69 (s, 1H), 6.81 (d, J=9.2 Hz, 1H), 7.84 (d, J=9.2 Hz, 1H); MS (m/z) 402 (M+1). RP-HPLC R$_t$ 7.83 minutes (water/ACN/TFA, 0 to 50%, 0.1% TFA, 20 minutes).

Example 26

Preparation of 1-[5-(2-amino-6-methylpyridyl)methylcarboxamidomethyl]-6-methyl-3-(2-phenoxycarbonylhydrazino)pyrazinone, Hydrotrifluoroacetate

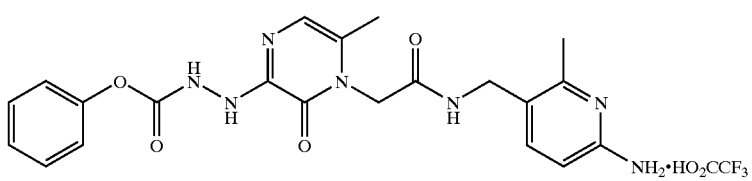

The title compound was prepared from the compound of Example 9 (100 mg, 0.22 mmol) and phenyl chloroformate (0.028 mL, 0.22 mmol) following the procedure of Example 22 (Step L). $^1$H NMR (methanol-d$_4$) δ2.22 (s, 3H), 2.52 (s, 3H), 4.32 (s, 2H), 4.77 (s, 2H), 6.77 (s, 1H), 6.82 (d, J=9.2 Hz, 1H), 7.20–7.32 (m, 3H), 7.40 (t, J=8.0 Hz, 2H), 7.85 (d, J=9.2 Hz, 1H). MS (m/z) 438 (M+1). RP-HPLC R$_t$ 9.98 minutes (water/ACN/TFA, 0 to 50%, 0.1% TFA, 20 minutes).

Example 27

Preparation of 1-[5-(2-amino-6-methylpyridyl)methylcarboxamidomethyl]-3-[2-(4-fluorophenoxycarbonyl)hydrazino]-6-methylpyrazinone, Hydrotrifluoroacetate

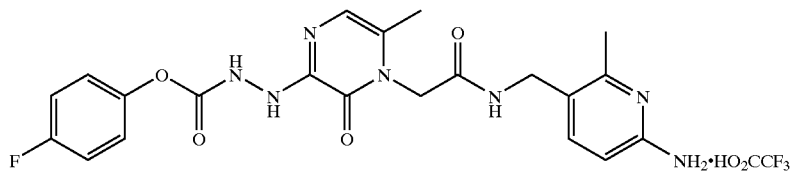

The title compound was prepared from the compound of Example 9 (50 mg, 0.13 mmol) and 4-fluorophenyl chloroformate (0.018 mL, 0.13 mmol) following the procedure of Example 22 (Step L). $^1$H NMR (methanol-d$_4$) δ2.20 (s, 3H), 2.51 (s, 3H), 4.31 (s, 2H), 4.78 (s, 2H), 6.75 (s, 1H), 6.82 (d, J=9.2 Hz, 1H), 7.10–7.30 (m, 4H), 7.90 (d, J=9.2 Hz, 1H).

Example 28

Preparation of 1-[5-(2-amino-6-methylpyridyl)methylcarboxamidomethyl]-3-[2-(3-butenyloxycarbonyl)hydrazino]-6-methylpyrazinone, Hydrotrifluoroacetate

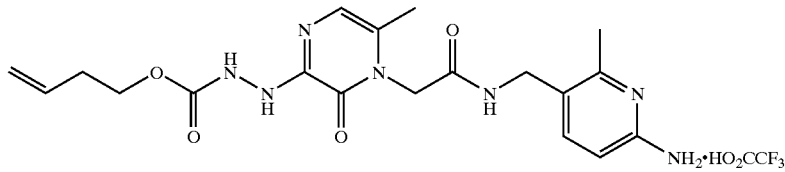

The title compound was prepared from the compound of Example 9 (60 mg, 0.13 mmol) and 3-butenyl chloroformate (0.016 mL, 0.13 mmol) following the procedure of Example 22 (Step L). $^1$H NMR (methanol-$d_4$) δ2.22 (s, 3H), 2.40–2.50 (m, 2H), 2.54 (s, 3H), 4.15–4.23 (m, 2H), 4.34 (s, 2H), 4.78 (s, 2H), 5.05–5.22 (m, 2H), 5.78–5.95 (m, 1H), 6.75 (s, 1H), 6.82 (d, J=9.2 Hz, 1H), 7.86 (d, J=9.2 Hz, 1H). MS (m/z) 416 (M+1). RP-HPLC $R_t$ 8.7 minutes (water/ACN/TFA, 0 to 50%, 0.1% TFA, 20 minutes).

Example 29

Preparation of 1-[5-(2-amino-6-methylpyridyl)methylcarboxamidomethyl]-3-[2-(9-fluroenylmethyloxycarbonyl)hydrazino]-6-methylpyrazinone, Hydrotrifluoroacetate

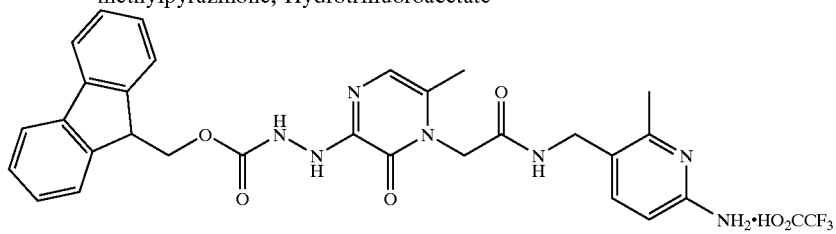

The title compound was prepared from the compound of Example 9 (70 mg, 0.15 mmol) and 9-fluorenylmethyl chloroformate (40 mg, 0.15 mml) following the procedure of Example 22 (Step L). $^1$H NMR (methanol-$d_4$) δ2.22 (s, 3H), 2.53 (s, 3H), 4.30–4.40 (m, 3H), 4.48 (d, J=6.8 Hz, 2H), 4.76 (s, 2H), 6.70 (br s, 1H), 6.83 (d, J=8.8 Hz, 1H), 7.30–7.50 (m, 4H), 7.70–7.85 (m, 3H), 7.86 (d, J=8.8 Hz, 1H). MS (m/z) 540 (M+1). RP-HPLC $R_t$ 15.1 minutes (water/ACN/TFA, 0 to 50%, 0.1% TFA, 20 minutes).

Example 30

Preparation of 1-[5-(2-amino-6-methylpyridyl)methylcarboxamidomethyl]-6-methyl-3-(2-propargyloxycarbonylhydrazino)pyrazinone, Hydrotrifluoroacetate

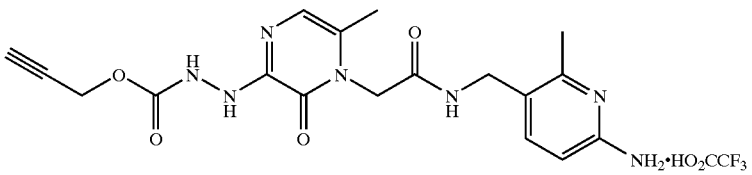

The title compound was prepared from the compound of Example 9 (70 mg, 0.15 mmol) and propargyl chloroformate (0.015 mL, 0.15 mmol) following the procedure of Example 22 (Step L). $^1$H NMR (D$_2$O) δ2.21 (s, 3H), 2.50 (s, 3H), 2.98 (s, 1H), 4.36 (s, 2H), 4.84 (s, 2H), 6.84 (s, 1H), 6.86 (d, J=9.2 Hz, 1H), 7.82 (d, J=9.2 Hz, 1H). MS (m/z) 400 (M+1). RP-HPLC $R_t$ 7.2 minutes (water/ACN/TFA, 0 to 50%, 0.1% TFA, 20 minutes).

Example 31

Preparation of 1-[5-(2-amino-6-methylpyridyl)methylcarboxamidomethyl]-6-methyl-3-(2-neopentyloxycarbonylhydrazino)pyrazinone, Hydrotrifluoroacetate

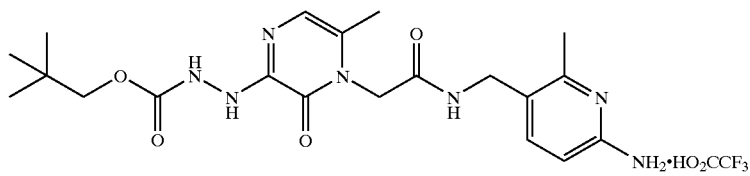

The title compound was prepared from the compound of Example 9 (70 mg, 0.15 mmol) and neopentyl chloroformate (0.023 mL, 0.15 mmol) following the procedure of Example 22 (Step L). $^1$H NMR (D$_2$O) δ0.95 (s, 9H), 2.22 (s, 3H), 2.50 (s, 3H), 3.80–3.90 (m, 2H), 4.36 (s, 2H), 4.85 (s, 2H), 6.85 (s, 1H), 6.86 (d, J=9.2 Hz, 1H), 7.82 (d, J=9.2 Hz, 1H). MS (m/z) 432 (M+1). RP-HPLC R$_t$ 10.8 minutes (water/ACN/TFA, 0 to 50%, 0.1% TFA, 20 minutes).

Example 32

Preparation of 1-[5-(2-amino-6-methylpyridyl)methylcarboxamidomethyl]-3-[2-(2-chlorobenzyloxycarbonyl)hydrazino]-6-methylpyrazinone, Hydrotrifluoroacetate

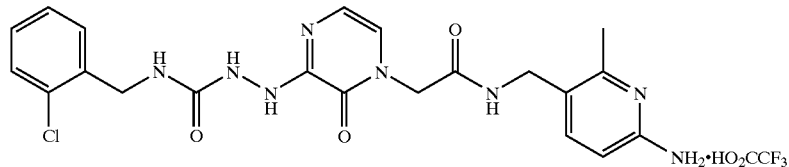

The title compound was prepared from the compound of Example 9 (70 mg, 0.15 mmol) and 2-chlorobenzyl isocyanate (0.023 mL, 0.15 mmol) following the procedure of Example 22 (Step L). $^1$H NMR (methanol-d$_4$) δ2.21 (s, 3H), 2.51 (s, 3H), 4.31 (s, 2H), 4.46 (s, 2H), 4.75 (s, 2H), 6.73 (s, 1H), 6.81 (d, J=8.8 Hz, 1H), 7.20–7.50 (m, 4H), 7.84 (d, J=8.8 Hz, 1H). MS (m/z) 486 (M+1). RP-HPLC R$_t$ 10.9 minutes (water/ACN/TFA, 0 to 50%, 0.1% TFA, 20 minutes).

Example 33

Preparation of 1-[5-(2-amino-6-methylpyridyl)methylcarboxamidomethyl]-3-[2-(3,4-dichlorobenzyloxycarbonyl)hydrazino]-6-methylpyrazinone, Hydrotrifluoroacetate

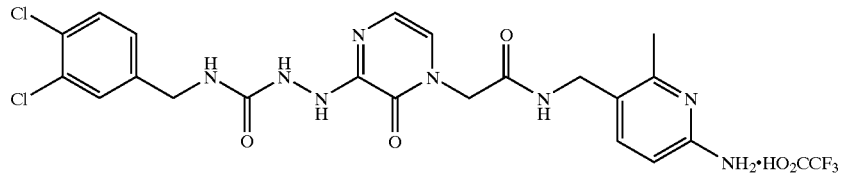

The title compound was prepared from the compound of Example 9 (70 mg, 0.15 mmol) and 3,4-dichlorobenzyl isocyanate (0.023 mL, 0.15 mmol) following the procedure of Example 22 (Step L). $^1$H NMR (methanol-d$_4$) δ2.20 (s, 3H), 2.51 (s, 3H), 4.30–4.35 (m, 4H), 4.75 (s, 2H), 6.74 (s, 1H), 6.81 (d, J=8.8 Hz, 1H), 7.22 (d, J=10.4 Hz, 1H), 7.43 (d, J=8.4 Hz, 1H), 7.49 (s, 1H), 7.84 (d, J=8.8 Hz, 1H). MS (m/z) 519 (M). RP-HPLC R$_t$ 12.7 minutes (water/ACN/TFA, 0 to 50%, 0.1% TFA, 20 minutes).

Example 34

Preparation of 1-[5-(2-amino-6-methylpyridyl) methylcarboxamidomethyl]-3-[2-(benzoylcarbamyl) hydrazino]-6-methylpyrazinone, Hydrotrifluoroacetate

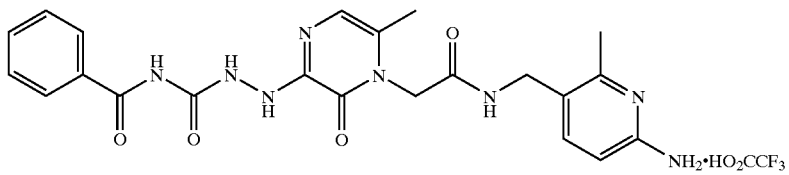

The title compound was prepared from the compound of Example 9 (70 mg, 0.15 mmol) and benzoyl isocyanate (0.019 mL, 0.15 mmol) following the procedure of Example 22 (Step L). $^1$H NMR (D$_2$O) δ2.22 (s, 3H), 2.51 (s, 3H), 4.37 (s, 2H), 4.86 (s, 2H), 6.85–6.88 (m, 2H), 7.61 (t, J=7.6 Hz, 2H), 7.70–7.80 (m, 1H), 7.83 (d, J=8.8 Hz, 1H), 7.93 (d, J=8.0 Hz, 2H). MS (m/z) 465 (M+1). RP-HPLC R$_t$ 10.1 minutes (water/ACN/TFA, 0 to 50%, 0.1% TFA, 20 minutes).

Example 35

Preparation of 1-[5-(2-amino-6-methylpyridyl) methylcarboxamidomethyl]-6-methyl-3-[2-((R)- phenethylcarbamyl)hydrazino]-pyrazinone, Hydrotrifluoroacetate

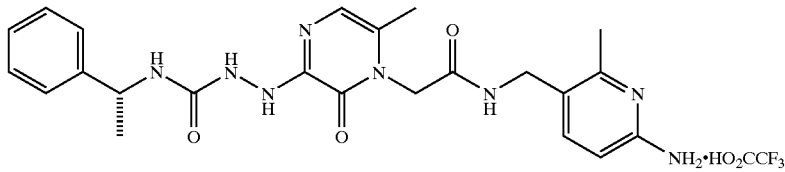

The title compound was prepared from the compound of Example 9 (70 mg, 0.15 mmol) and (R)-(+)-α-methylbenzyl isocyanate (0.22 mL, 0.15 mmol) following the procedure of Example 22 (Step L). $^1$H NMR (D$_2$O) δ1.47 (d, J=6.8 Hz, 3H), 2.23 (s, 3H), 2.49 (s, 3H), 4.36 (s, 2H), 4.86 (s, 2H), 4.82–4.90 (m, 1H), 6.77 (s, 1H), 6.85 (d, J=9.2 Hz, 1H), 7.30–7.50 (m, 5H), 7.81 (d, J=9.2 Hz, 1H). MS (m/z) 465 (M+1). RP-HPLC R$_t$ 10.7 minutes (water/ACN/TFA, 0 to 50%, 0.1% TFA, 20 minutes).

Example 36

Preparation of 1-[5-(2-amino-6-methylpyridyl) methylcarboxamidomethyl]-6-methyl-3-[2-((S)- phenethylcarbamyl)hydrazino]pyrazinone, Hydrotrifluoroacetate

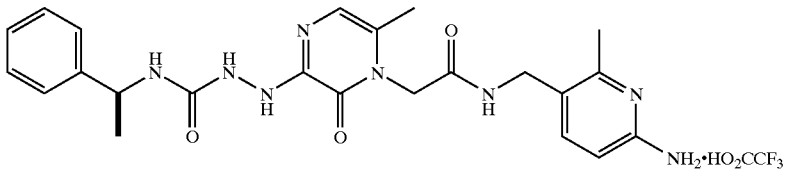

The title compound was prepared from the compound of Example 9 (70 mq, 0.15 mmol) and (S)-(−)-α-methylbenzyl isocyanate (0.022 mL, 0.15 mmol) following the procedure of Example 22 (Step L). $^1$H NMR (D$_2$O) δ1.46 (d, J=7.2 Hz, 3H), 2.22 (s, 3H), 2.49 (s, 3H), 4.36 (s, 2H), 4.85 (s, 2H), 4.82–4.90 (m, 1H), 6.80 (s, 1H), 6.85 (d, J=9.2 Hz, 1H), 7.30–7.50 (m, 5H), 7.81 (d, J=9.2 Hz, 1H). MS (m/z) 465 (M+1). RP-HPLC $R_t$ 10.7 minutes (water/ACN/TFA, 0 to 50%, 0.1% TFA, 20 minutes).

Example 37

Preparation of 1-[5-(2-amino-6-methylpyridyl) methylcarboxamidomethyl]-3-[2-(4-chlorobenzylcarbamyl)hydrazino]-6-methylpyrazinone, Hydrotrifluoroacetate (Step L)

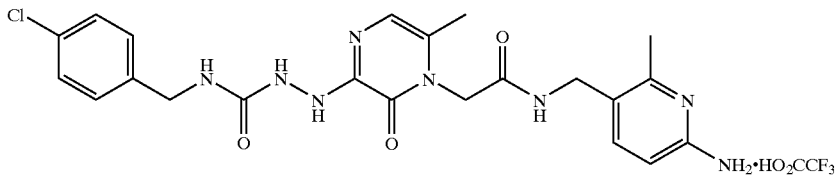

To a solution of 4-chlorobenzylamine (21 μL, 0.169 mmol) in DCM (3 mL) was added, in order, triphosgene in DCM (1.85 mL, 0.03 M, 0.055 mmol) and Et₃N (24 μL, 0.169 mmol). The resulting mixture was stirred at room temperature for 1 hour, then concentrated in vacuo. The residue was diluted with THF (4 mL), then Et₃N (54 μL, 0.385 mmol) was added, followed by addition of the compound of Example 9 (70 mg, 0.15 mmol). The resulting mixture was stirred at room temperature for 1 hour, then was concentrated in vacuo. The crude residue was diluted with DCM (4 mL) and TFA (4 mL). The clear solution was stirred at room temperature for 1 hour, then concentrated in vacuo. The crude residue was purified by preparative RP-HPLC (water/ACN/TFA) to afford the title compound as a white solid. ¹H NMR (D₂O) δ2.21 (s, 3H), 2.50 (s, 3H), 4.36 (s, 2H), 4.85 (s, 2H), 6.84 (s, 1H), 6.85 (d, J=9.2 Hz, 1H), 7.29 (d, J=8.4 Hz, 2H), 7.40 (d, J=8.4 Hz, 2H), 7.81 (d, J=9.2 Hz, 1H). MS (m/z) 485 (M+1). RP-HPLC $R_t$ 11.5 minutes (water/ACN/TFA, 0 to 50%, 0.1% TFA, 20 minutes).

Example 38

Preparation of 1-[5-(2-amino-6-methylpyridyl) methylcarboxamidomethyl]-3-[2-((-)-menthoxyoxycarbonyl)hydrazino]-6-methylpyrazinone, Hydrotrifluoroacetate The title compound was prepared from the compound of Example 9 (70 mg, 0.15 mmol) and (–)-menthyl chloroformate (0.033 mL, 0.15 mmol) following the procedure of Example 22 (Step L). ¹H NMR (D₂O) δ0.60–0.95 (m, 10H), 0.98–1.15 (m, 2H), 1.35–1.50 (m, 2H), 1.55–1.70 (m, 2H), 1.92–2.00 (m, 2H), 2.17 (s, 3H), 2.46 (s, 3H), 3.29 (m, 1H), 4.31 (s, 2H), 4.40–4.60 (m, 1H), 6.80 (s, 1H), 6.81 (d, J=9.2 Hz, 1H), 7.78 (d, J=9.2 Hz, 1H). MS (m/z) 500 (M+1). RP-HPLC $R_t$ 12.0 minutes (water/ACN/TFA, 5 to 75%, 0.1% TFA, 20 minutes).

Example 39

Preparation of 1-[5-(2-amino-6-methylpyridyl) methylcarboxamidomethyl]-6-methyl-3-[2-(4-nitrobenzyloxycarbonyl)hydrazino]pyrazinone, Hydrotrifluoroacetate

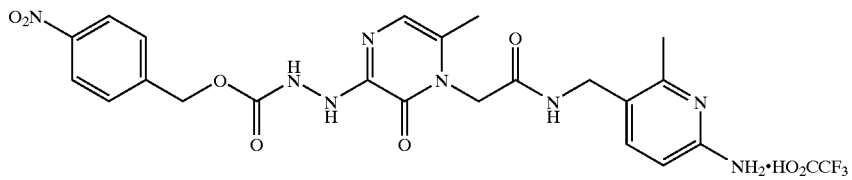

The title compound was prepared from the compound of Example 9 (70 mg, 0.15 mmol) and 4-nitrobenzyl chloroformate (33 mg, 0.15 mmol) following the procedure of Example 22 (Step L). ¹H NMR (D₂O) δ2.21 (s, 3H), 2.49 (s, 3H), 4.35 (s, 2H), 4.84 (s, 2H), 5.35 (s, 2H), 6.70–6.90 (m, 2H), 7.60–7.75 (m, 2H), 7.80 (d, J=8.8 Hz, 1H), 8.20–8.40 (m, 2H). MS (m/z) 497.0 (M+1). RP-HPLC $R_t$ 11.5 minutes (water/ACN/TFA, 0 to 50%, 0.1% TFA, 20 minutes).

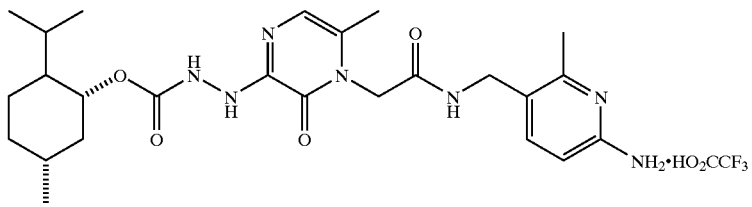

Example 40

Preparation of 1-[5-(2-amino-6-methylpyridyl)methylcarboxamidomethyl]-3-[2-(4-methoxybenzylcarbamyl)hydrazino]-6-methylpyrazinone Hydrotrifluoroacetate

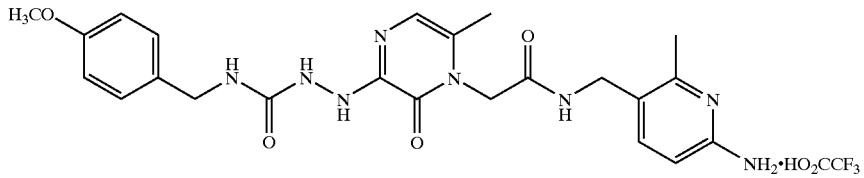

The title compound was prepared from the compound of Example 9 (50 mg, 0.11 mmol) and 4-methoxybenzyl isocyanate (0.016 mL, 0.11 mmol) following the procedure of Example 22 (Step L). $^1$H NMR (D$_2$O) δ2.22 (s, 3H), 2.50 (s, 3H), 3.85 (s, 3H), 4.33 (s, 2H), 4.36 (s, 2H), 4.85 (s, 2H), 6.83 (s, 1H), 6.85 (d, J=9.2 Hz, 1H), 7.01 (d, J=8.8 Hz, 2H), 7.29 (d, J=8.8 Hz, 2H), 7.81 (d, J=9.2 Hz, 1H). MS (m/z) 481 (M+1). RP-HPLC R$_t$ 10.3 minutes (water/ACN/TFA, 0 to 50%, 0.1% TFA, 20 minutes).

Example 41

Preparation of 1-[5-(2-amino-6-methylpyridyl)methylcarboxamidomethyl]-6-methyl-3-[2-(2-methylbenzylcarbamyl)hydrazino]pyrazinone, Hydrotrifluoroacetate

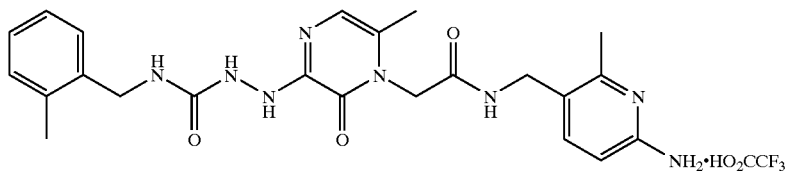

The title compound was prepared from the compound of Example 9 (50 mg, 0.11 mmol) and 2-methylbenzyl isocyanate (16 mg, 0.11 mmol) following the procedure of Example 22 (Step L). $^1$H NMR (D$_2$O) δ2.23 (s, 3H), 2.32 (s, 3H), 2.49 (s, 3H), 4.35 (s, 2H), 4.39 (s, 2H), 4.86 (s, 2H), 6.82 (s, 1H), 6.85 (d, J=9.2 Hz, 1H), 7.20–7.35 (m, 4H), 7.81 (d, J=9.2 Hz, 1H). MS (m/z) 465 (M+1). RP-HPLC R$_t$ 10.8 minutes (water/ACN/TFA, 0 to 50%, 0.1% TFA, 20 minutes).

Example 42

Preparation of 1-[5-(2-amino-6-methylpyridyl)methylcarboxamidomethyl]-6-methyl-3-[2-((R)-1-[1-naphthyl]ethylcarbamyl)hydrazino]pyrazinone, Hydrotrifluoroacetate

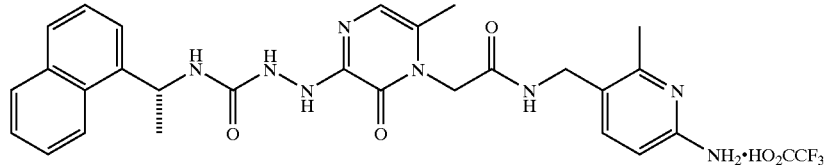

The title compound was prepared from the compound of Example 9 (50 mg, 0.11 mmol) and (R)-1-(1-naphthyl)ethyl isocyanate (0.019 mL, 0.11 mmol) following the procedure of Example 22 (Step L). $^1$H NMR (D$_2$O) δ1.61 (d, J=6.8 Hz, 3H), 2.18 (s, 3H), 2.48 (s, 3H), 4.33 (s, 2H), 5.60–5.70 (m, 1H), 6.77 (s, 1H), 6.83 (d, J=9.2 Hz, 1H), 7.50–7.70 (m, 4H), 7.79 (d, J=8.8 Hz, 1H), 7.89 (d, J=7.6 Hz, 1H), 8.00 (J=8.0 Hz, 1H), 8.18 (d, J=8.1 Hz, 1H). MS (m/z) 515 (M+1). RP-HPLC R$_t$ 13.4 minutes (water/ACN/TFA, 0 to 50%, 0.1% TFA, 20 minutes).

Example 43

Preparation of 1-[5-(2-amino-6-methylpyridyl)methylcarboxamidomethyl]-6-methyl-3-[2-(3-trifluoromethylbenzylcarbamyl)hydrazino]pyrazinone, Hydrotrifluoroacetate

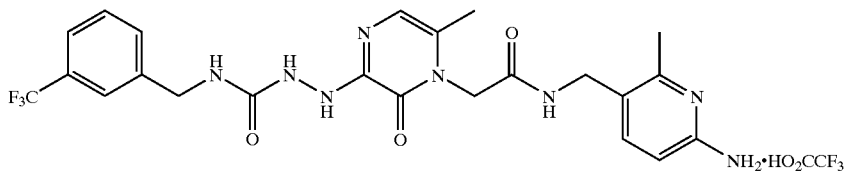

The title compound was prepared from the compound of Example 9 (70 mg, 0.15 mmol) and 3-trifluoromethylbenzylamine (0.024 mL, 0.15 mmol) following the procedure of Example 37 (Step L). $^1$H NMR (D$_2$O) δ2.21 (s, 3H), 2.49 (s, 3H), 4.35 (s, 2H), 4.45 (s, 2H), 4.85 (s, 2H), 6.80–6.90 (m, 2H), 7.50–7.70 (m, 4H), 7.81 (d, J=9.2 Hz, 1H). MS (m/z) 519 (M+1). RP-HPLC R$_t$ 12.5 minutes (water/ACN/TFA, 0 to 50%, 0.1% TFA, 20 minutes).

Example 44

Preparation of 1-[5-(2-amino-6-methylpyridyl)methylcarboxamidomethyl]-6-methyl-3-[2-(4-trifluoromethylbenzylcarbamyl)hydrazino]pyrazinone, Hydrotrifluoroacetate

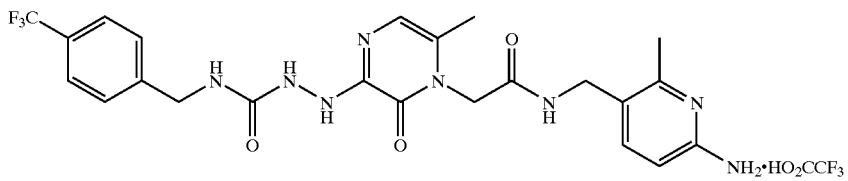

The title compound was prepared from the compound of Example 9 (70 mg, 0.15 mmol) and 4-trifluoromethylbenzylamine (0.023 mL, 0.15 mmol) following the procedure of Example 37 (Step L). $^1$H NMR (D$_2$O) δ2.21 (s, 3H), 2.50 (s, 3H), 4.36 (s, 2H), 4.46 (s, 2H), 4.85 (s, 2H), 6.80–6.90 (m, 2H), 7.47 (d, J=8.0 Hz, 2H), 7.71 (d, J=8.0 Hz, 2H), 7.81 (d, J=9.2 Hz, 1H). MS (m/z) 519 (M+1). RP-HPLC R$_t$ 12.7 minutes (water/ACN/TFA, 0 to 50%, 0.1% TFA, 20 minutes).

Example 45

Preparation of 1-[5-(2-amino-6-methylpyridyl)methylcarboxamidomethyl]-6-methyl-3-[2-(2-trifluoromethylbenzenesulfonyl)hydrazino]pyrazinone, Hydrotrifluoroacetate

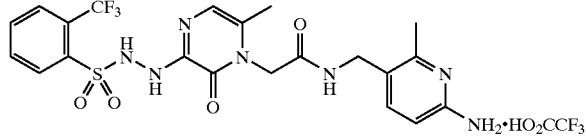

The title compound was prepared from the compound of Example 9 (140 mg, 0.31 mmol) and 2-trifluoromethylbenzenesulfonyl chloride (0.06 mL, 0.37 mmol) following the procedure of Example 22 (Step L). $^1$H NMR (D$_2$O) δ2.14 (s, 3H), 2.49 (s, 3H), 4.34 (s, 2H), 4.77 (s, 2H), 6.69 (s, 1H), 6.84 (d, J=9.2 Hz, 1H), 7.75–7.90 (m, 3H), 8.05 (d, J=8.8 Hz, 1H), 8.15 (d, J=7.6 Hz, 1H); MS (m/z) 526 (M+1). RP-HPLC R$_t$ 12.5 minutes (water/ACN/TFA, 0 to 50%, 0.1% TFA, 20 minutes).

Example 46

Preparation of 1-[5-(2-amino-6-methylpyridyl)methylcarboxamidomethyl]-3-[2-(2-fluorobenzylcarbamyl)hydrazino]-6-methylpyrazinone, Hydrotrifluoroacetate

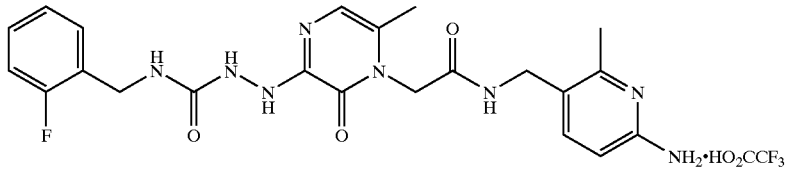

The title compound was prepared from the compound of Example 9 (50 mg, 0.11 mmol) and 2-fluorobenzylamine (0.014 mL, 0.12 mmol) following the procedure of Example 37 (Step L). $^1$H NMR (D$_2$O) δ2.20 (s, 3H), 2.50 (s, 3H) 4.35 (s, 2H), 4.43 (s, 2H), 4.84 (s, 2H), 6.80–6.90 (m, 2H), 7.10–7.30 (m, 2H), 7.35–7.40 (m, 2H), 7.81 (d, J=8.4 Hz, 1H). MS (m/z) 469 (M+1). RP-HPLC R$_t$ 9.9 minutes (water/ACN/TFA, 0 to 50%, 0.1% TFA, 20 minutes).

Example 47

Preparation of 1-[5-(2-amino-6-methylpyridyl)methylcarboxamidomethyl]-6-methyl-3-[2-(2-trifluoromethylbenzylcarbamyl)hydrazino]pyrazinone, Hydrotrifluoroacetate

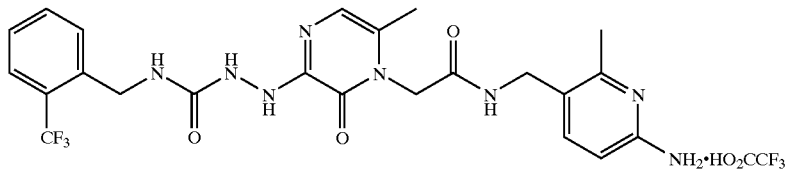

The title compound was prepared from the compound of Example 9 (50 mg, 0.11 mmol) and 2-trifluoromethylbenzylamine (0.017 mL, 0.12 mmol) following the procedure of Example 37 (Step L). $^1$H NMR (D$_2$O) δ2.19 (s, 3H), 2.50 (s, 3H), 4.30 (s, 2H), 4.57 (s, 2H), 4.73 (s, 2H), 6.80 (s, 1H), 6.81 (d, J=9.2 Hz, 1H), 7.40 (t, J=8.2 Hz, 1H), 7.58 (t, J=8.2 Hz, 1H), 7.62–7.70 (m, 2H), 7.85 (d, J=9.2 Hz, 1H). MS (m/z) 519 (M+1). RP-HPLC R$_t$ 12.0 minutes (water/ACN/TFA, 0 to 50%, 0.1% TFA, 20 minutes).

Example 48

Preparation of 1-[5-(2-amino-6-methylpyridyl)methylcarboxamidomethyl]-3-[2-(2-methoxybenzylcarbamyl)hydrazino]-6-methylpyrazinone, Hydrotrifluoroacetate

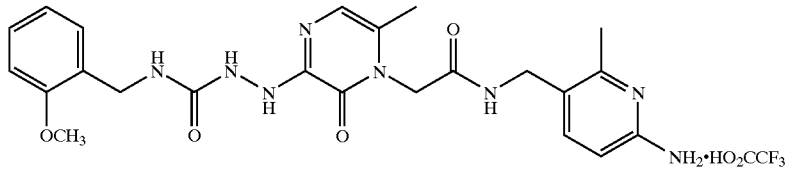

The title compound was prepared from the compound of Example 9 (50 mg, 0.11 mmol) and 2-methoxybenzylamine (0.016 mL, 0.12 mmol) following the procedure of Example 37 (Step L). 1H NMR (D$_2$O) δ2.21 (s, 3H), 2.50 (s, 3H), 3.83 (s, 3H), 4.36 (s, 2H), 4.85 (s, 2H), 6.81 (s, 1H), 6.85 (d, J=9.2 Hz, 1H), 7.00–7.10 (m, 2H), 7.29 (d, 1H), 7.37 (t, 1H), 7.81 (d, J=8.8 Hz, 1H). MS (m/z) 481 (M+1). RP-HPLC R$_t$ 10.2 minutes (water/ACN/TFA, 0 to 50%, 0.1% TFA, 20 minutes).

Example 49

Preparation of 1-[5-(2-amino-6-methylpyridyl)methylcarboxamidomethyl]-6-methyl-3-(2-piperonylcarbamylhydrazino)pyrazinone, Hydrotrifluoroacetate

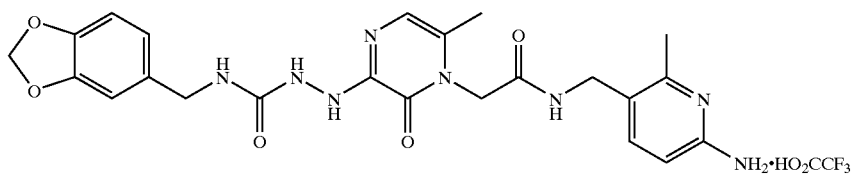

The title compound was prepared from the compound of Example 9 (70 mg, 0.15 mmol) and piperonylamine (0.021 mL, 0.17 mmol) following the procedure of Example 37 (Step L). $^1$H NMR (D$_2$O) δ2.21 (s, 3H), 2.50 (s, 3H), 4.29 (s, 2H), 4.35 (s, 2H), 4.85 (s, 2H), 5.98 (s, 2H), 6.80–6.92 (m, 5H), 7.81 (d, J=9.2 Hz, 1H). MS (m/z) 495 (M+1). RP-HPLC R$_t$ 9.6 minutes (water/ACN/TFA, 0 to 50%, 0.1% TFA, 20 minutes).

Example 50

Preparation of 1-[5-(2-amino-6-methylpyridyl)methylcarboxamidomethyl]-6-methyl-3-[2-(3,3-dimethylbutylcarbamyl)hydrazino]pyrazinone, Hydrotrifluoroacetate

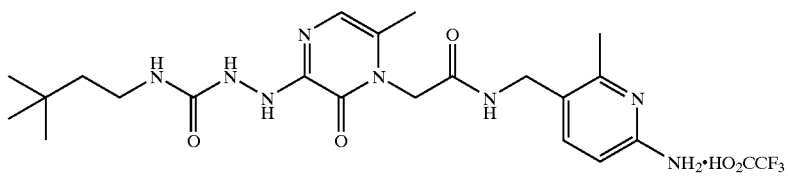

The title compound was prepared from the compound of Example 9 (70 mg, 0.15 mmol) and 3,3-dimethylbutylamine (0.023 mL, 0.165 mmol) following the procedure of Example 37 (Step L). $^1$H NMR (D$_2$O) δ0.91 (s, 9H), 1.41 (dd, 2H), 2.21 (s, 3H), 2.50 (s, 3H), 3.21 (dd, 2H), 4.36 (s, 2H), 4.86 (s, 2H), 6.82 (s, 2H), 6.85 (d, J=9.2 Hz, 1H), 7.82 (d, J=9.2 Hz, 1H). MS (m/z) 445 (M+1). RP-HPLC R$_t$ 11.1 minutes (water/ACN/TFA, 0 to 50%, 0.1% TFA, 20 minutes).

Example 51

Preparation of 1-[5-(2-amino-6-methylpyridyl)methylcarboxamidomethyl]-3-[2-(3-iodobenzylcarbamyl)hydrazino]-6-methylpyrazinone, Hydrotrifluoroacetate

The title compound was prepared from the compound of Example 9 (70 mg, 0.15 mmol) and 3-iodobenzylamine (0.023 mL, 0.17 mmol) following the procedure of Example 37 (Step L). $^1$H NMR (D$_2$O) δ2.21 (s, 3H), 2.49 (s, 3H), 4.34 (s, 2H), 4.35 (s, 2H), 4.85 (s, 2H), 6.84 (d, J=9.2 Hz, 1H), 6.94 (s, 1H), 7.16 (t, 1H), 7.30 (d, J=7.2 Hz, 1H), 7.75 (s, 1H), 7.70 (d, J=8.0 Hz, 1H), 7.81 (d, J=9.2 Hz, 1H). MS (m/z) 577 (M+1). RP-HPLC R$_t$ 12.1 minutes (water/ACN/TFA, 0 to 50%, 0.1% TFA, 20 minutes).

Example 52

Preparation of 1-[5-(2-amino-6-methylpyridyl)methylcarboxamidomethyl]-6-methyl-3-[2-(propargylcarbamyl)hydrazino]pyrazinone, Hydrotrifluoroacetate

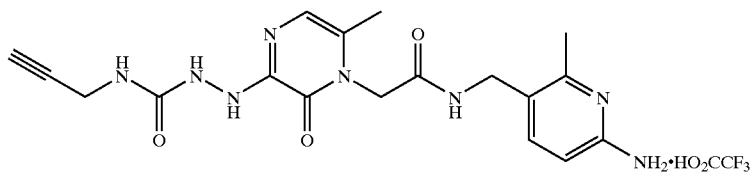

The title compound was prepared from the compound of Example 9 (20 mg, 0.15 mmol) and propargylamine (0.012 mL, 0.165 mmol) following the procedure of Example 37 (Step L). $^1$H NMR (D$_2$O) δ2.23 (s, 3H), 2.50 (s, 3H), 2.63 (s, 1H), 3.97 (s, 2H), 4.37 (s, 2H), 4.87 (s, 2H), 6.82 (s, 1H), 6.86 (d, J=9.2 Hz, 1H), 7.82 (d, J=9.2 Hz, 1H). MS (m/z) 399 (M+1). RP-HPLC R$_t$ 6.7 minutes (water/ACN/TFA, 0 to 50%, 0.1% TFA, 20 minutes).

Example 53

Preparation of 1-[5-(2-amino-6-methylpyridyl)methylcarboxamidomethyl]-3-[2-(2-chlorobenzenesulfonyl)hydrazino]-6-methyl Pyrazinone, Hydrotrifluoroacetate

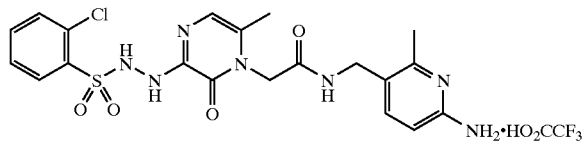

The title compound was prepared from the compound of Example 9 (50 mg, 0.11 mmol) and 2-chlorobenzenebenzenesulfonyl chloride (54 mg, 0.22 mmol) following the procedure of Example 22 (Step L). $^1$H NMR (D$_2$O) δ2.20 (s, 3H), 2.48 (s, 3H), 4.33 (s, 2H), 6.79 (s, 1H), 6.82 (d, J=9.2 Hz, 1H), 7.50–7.60 (m, 1H), 7.70–7.76 (m, 2H), 7.78 (d, J=9.2 Hz, 1H), 8.06 (d, 1H). MS (m/z) 493 (M+1). RP-HPLC R$_t$ 10.9 minutes (water/ACN/TFA, 0 to 50%, 0.1% TFA, 20 minutes).

Example 54

Preparation of 1-[5-(2-amino-6-methylpyridyl)methylcarboxamidomethyl]-3-[2-(2-fluorobenzenesulfonyl)hydrazino]-6-methyl Pyrazinone, Hydrotrifluoroacetate

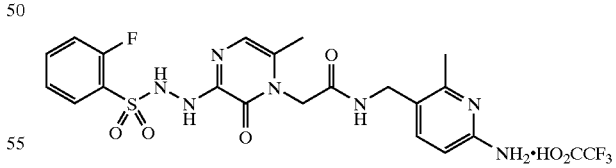

The title compound was prepared from the compound of Example 9 (140 mg, 0.31 mmol) and 2-fluorobenzenebenzenesulfonyl chloride (72 mg, 0.37 mmol) following the procedure of Example 22 (Step L). $^1$H NMR (D$_2$O) δ2.20 (s, 3H), 2.49 (s, 3H), 4.34 (s, 2H), 6.77 (s, 1H), 6.84 (d, J=8.8 Hz, 1H), 7.35–7.45 (m, 2H), 7.75–7.90 (m, 3H). MS (m/z) 476 (M+1). RP-HPLC R$_t$ 10.1 minutes (water/ACN/TFA, 0 to 50%, 0.1% TFA, 20 minutes).

Example 55

Preparation of 1-[5-(2-amino-6-methylpyridyl)methylcarboxamidomethyl]-3-[2-(4-chlorobenzenesulfonyl)hydrazino]-6-methylpyrazinone, Hydrotrifluoroacetate

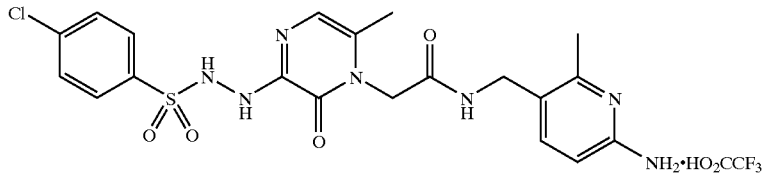

The title compound was prepared from the compound of Example 9 (70 mg, 0.15 mmol) and 4-chlorobenzenebenzenesulfonyl chloride (33 mg, 0.16 mmol) following the procedure of Example 22 (Step L). $^1$H NMR (D$_2$O) δ2.14 (s, 3H), 2.49 (s, 3H), 4.34 (s, 2H), 4.77 (s, 2H), 6.58 (s, 1H), 6.84 (d, J=9.2 Hz, 1H), 7.60 (d, J=8.4 Hz, 2H), 7.81 (d, J=9.2 Hz, 1H), 7.86 (d, J=8.4 Hz, 2H). MS (m/z) 493 (M+1). RP-HPLC R$_t$ 11.9 minutes (water/ACN/TFA, 0 to 50%, 0.1% TFA, 20 minutes).

Example 56

Preparation of 1-[5-(2-amino-6-methylpyridyl)methylcarboxamidomethyl]-3-[2-(3,5-difluorobenzyloxycarbonyl)hydrazino]-6-methylpyrazinone, Hydrotrifluoroacetate

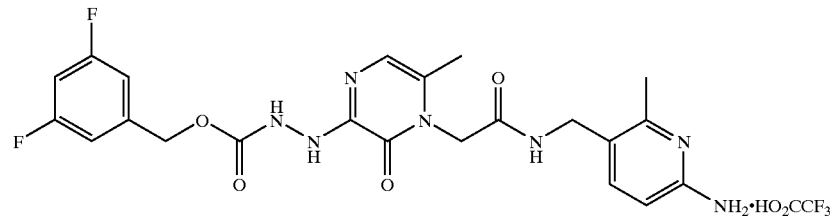

The title compound was prepared from the compound of Example 9 (100 mg, 0.22 mmol) and 3,5-difluorobenzyl alcohol (0.027 mL, 0.24 mmol) following the procedure of Example 37 (Step L). $^1$H NMR (DMSO-d$_6$) δ2.07 (s, 3H), 2.43 (s, 3H), 4.17 (s, 2H), 4.62 (s, 2H), 5.13 (s, 2H), 6.67 (s, 1H), 6.80 (d, J=8.8 Hz, 1H), 7.10–7.30 (m, 3H), 7.65 (br s, 1H), 7.78 (d, J=8.8 Hz, 1H), 8.76 (br s, 2H). MS (m/z) 488 (M+1). RP-HPLC R$_t$ 11.9 minutes (water/ACN/TFA, 0 to 50%, 0.1% TFA, 20 minutes).

Example 57

Preparation of 1-(2-Amino-6-methyl-5-methylcarboxamidomethyl pyridinyl)-3-(4-methoxybenzylcarbamoyl)hydrazino-6-methylpyrazinone Trifluoroacetate

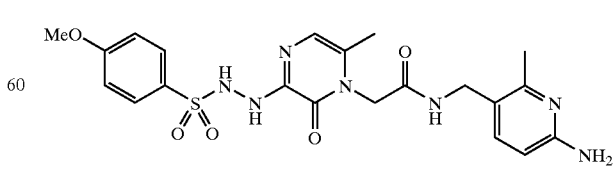

The title compound was prepared as the TFA salt from the compound of Example 9 (70 mg, 0.15 mmol) and 4-methoxy benzenesulfonyl chloride (32 mg, 0.154 mmol) using the procedure of Example 22 (Step L). $^1$H NMR (D$_2$O) δ2.14 (s, 3H), 2.49 (s, 3H), 3.91 (s, 3H), 4.34 (s, 2H), 4.77 (s, 2H), 6.69 (s, 1H), 6.83 (d, J=9.2 Hz, 1H), 7.11 (d, J=8.8 Hz, 2H), 7.80 (d, J=8.8 Hz, 1H), 7.85 (d, J=8.8 Hz, 2H); MS (m/z) 488 (M+1); RP-HPLC R$_t$ 10.2 minutes (water/ACN/TFA 0.01% TFP, gradient 0 to 50%, 20 minutes).

VII. Preparation of Compounds According to FIG. 2 (Examples 58 to 60)

Example 58

Preparation of 1-[5-(2-amino-6-methylpyridyl) methylcarboxamidomethyl]-3-[2-ethyl-2- (propargyloxycarbonyl)hydrazino]-6- methylpyrazinone, Hydrotrifluoroacetate (Step M, FIG. 2)

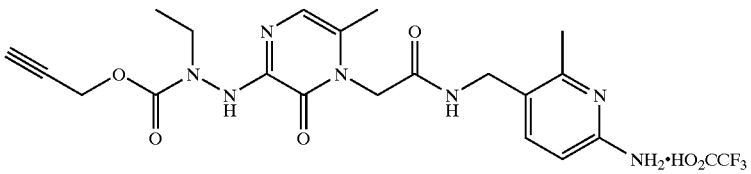

To a solution of the compound of Example 9 (Step J) (110 mg, 0.24 mmol) in MeOH (7 mL), were added acetaldehyde (14.5 μL, 0.26 mmol), AcOH (16 μL, 0.29 mmol), and sodium cyanoborohydride (30 mg, 0.48 mmol). The resulting solution was stirred at room temperature for 1 hour, then concentrated in vacuo. The crude residue was diluted with EtOAc (40 mL), washed with saturated aqueous NaHCO$_3$ (40 mL) and brine (40 mL), dried (Na$_2$SO$_4$), and concentrated in vacuo.

The crude ethyl hydrazine intermediate was diluted with dry THF (9 mL); then Et$_3$N (84 μL, 0.60 mmol) was added, followed by propargyl chloroformate (35 μL, 0.36 mmol). The resulting mixture was stirred at room temperature for 2 hours, then concentrated in vacuo. The crude residue was diluted with DCM (4 mL) and TFA (4 mL) was added. This clear solution was stirred at room temperature for 1 hour, then was concentrated in vacuo. The crude residue was purified by preparative RP-HPLC (water/ACN/TFA) to afford the title compound (30 mg) as a white solid. $^1$H NMR (D$_2$O) δ1.20 (t, J=6.8 Hz, 3H), 2.22 (s, 3H), 2.51 (s, 3H), 2.95 (s, 1H), 3.65 (br s, 2H), 4.37 (s, 2H), 4.86 (s, 2H), 6.81 (s, 1H), 6.86 (d, J=9.2 Hz, 1H), 7.82 (d, J=9.2 Hz, 1H). MS (m/z) 428 (M+1). RP-HPLC R$_t$ 9.4 minutes (water/ACN/ TFA, 0 to 50%, 0.1% TFA, 20 minutes).

Example 59

Preparation of 1-[5-(2-amino-6-methylpyridyl) methylcarboxamidomethyl]-6-methyl-3-[2-methyl-2- (propargyloxycarbonyl)hydrazino]pyrazinone, Hydrotrifluoroacetate

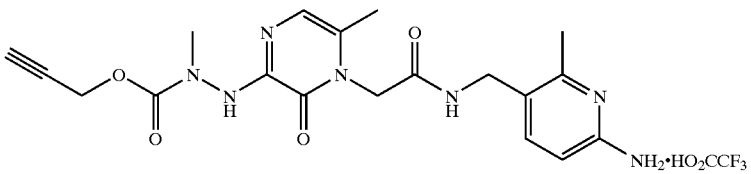

The title compound was prepared from the compound of Example 9 (70 mg, 0.15 mmol), formaldehyde (0.011 mL, 0.15 mmol), and propargyl chloroformate (0.035 mL, 0.36 mmol) following the procedure of Example 58 (Step M). $^1$H NMR (D$_2$O) δ2.21 (s, 3H), 2.50 (s, 3H), 2.97 (s, 1H), 3.24 (s, 3H), 4.36 (s, 2H), 4.84 (s, 2H), 6.85 (s, 1H), 6.86 (d, J=8.8 Hz, 1H), 7.82 (d, J=8.8 Hz, 1H). MS (m/z) 414 (M+1). RP-HPLC R$_t$ 8.56 minutes (water/ACN/TFA, 0 to 50%, 0.1% TFA, 20 minutes).

Example 60

Preparation of 1-[5-(2-amino-6-methylpyridyl) methylcarboxamidomethyl]-6-methyl-3-[2,2-di(2-phenylethyl)hydrazino]pyrazinone, Hydrotrifluoroacetate (Step N, FIG. 2)

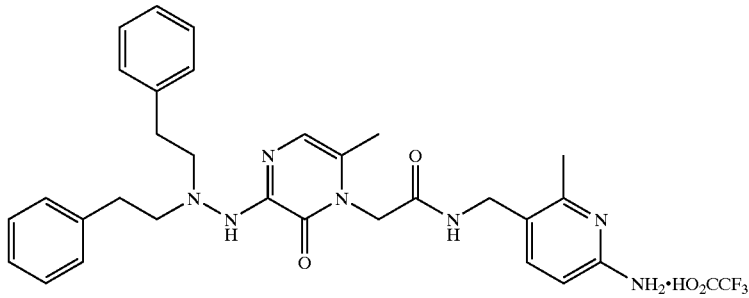

To a solution of the compound of Example 9 (110 mg, 0.24 mmol) in MeOH (7 mL), were added phenylacetaldehyde (31 μL, 0.26 mmol), AcOH (16 μL, 0.29 mmol), and sodium cyanoborohydride (30 mg, 0.48 mmol). The resulting solution was stirred at room temperature for 1 hour, then concentrated in vacuo. The crude residue was diluted with DCM (4 mL) and TFA (4 mL). This clear solution was stirred at room temperature for 1 hour, then was concentrated in vacuo. The crude residue was purified by preparative RP-HPLC (water/ACN/TFA) to afford the title compound (45 mg) as a white solid. $^1$H NMR (D$_2$O) δ2.17 (s, 3H), 2.51 (s, 3H), 2.80–2.90 (m, 4H), 3.20–3.45 (m, 4H), 4.36 (s, 2H), 4.86 (s, 2H), 6.41 (s, 1H), 6.87 (d, J=9.0 Hz, 1H), 7.10–7.35 (m, 10H), 7.81 (d, J=9.0 Hz, 1H). MS (m/z) 526 (M+1). RP-HPLC R$_t$ 14.2 minutes (water/ACN/TFA, 0 to 50%, 0.1% TFA, 20 minutes).

VIII. Preparation of Intermediates for Incorporation as P1 Groups

Example 61

Preparation of 3-(Hydroxymethyl)-6-methylaniline (4-2)

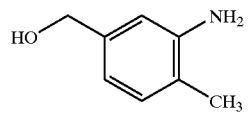

A solution of 3-nitro-4-methylbenzyl alcohol (20 g, 120.0 mmol) (4-1) in ethyl acetate (500 mL) was stirred at room temperature, while 10% Pd/C (1.0 g) was added in one portion. The resulting suspension was hydrogenated (10 psi) at room temperature under a hydrogen-filled balloon for 48 hours. The catalyst was removed by filtration, and solvent was evaporated under vacuum to give an 1:1 mixture (16.1 g) of the title compound (51%) and a by-product, 2,5-dimethylaniline. This mixture was used in the procedure of Example 62 without further separation. The by-product is removed during the flash column chromatography step of Example 62. For the title compound: MS (electrospray) 138 (M+1); $^1$H N MR (CD$_3$OD) δ2.14 (s, 3H), 4.54 (s, 2H), 7.12 (d, 1H, J=7.6 Hz), 7.19 (d, 1H, J=7.6 Hz), 7.30 (s, 1H).

Use of a high pressure (30 Psi) of hydrogen or use of alcohol as a solvent in the hydrogenation step led almost exclusively to 2,5-dimethylaniline as a hydrogenation product, in high yield (99%). MS (electrospray) 122 (M+1); $^1$H N MR (CD$_3$OD) δ2.13 (s, 3H), 2.46 (s, 3H), 6.62 (d, 1H, J=7.6 Hz), 6.72 (d, 1H, J=7.6 Hz), 6.94 (s, 1H).

Example 62

Preparation of 3-(hydroxymethyl)-6-methyl-N-(methylcarbonyl)aniline (4-3)

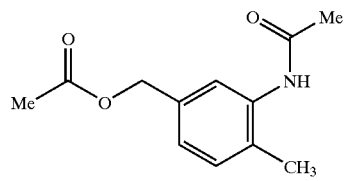

To a solution of an approximately 1:1 mixture of 3-(hydroxymethyl)-6-methylaniline, (8.05 g, 58.8 mmol) (2) and 2,5-dimethylaniline in chloroform (290 mL), was added acetic anhydride (20 mL, 206 mmol) and potassium acetate (20 g, 202 mmol). The resulting mixture was heated to its reflux temperature for 2 hours. The mixture was then concentrated and purified by a flash column chromatography (1:1 of hexane-ethyl acetate) which also removed the by-product from Example 61 to give the title compound (12.02 g, 92%). TLC Rf: 0.52 (ethyl acetate); MS (electrospray) 222 (M+1); $^1$H N MR (CDCl$_3$) δ2.09 (s, 3H), 2.21 (s, 3H), 2.25 (s, 3H), 5.06 (s, 2H), 7.00 (br s, 1H, NH), 7.08 (d, 1H, J=7.6 Hz), 7.18 (d, 1H, J=7.6 Hz), 7.81 (s, 1H).

Example 63

Preparation of 1-Acetyl-6-(acetoxymethyl)indazole (4-4)

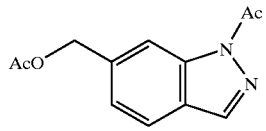

To a suspension of 3-(hydroxymethyl)-6-methyl-N-(methylcarbonyl)aniline (10.0 g, 45 mmol) (4-3) and potassium acetate (8.6 g, 88 mmol) in chloroform (300 mL), was added acetic anhydride (8.3 mL, 88 mmol), isoamylnitrite (35 mL, 300 mmol) and 18-crown-6 (1.5 g, 0.6 mmol) at room temperature. The reaction mixture was heated at its reflux temperature for 28 hours. The reaction mixture was diluted with methylene chloride (600 mL) and washed with saturated NaHCO$_3$ aqueous solution (300 mL), water (300 mL) and brine (50 mL). After drying (Na$_2$SO$_4$), the organic solvent was removed under vacuum to give a yellow oil which was purified by a flash chromatography on silica gel (85:15 hexane-ethyl acetate) to yield the title compound (10.01 g, 95%). TLC Rf 0.47 (70:30 of hexane-ethyl acetate); MS (electrospray) 233 (M+1); $^1$H N MR (CDCl$_3$) δ2.10 (s, 3H), 2.78 (s, 3H), 5.27 (s, 2H), 7.36 (d, 1H, J=8.0 Hz), 7.73 (d, 1H, J=8.0 Hz), 8.12 (s, 1H), 8.47 (s, 1H).

Example 64

Preparation of 6-(Bromomethyl)-1H-indazole Hydrogen Bromide (4-5)

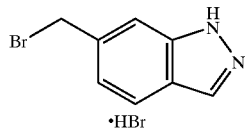

A suspension of 1-acetyl-6-(acetoxymethyl)indazole (9.5 g, 41 mmol) (4-4) in aqueous hydrobromic acid (48% aqueous solution, 20 mL, 177 mmol) was stirred at room temperature for 46 hours. The solid was collected on a Buchner funnel and dried under vacuum for 12 hours. The filtrate was stirred at room temperature for additional 24 hours and more solid was collected. After drying under vacuum, title compound was obtained as a yellow solid (10.0 g, 84%) which was used as such without further purification. MS (electrospray) 211 (M+1 for $^{79}$Br), 213 (M+1 for $^{81}$Br); $^1$H N MR (CDCl$_3$) δ4.85 (s, 2H), 7.65 (d, 1H, J=8.4 Hz), 7.78 (d, 1H, J=8.4 Hz), 8.05 (s, 1H), 8.10 (s, 1H).

Example 65

Preparation of 6-(bromomethyl)-1-(2-tetrahydropyranyl)indazole (4-6)

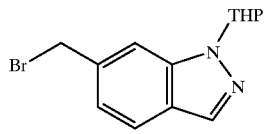

A yellow suspension of 6-(bromomethyl)-1H-indazole hydrogen bromide (9.0 g, 43 mmol) (4-5) and 3,4-dihydro-2H-pyran (7.2 g, 86 mmol) in THF (200 mL) was heated at its reflux temperature for 2 hours. After cooling down to room temperature, the reaction mixture was stirred at room temperature for 12 hours under nitrogen. The reaction solution was diluted with methylene chloride (500 mL), washed with saturated NaHCO$_3$, water and brine. After drying (MgSO$_4$), the solvent was removed under vacuum to give a yellow oil. Flash chromatography yielded the title compound (6.6 g, 72%). TLC Rf 0.52 (80:20 of hexane-ethyl acetate); MS (electrospray) 295, 297 (M+1); $^1$H N MR (CDCl$_3$) δ1.57–1.84 (m, 3H), 2.16 (m, 2H), 2.55 (m, 1H), 3.75 (m, 1H), 4.01 (m, 1H), 4.65 (s, 2H), 5.71 (d, 1H, J=9.2 Hz), 7.44 (d, 1H, J=8.8 Hz), 7.59 (d, 1H, J=8.8 Hz), 7.73 (s, 1H), 8.00 (s, 1H).

Example 66

Preparation of 6-(Azidomethyl)-1-(2-tetrahydropyranyl)indazole (4-7)

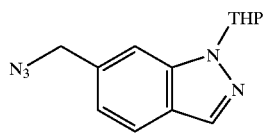

To a solution of 6-(bromomethyl)-1-(2-tetrahydropyranyl)indazole (4.0 g, 14 mmol) (6) in DMF (30 mL) was added sodium azide (6 g, 92 mmol) in one portion. The suspension was heated at 90° C. for 30 minutes and a yellow solution was formed. After cooling down to room temperature, the reaction mixture was poured into water (100 mL) and extracted with ether (2×150 mL). Combined organic layers were washed with brine then dried (MgSO$_4$). Evaporation of solvent gave an yellow oil which was purified by column chromatography to yield title compound (2.91 g, 83%). TLC Rf 0.31 (70:30 of hexane-ethyl acetate); MS (electrospray) 258 (M+1); $^1$H NMR (CDCl$_3$) δ1.75 (m, 3H), 2.10 (m, 2H), 2.55 (m, 1H), 3.72 (m, 1H), 4.01 (m, 1H), 4.48 (s, 2H), 5.73 (dd, 1H, J=8.2, 2.8 Hz), 7.12 (dd, 1H, J=8.2, 0.8 Hz), 7.55 (s, 1H), 7.71 (d, 1H, J=8.2 Hz), 8.02 (s, 1H).

Example 67

Preparation of 6-(Aminomethyl)-1-(2-tetrahydropyranyl)indazole (4-8)

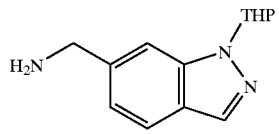

A solution of LiAlH$_4$ (9 mL, 9 mmol, 1.0 M) in THF was added dropwise to a yellow solution of 6-(azidomethyl)-1-(2-tetrahydropyranyl)indazole (2.4 g, 9 mmol) (4-7) in THF (30 mL) at 0° C. The addition time was 10 minutes, and gas came out. After stirring at 0° C. for 1 hour, NaOH (1.0 m, 1.5 mL) was added. The reaction mixture was allowed to warm to room temperature. Ethyl acetate (100 mL) was added, and the suspension was filtered through (Celite). The filter cake was washed with an addition portion of ethyl acetate (40 mL). Combined organic layers were evaporated under vacuum to five essentially pure amine (2.1 g, 97%). MS (electrospray) 232.5 (M+1); $^1$H NMR (CDCl$_3$) δ1.67 (m, 3H), 2.01 (m, 2H), 2.48 (m, 1H), 3.85 (m, 1H), 3.94 (m, 1H), 5.75 (d, 1H, J=9.4 Hz), 7.14 (d, 1H, J=8.4 Hz), 7.62 (s, 1H), 7.62 (d, 1H, J=8.4 Hz), 7.93 (s, 1H).

Example 68
Preparation of (5-2)

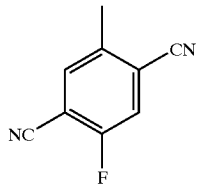

To a solution of 2,5-dibromo-4-fluorotoluene (5-1) (Aldrich, 50.00 g, 186.6 mmol) in DMF (100 mL) was added CuCN (Aldrich, 33.40 g, 373.2 mmol) and the mixture was refluxed under nitrogen for 6 hours. After cooling to room temperature, the mixture was partitioned between 10% KCN water solution and ether. The water layer was extracted with ether, and the combined extracts were washed by brine twice and dried over Na$_2$SO$_4$. After filtration and evaporation, the crude product was purified on a silica gel column eluting with hexane-EtOAc (from 95:5 to 90:10) to provide the title compound as a yellow-green solid (22.66 g, 76% yield). TLC R$_f$ 0.63 (hexane: EtOAc 4:1); m.p. 141–143° C.; $^1$H NMR (400 MHz, CDCl$_3$): δ7.60 (d, 1H, J 6.1 Hz), 7.47 (d, 1H, J 8.2 Hz), 2.58 (s, 3H).

Example 69
Preparation of (5-3)

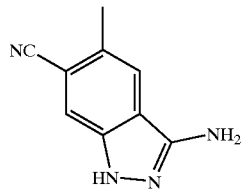

A mixture of 2,5-dicyano-4-fluorotoluene (compound 5-2, 10.95 g, 68.4 mmol) and anhydrous hydrazine (4.5 mL, 143.6 mmol) in anhydrous ethanol (342 mL) was refluxed under nitrogen for 17 hours. After cooling down to the room temperature, a yellow crystalline solid product precipitated out. The solid was filtered, washed by ethanol, and dried under high vacuum to provide yellow crystalline product (4.26 g). The filtrate was evaporated and purified on a silica gel column eluting with dichloromethane and 5% methanol in dichloromethane to provide additional product (6.47 g). Total 10.73 g of yellow crystalline solid product (5-3) was obtained (91% yield). TLC R$_f$ 0.36 (5% MeOH in CH$_2$Cl$_2$); $^1$H NMR (400 MHz, CDCl$_3$): δ9.05 (bs, 1H), 7.64 (s, 1H), 7.48 (s, 1H), 4.12 (bs, 2H), 2.61 (s, 3H).

Example 70

Preparation of (5-4) and (5-5)

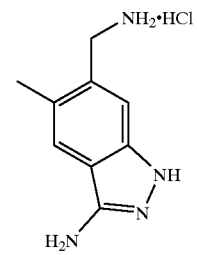

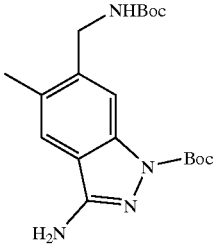

To a solution of 1M borane in THF (40 mL, 40 mmol) was added a solution of compound (5-3) (0.80 g, 4.65 mmol) in anhydrous THF (15 mL) at 0° C. under nitrogen. The reaction mixture was stirred from 0° C. to room temperature under nitrogen for 15 hours. To the reaction solution were added 6N HCl (30 mL) slowly, followed by water (30 mL) and methanol (200 mL). The mixture was stirred at room temperature for 6 hours. Most of THF and methanol were evaporated to give the intermediate (5-4), which was neutralized to pH ~13 by NaOH, and then adjusted to pH ~11 by NaHCO$_3$.

A solution of (Boc) 20 in THF (15 mL, 15 mmol), was added to the above solution of (5-4) in THF and methanol, and the reaction mixture was stirred at room temperature for 15 hours. The product was extracted with dichloromethane, and the combined extracts were washed by brine and dried over Na$_2$SO$_4$. After filtration and evaporation, the product was purified on a silica gel column eluting with 1% and 2% methanol in dichloromethane to provide an off-white product (compound 5-5, 1.05 g, 60% yield). TLC R$_f$ 0.88 (5% MeOH in CH$_2$Cl$_2$); $^1$H NMR (400 MHz, CDCl$_3$): δ7.27 (s, 1H), 7.08 (s, 1H), 5.90 (bs, 2H), 4.76 (bs, 1H), 4.29 (bd, 2H, J 5.8 Hz), 2.25 (s, 3H), 1.62 (s, 9H), 1.46 (s, 9H).

Example 71

Preparation of (5-6)

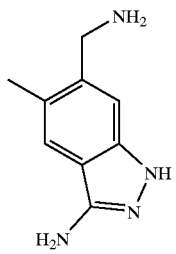

Compound (5-5) (795 mg, 2.11 mmol) was dissolved in 2 M HCl methanol/dioxane (1:1) solution (20 mL). The reaction solution was stirred at room temperature for 4 hours and a lot of white precipitate was formed. After evaporation of solvent, the residue was suspended in methanol (30 mL), and to the mixture was added hydroxide form basic resin (AG 1-X8 Resin from Bio-Rad Laboratories) to make a clear solution and adjust the pH ~11. The resin was filtered and washed with methanol thoroughly. The methanol solution was evaporated and the residue was dried under high vacuum to provide the free amine compound 20 as a white solid (395 mg, 100% yield). $^1$H NMR (400 MHz, CD$_3$OD): $\delta$7.44 (s, 1H), 7.26 (s, 1H), 3.90 (s, 2H), 2.37 (s, 3H), 1.62 (s, 9H).

Example 72

Preparation of (6-2)

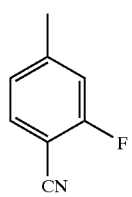

To a solution of 4-bromo-3-fluorotoluene (6-1) (Aldrich, 50.00 g, 264.5 mmol) in DMF (100 mL) was added CuCN (Aldrich, 23.69 g, 264.5 mmol). The mixture was refluxed under nitrogen for 5 hours. After cooling to the room temperature, CuBr precipitated out. The mixture was diluted with ether (500 mL), filtered, and CuBr solid was washed by ether. The combined ether solution was washed with brine three times and dried over MgSO$_4$. After filtration, evaporation and high vacuum dry, an off-white solid product was obtained (32.50 g, 94% yield). TLC R$_f$ 0.54 (hexane:EtOAc 5:1), $^1$H-NMR (400 MHz, CDCl$_3$) $\delta$7.48 (dd, 1H, J 8.2 Hz, J 6.1 Hz), 7.05 (d, 1H, J 8.2 Hz), 7.01 (d, 1H, J 10.1 Hz), 2.42 (s, 3H).

Example 73

Preparation of (6-3)

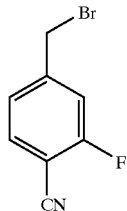

To a solution of 4-cyano-3-fluorotoluene (Compound 6-2), 28.51 g, 211.0 mmol) in carbon tetrachloride (Aldrich, 844 mL) were added NBS (Aldrich, 41.31 g, 162.8 mmol) and AIBN (Aldrich, 2.43 g, 14.8 mmol). The mixture was degassed with nitrogen for three times, and then was refluxed at 85° C. for 4.5 hours. After standing at room temperature overnight, and the mixture was filtered. The solid by-product was washed with CCl$_4$. The filtrate was evaporated and purified on a silica gel column, eluting with hexane-EtOAc (from 20:1 to 5:1). The title product (24.54 g, 54% yield) was obtained as a colorless liquid which solidified after standing at room temperature. TLC R$_f$ 0.44 (hexane:EtOAc 10:1), $^1$H-NMR (400 MHz, CDCl$_3$): $\delta$7.61 (dd, 1H, J 7.9 Hz, J 6.7 Hz), 7.28 (d, 1H, J 6.7 Hz), 7.27 (d, 1H, J 7.0 Hz), 4.44 (s, 2H).

Example 74

Preparation of (6-4)

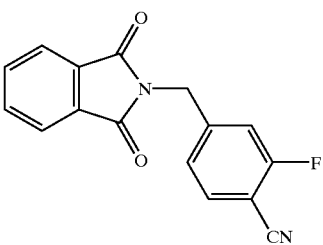

To a solution of α-bromo-4-cyano-3-fluorotoluene (compound 6-3, 7.67 g, 35.83 mmol) in DMF (250 mL) were added phthalimide (Aldrich, 8.74 g, 59.44 mmol) and CS$_2$CO$_3$ (Aldrich, 35.21 g, 108.1 mmol). The reaction mixture was stirred at room temperature under nitrogen for half an hour, and then poured into water (1 L). The product precipitated out of the water solution. After filtration, washing by water (500 mL) and methanol (100 mL), and high vacuum dry, the product was obtained as a white crystalline solid (9.15 g, 91% yield). $^1$H-NMR (400 MHz, CDCl$_3$): $\delta$7.88 (dd, 2H, J 3.05 Hz, J 5.2 Hz), 7.76 (dd, 2H, J 3.05 Hz, J 5.5 Hz), 7.58 (dd, 2H, J 7.9 Hz, J 6.4 Hz), 7.31 (d, 2H, J 7.9 Hz), 7.27 (d, 2H, J 12.5 Hz), 4.87 (s, 2H).

Example 75

Preparation of (6-6)

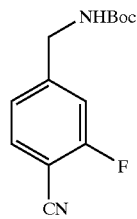

To a solution of compound (6-4) (8.50 g, 30.33 mmol) in n-butanol (Aldrich, 150 mL) was added anhydrous hydrazine (Aldrich, 2.95 mL, 94.02 mmol). The mixture was refluxed under nitrogen for 5 minutes. A voluminous precipitate formed which was removed by filtering out after cooling the mixture to the room temperature. n-Butanol was removed by evaporation. The residue (compound 6-5) was dissolved in dichloromethane; (Boc)$_2$O (7.28 g, 33.36 mmol) was added and the resulting mixture was stirred at room temperature for 1 hour. After evaporation of solvent, the residue was purified on a silica gel column eluting with hexane-EtOAc (from 5:1 to 3:1) to provide compound 6-6 as a white crystalline solid (7.52 g, 99% yield). TLC R$_f$ 0.37 (hexane:EtOAc 3:1), $^1$H-NMR (400 MHz, CDCl$_3$): δ7.57 (dd, 1H, J 7.6 Hz, J 6.7 Hz), 7.16 (d, J 7.6 Hz, 1H), 7.14 (d, 1H, J 9.8 Hz), 5.01 (bs, 1H), 4.36 (bd, 2H, J 5.8 Hz), 1.46 (s, 9H).

Example 76

Preparation of (6-7)

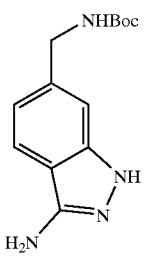

To a solution of compound 6-6 (7.52 g, 30.3 mmol) in n-butanol (150 mL) was added hydrazine (Aldrich, 2.86 mL, 91.0 mmol). The reaction mixture was refluxed under nitrogen for 22 hours. After evaporation of solvent, the residue was purified on a silica gel column eluting with 5% methanol in dichloromethane to provide product compound 6-7 (5.13 g, 64% yield) as a light yellow crystalline solid. TLC R$_f$ 0.33 (5% MeOH in CH$_2$Cl$_2$), $^1$H-NMR (400 MHz, CDCl$_3$) δ8.85 (bs, 1H), 7.51 (d, 1H, J 8.2 Hz), 7.22 (s, 1H), 7.10 (d, 1H, J 8.2 Hz), 4.91 (bs, 1H), 4.41 (bd, 2H, J 5.5 Hz), 4.08 (bs, 2H), 1.47 (s, 9H).

Example 77

Preparation of (6-8)

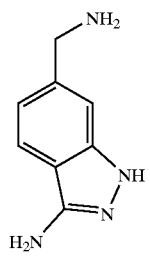

Compound 6-7 (5.13 g, 19.6 mmol) was dissolved in a 2M HCl dioxane solution (60 mL). The reaction mixture was stirred at room temperature for half an hour. After evaporation of solvent, a light yellow solid was obtained which was suspended in methanol (300 mL). To the mixture was added hydroxide form basic resin (AG 1-X8 Resin from Bio-Rad Laboratories) to adjust the pH to ~10. After filtration, the resin was washed by methanol thoroughly. The methanol solution was evaporated and the residue was dried under high vacuum to provide compound 6-8 as a light yellow solid (3.17 g, 100% yield). $^1$H NMR (400 MHz, D$_2$O): δ7.58 (d, 1H, J 8.2 Hz), 7.25 (s, 1H), 6.99 (d, 1H, J 8.2 Hz), 3.85 (s, 2H).

Example 78

Preparation of (7-2)

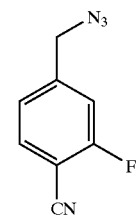

To a solution of α-bromo-4-cyano-3-fluorotoluene (compound 7-1, 10.00 g, 46.72 mmol) in DMF (100 mL) was added sodium azide (Aldrich, 3.64 g, 56.06 mmol). The reaction mixture was stirred at room temperature under nitrogen for 15 hours, and then poured into water (500 mL). The product was extracted with ether and the combined extracts were washed with brine three times, and dried over Na$_2$SO$_4$. After filtration, evaporation and high vacuum dry, a light yellow crystalline product (compound 7-2, 8.22 g, 100% yield) was obtained which was used for the next step without further purification. TLC R$_f$ 0.72 (hexane:EtOAc 5:1), $^1$H-NMR (400 MHz, CDCl$_3$): δ7.64 (dd, 1H, J 7.6 Hz, J 6.7 Hz), 7.22 (d, 1H, J 6.7 Hz), 7.21 (d, 1H, J 10.4 Hz), 4.47 (s, 2H).

Example 79

Preparation of (7-5)

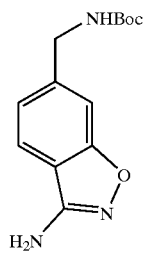

To a solution of α-azido-4-cyano-3-fluorotoluene (compound 7-2, 1.75 g, 10 mmol) in THF (46 mL) and water (2 mL), was slowly added triphenylphosphine (Aldrich, 2.89 g, 11 mmol). The mixture was stirred at room temperature for 15 hours, and then the solvents were evaporated. The residue was dissolved in 0.25 M HCl (75 mL, 18.7 mmol). The water solution was washed by EtOAc until no UV active compounds were detected, neutralized to pH ~10 by 2M NaOH solution, and then extracted with dichloromethane. The combined extracts were dried over $Na_2SO_4$. After filtration, the filtrate was condensed to 50 mL and used in the next step without further isolation. To that solution was added 1M $(Boc)_2O$ in THF (Aldrich, 11 mL, 11 mmol). The reaction mixture was stirred at room temperature for overnight. The solvents were evaporated and the residue was dissolved in dichloromethane (200 mL), washed by 0.5 N HCl, saturated aqueous $NaHCO_3$ and brine, and dried over $Na_2SO_4$. After filtration, evaporation and high vacuum dry, the product (compound 7-3) was obtained as a light yellow crystalline solid (2.48 mg, 99% yield). TLC $R_f$ 0.40 (hexane:EtOAc 3:1), $^1$H-NMR (400 MHz, $CDCl_3$): δ7.57 (dd, 1H, J 7.9 Hz, J 6.4 Hz), 7.17 (d, 1H, J 7.9 Hz), 7.14 (d, 1H, J 9.5 Hz), 5.02 (bs, 1H), 4.36 (bd, 2H, J 5.5 Hz), 1.46 (s, 9H).

The following procedure is based on a literature reference (M. G. Palermo, Tetrahedron Lett. 37 (17), 1996, 2885–2886) for making the similar compounds. To a solution of acetohydroxamic acid (Aldrich, compound 7-4, 450.4 mg, 6.0 mmol) in anhydrous DMF (4 mL) was added t-BuOK (Aldrich, 673.3 mg, 6.0 mmol). The mixture was stirred at room temperature under nitrogen for 30 minutes to get a gel-like suspension. Compound 7-3 (1.00 g, 4.0 mmol) was introduced, and the reaction mixture was stirred at room temperature under nitrogen for 15 hours and then at 70° C. for 24 hours. The mixture was cooled to room temperature, poured into water, and extracted with EtOAc. The combined extracts were washed with brine five times and dried over $Na_2SO_4$. After filtration and evaporation, the crude product was purified on a silica gel column eluting with hexane-EtOAc (from 4:1 to 1:1) to give some recovered compound 7-3 (415 mg, 1.66 mmol, 41%) and the product 7-5 as a white crystalline solid (583 mg, 55% yield, 95% yield based on the recovered starting material). TLC $R_f$ 0.09 (hexane:EtOAc 3:1); $^1$H-NMR (400 MHz, $CDCl_3$): δ7.47 (d, 1H, J 8.1 Hz), 7.34 (s, 1H), 7.18 (d, 1H, J 8.1 Hz), 4.97 (bs, 1H), 4.45 (bd, 2H, J 5.5 Hz), 4.36 (bs, 2H), 1.47 (s, 9H).

Example 80

Preparation of (7-6)

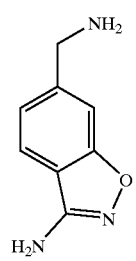

Compound 7-5 (580 mg, 2.20 mmol) was dissolved in 2M HCl in methanol/dioxane (1:1) (20 mL). The reaction mixture was stirred at room temperature for half an hour and a voluminous white precipitate formed. The precipitate was removed by filtration. After evaporation of solvents and co-evaporation with dichloromethane, the residue was suspended in methanol (20 mL), and to the mixture was added hydroxide form basic resin (AG 1-X8 Resin from Bio-Rad Laboratories) to make a clear solution and adjust the pH to ~10. The resin was filtered and washed with methanol thoroughly. The methanol solution was evaporated and the residue was dried under high vacuum to provide a free amine (compound 7-6) as a white solid (356 mg, 100% yield).

Example 81

Preparation of (8-2)

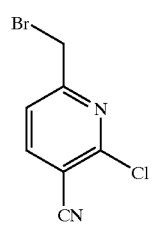

To a solution of 2-chloro-3-cyano-4-methylpyridine (compound 8-1, Aldrich, 10 g, 65.54 mmol) in carbon tetrachloride (250 mL), were added NBS (Aldrich, 12.83 g, 72.09 mmol) and benzoyl peroxide (1.59 g, 6.55 mmol). The reaction mixture was degassed and charged with nitrogen three times, and then refluxed at 85° C. for 6 hours. After cooling to room temperature, the solid by-product was removed by filtering and washed by $CCl_4$. The filtrate was evaporated and purified on a silica gel column eluting with hexane-EtOAc (from 10:1 to 5:1). The product 8-2 (5.28 g, 35% yield) was obtained as a light yellow solid. TLC $R_f$ 0.35 (hexane:EtOAc 5:1), $^1$H-NMR (400 MHz, $CDCl_3$): δ8.01 (d, 1H, J 7.9 Hz), 7.53 (d, 1H, J 7.9 Hz), 4.50 (s, 2H).

Example 82

Preparation of (8-3)

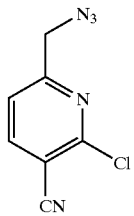

To a solution of α-bromo-2-chloro-3-cyano-4-methylpyridine (compound 8-2, 5.28 g, 22.83 mmol) in DMF (50 mL), was added sodium azide (Aldrich, 1.78 g, 27.40 mmol). The mixture was stirred at room temperature under nitrogen for 15 hours, and then poured into water (300 mL). The product was extracted with ether, the combined extracts were washed with brine three times, and dried over MgSO$_4$. After filtration and evaporation, the crude product was purified on a silica gel column eluting with hexane-EtOAc (from 9:1 to 5:1) to provide a product 8-3 as a light yellow solid (3.48 g, 79% yield). TLC R$_f$ 0.11 (hexane:EtOAc 9:1), $^1$H-NMR (400 MHz, CDCl$_3$): δ8.03 (d, 1H, J 7.9 Hz), 7.47 (d, 1H, J 7.9 Hz), 4.57 (s, 2H).

Example 83

Preparation of (8-4)

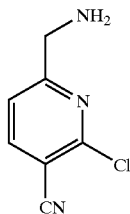

To a solution of α-azido-2-chloro-3-cyano-4-methylpyridine (compound 8-3, 3.48 g, 17.98 mmol) in THF (84 mL) and water (4 mL), was added triphenylphosphine (5.19 g, 19.77 mmol) slowly at 0° C. The reaction mixture was stirred at a temperature of from 0° C. to room temperature for 15 hours. During this time the color of the solution changed from light yellow to green, and then to deep red color. After evaporation of the solvents, the residue was dissolved in 0.25 M HCl (100 mL, 25 mmol). The aqueous solution was washed with EtOAc to give a colorless solution, and then neutralized to pH=11 with 2 M NaOH solution. The free amine was extracted with dichloromethane and the combined extracts were dried over Na$_2$SO$_4$. After filtration, evaporation and high vacuum dry, a green crystalline solid product (8-4) was obtained (1.58 g, 52% yield). 1H-NMR (400 MHz, CDCl$_3$): δ7.96 (d, 1H, J 7.9 Hz), 7.45 (d, 1H, J 7.9 Hz), 4.05 (s, 2H), 1.64 (bs, 2H).

Example 84

Preparation of (8-5)

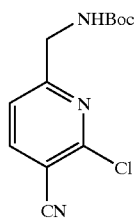

To the solution of α-amino-2-chloro-3-cyano-4-methylpyridine (compound 8-4, 1.58 g, 9.43 mmol) in dichloromethane (40 mL), was added 1M (Boc)$_2$O in THF (11.3 mL, 11.3 mmol). The mixture was stirred at room temperature for 15 hours. After evaporation of the solvent, the residue was purified on a silica gel column eluting with hexane-EtOAc (from 5:1 to 3:1) to provide product 8-5 as an off-white solid (1.07 g, 42% yield). TLC R$_f$ 0.73 (hexane:EtOAc 1:1), $^1$H-NMR (400 MHz, CDCl$_3$): δ7.96 (d, 1H, J 7.9 Hz), 7.38 (d, 1H, J 7.9 Hz), 5.32 (bs, 1H), 4.46 (bd, 2H, J 5.8 Hz), 1.46 (s, 9H).

Example 85

Preparation of (8-7)

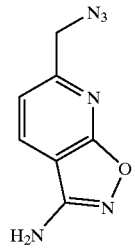

This is an modification based on a literature procedure (M. G. Palermo, Tetrahedron Lett. 37 (17), 1996, 2885–2886). To a solution of acetohydroxamic acid (8-6, 224.6 mg, 2.99 mmol) in anhydrous DMF (4 mL), was added t-BuOK (335.5 mg, 2.99 mmol). The mixture was stirred at room temperature under nitrogen for 15 minutes to get a gel-like suspension. To the mixture was added compound 8-5 (534 mg, 1.99 mmol). The reaction mixture was stirred at room temperature under nitrogen for 15 hours and then at 65° C. for 4 hours. After cooling to room temperature, the mixture was poured into water (100 mL) and extracted with EtOAc. The combined extracts were washed with brine five times and dried over Na$_2$SO$_4$. After filtration and evaporation, the crude product was purified on a silica gel column eluting with hexane-EtOAc (from 3:1 to 1:2) to provide the product, compound 8-7, as an off-white solid (370 mg, 70% yield). TLC R$_f$ 0.20 (hexane:EtOAc 1:1); $^1$H-NMR (400 MHz, CDCl$_3$) δ7.89 (d, 1H, J 7.9 Hz), 7.25 (d, 1H, J 7.9 Hz), 5.56 (bs, 1H), 4.56 (bd, 2H, J 5.5 Hz), 4.42 (bs, 2H), 1.46 (s, 9H)

89

Example 86

Preparation of (8-8)

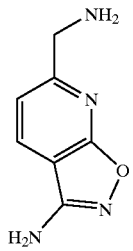

Compound 8-7 (340 mg, 1.29 mmol) was dissolved in a 2M HCl methanol/dioxane (1:1) solution (20 mL). The reaction mixture was stirred at room temperature for 4 hours and a voluminous white precipitate was formed. The precipitate was removed by filtering. After evaporation of solvent and co-evaporation with dichloromethane, the residue was suspended in methanol (20 mL). To that mixture was added hydroxide form basic resin (AG 1-X8 Resin from Bio-Rad Laboratories) to make a clear solution and adjust the pH ~10. The resin was filtered and washed with methanol thoroughly. The methanol solution was evaporated and the residue was dried under high vacuum to provide the free amine compound 8-8 as a white solid (204 mg, 99% yield).

Example 87

Preparation of (9-2)

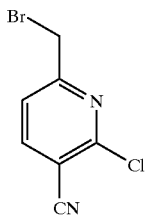

To a solution of 2-chloro-3-cyano-4-methylpyridine (compound 9-1, Aldrich, 10 g, 65.54 mmol) in carbon tetrachloride (250 mL), were added NBS (Aldrich, 12.83 g, 72.09 mmol) and benzoyl peroxide (Aldrich, 1.59 g, 6.55 mmol). The reaction mixture was degassed and charged with nitrogen three times, and then refluxed at 85° C. for 6 hours. After cooling to room temperature, the solid by-product was filtered off and washed by $CCl_4$. The filtrate was evaporated and purified on a silica gel column eluting with hexane-EtOAc (from 10:1 to 5:1). The product (Compound 9-2, 5.28 g, 35% yield) was obtained as a light yellow solid. TLC $R_f$ 0.35 (hexane:EtOAc 5:1), $^1$H-NMR (400 MHz, $CDCl_3$): δ8.01 (d, 1H, J 7.9 Hz), 7.53 (d, 1H, J 7.9 Hz), 4.50 (s, 2H).

90

Example 88

Preparation of (9-3)

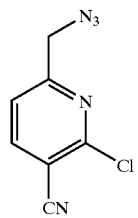

To a solution of α-bromo-2-chloro-3-cyano-4-methylpyridine (compound 9-2, 5.28 g, 22.83 mmol) in DMF (50 mL), was added sodium azide (Aldrich, 1.78 g, 27.40 mmol). The mixture was stirred at room temperature under nitrogen for 15 hours, and then poured into water (300 mL). The product was extracted with ether, the combined extracts were washed with brine three times, and dried over $MgSO_4$. After filtration and evaporation, the crude product was purified on a silica gel column eluting with hexane-EtOAc (from 9:1 to 5:1) to provide a light yellow solid product (compound 9-3, 3.48 g, 79% yield). TLC $R_f$ 0.11 (hexane:EtOAc 9:1), $^1$H-NMR (400 MHz, $CDCl_3$): δ8.03 (d, 1H, J 7.9 Hz), 7.47 (d, 1H, J 7.9 Hz), 4.57 (s, 2H).

Example 89

Preparation of (9-4)

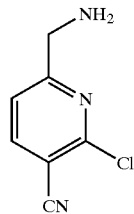

To a solution of α-azido-2-chloro-3-cyano-4-methylpyridine (compound 9-3, 3.48 g, 17.98 mmol) in THF (84 mL) and water (4 mL), was added triphenylphosphine (Aldrich, 5.19 g, 19.77 mmol) slowly at 0° C. The mixture was stirred at a temperature of from 0° C. to room temperature for 15 hours. During this time, the color of the solution changed from light yellow to green, and then to a deep red color. After evaporation of the solvents, the residue was dissolved in 0.25 M HCl (100 mL, 25 mmol). The aqueous solution was washed by EtOAc to give a colorless solution, and then neutralized to pH 11 with 2 M NaOH solution. The free amine was extracted with dichloromethane and the combined extracts were dried over $Na_2SO_4$. After filtration, evaporation and high vacuum dry, a green crystalline solid product (9-4) was obtained (1.58 g, 52% yield). $^1$H-NMR (400 MHz, $CDCl_3$): δ7.96 (d, 1H, J 7.9 Hz), 7.45 (d, 1H, J 7.9 Hz), 4.05 (s, 2H), 1.64 (bs, 2H).

Example 89
Preparation of (9-5)

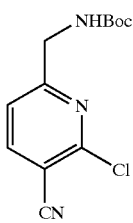

To a solution of α-amino-2-chloro-3-cyano-4-methylpyridine (compound 9-4, 1.58 g, 9.43 mmol) in dichloromethane (40 mL) was added 1M (Boc)$_2$O in THF (11.3 mL, 11.3 mmol). The reaction mixture was stirred at room temperature for 15 hours. After evaporation of the solvent, the residue was purified on a silica gel column eluting with hexane-EtOAc (from 5:1 to 3:1) to provide an off-white solid product (1.07 g, 42% yield). TLC Rf 0.73 (hexane:EtOAc 1:1), $^1$H-NMR (400 MHz, CDCl$_3$): δ7.96 (d, 1H, J 7.9 Hz), 7.38 (d, 1H, J 7.9 Hz), 5.32 (bs, 1H), 4.46 (bd, 2H, J 5.8 Hz), 1.46 (s, 9H).

Example 90
Preparation of (9-6)

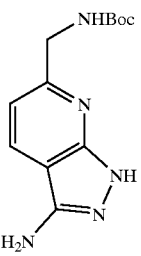

To a solution of compound 9-5 (535.4 mg, 2.0 mmol) in n-butanol (10 mL) was added hydrazine (0.19 mL, 6.0 mmol). The reaction mixture was refluxed under nitrogen for 4 hours. After evaporation of n-butanol and high vacuum dry, the product was obtained as a light yellow solid (526 mg, 100% yield). TLC R$_f$ 0.15 (5% MeOH in CH$_2$Cl$_2$), $^1$H-NMR (400 MHz, CD$_3$OD): δ8.07 (d, 1H, J 8.2 Hz), 6.99 (d, 1H, J 8.2 Hz), 4.37 (s, 2H), 1.44 (s, 9H).

Example 91
Preparation of (9-7)

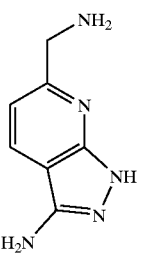

Compound 9-6 (520 mg, 1.97 mmol) was dissolved in a 2 M HCl methanol/dioxane (1:1) solution (20 mL). The reaction mixture was stirred at room temperature for 3 hours and a voluminous red precipitate formed. The precipitate was filtered off. After evaporation of solvent and co-evaporation with dichloromethane, the residue was suspended in methanol (20 mL), and to the mixture was added hydroxide form basic resin (AG 1-X8 Resin from Bio-Rad Laboratories) to make a clear solution and adjust the pH=10. The resin was filtered and washed with methanol thoroughly. The methanol solution was evaporated and the residue was dried under high vacuum to provide the free amine (compound 9-7) as a light yellow-green solid (303 mg, 94% yield). $^1$H-NMR (400 MHz, CD$_3$OD) _8.09 (d, 1H, J 8.2 Hz), 7.02 (d, 1H, J 8.2 Hz), 4.05 (s, 2H).

Example 92
Preparation of (10-2)

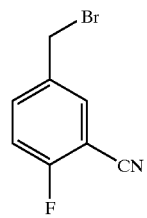

To a solution of 3-cyano-4-fluorotoluene (10-1) (Aldrich, 20.00 g, 148.0 mmol) in carbon tetrachloride (600 mL), were added NBS (Aldrich, 28.98 g, 162.8 mmol) and AIBN (Aldrich, 2.43 g, 14.8 mmol). The reaction mixture was degassed and charged with nitrogen three times, and then was refluxed at 85° C. for 8 hours. After standing at room temperature overnight, the mixture was filtered to remove solids and the solid by-product was washed by CCl$_4$. The filtrate was evaporated and purified on a silica gel column eluting with hexane-EtOAc (20:1). The product (Compound 10-2, 18.67 g, 59% yield) was obtained as a light yellow liquid which solidified after standing at room temperature. TLC R$_f$ 0.44 (hexane:EtOAc 10:1), $^1$H-NMR (400 MHz, CDCl$_3$): δ7.66–7.61 (m, 2H), 7.20 (t, 1H, J 8.5 Hz), 4.44 (s, 2H).

Example 93
Preparation of (10-3)

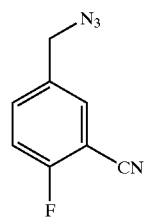

To the solution of α-bromo-3-cyano-4-fluorotoluene (compound 10-2, 18.67 g, 87.23 mmol) in DMF (200 mL) was added sodium azide (Adrich, 6.80 g, 104.67 mmol). The reaction mixture was stirred at room temperature under nitrogen for 15 hours, and then poured into water (300 mL). The product was extracted with ether and the combined extracts were washed with brine three times, and dried over Na$_2$SO$_4$. After filtration, evaporation and high vacuum dry, a light yellow liquid product (compound 10-3, 15.31 g, 100% yield) was obtained which was used for the next step without further purification. TLC R$_f$ 0.47 (hexane:EtOAc 10:1), $^1$H-NMR (400 MHz, CDCl$_3$): δ7.59–7.54 (m, 2H), 7.24 (t, 1H, J 8.4 Hz), 4.39 (s, 2H).

Example 94
Preparation of (10-4)

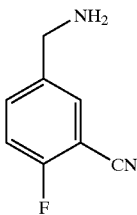

To the solution of α-azido-3-cyano-4-fluorotoluene (compound 10-3, 12.82 g, 74.45 mmol) in THF (348 mL) and water (16 mL) was added triphenylphosphine (Aldrich, 21.00 g, 80.05 mmol) slowly at 0° C. The mixture was stirred at a temperature of from 0° C. to room temperature for 15 hours, and then the solvents were evaporated. The residue was dissolved in 0.25 M HCl (300 mL, 75 mmol). The aqueous solution was washed with EtOAc until no UV active compounds were detected, adjusted to pH=10 with a 2 M NaOH solution, and then extracted with dichloromethane. The combined extracts were dried over $Na_2SO_4$. After filtration, evaporation and high vacuum dry, a light yellow liquid product (9.25 g, 85% yield) was obtained which was used for the next step without further purification. $^1$H-NMR (400 MHz, $CDCl_3$): δ7.60 (d, 1H, J 6.1 Hz), 7.56 (m, 1H), 7.16 (t, 1H, J 8.5 Hz), 3.89 (s, 2H), 1.44 (bs, 2H).

Example 95
Preparation of (10-5)

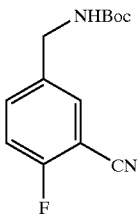

To a solution of α-amino-3-cyano-4-fluorotoluene (compound 10-4, 9.25 g, 63.27 mmol) in dichloromethane (316 mL) was added (Boc) 20 (Fluka, 15.19 g, 69.60 mmol). The mixture was stirred at room temperature for 2 hours. After evaporation of the solvent, the residue was purified on a silica gel column eluting with hexane-EtOAc (5:1 and 4:1) to provide a white crystalline solid product (13.10 g, 83% yield). TLC $R_f$ 0.27 (hexane:EtOAc 3:1); $^1$H-NMR (400 MHz, $CDCl_3$) δ7.54–7.50 (m, 2H), 7.17 (t, 1H, J 8.7 Hz), 4.99 (bs, 1H), 4.29 (bd, 2H, J 5.8 Hz), 1.45 (s, 9H).

Example 96
Preparation of (10-7)

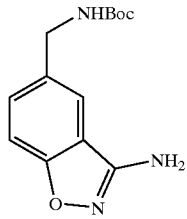

This procedure was developed in our laboratory based on a literature reference for making a desired bicyclic benzisoxazole ring (M. G. Palermo, Tetrahedron Lett. 37 (17), 1996, 2885–2886).

To a solution of acetohydroxamic acid (10-6) (227.5 mg, 3.0 mmol) in anhydrous DMF (4 mL) was added t-BuOK (Aldrich, 336.7 mg, 3.0 mmol). The mixture was stirred at room temperature under nitrogen for 15 minutes to obtain a gel-like suspension. To that mixture, was added compound 10-5 (500.6 mg, 2.0 mmol). The reaction mixture was stirred at room temperature under nitrogen for 15 hours. The mixture was poured into water and extracted with EtOAc. The combined extracts were washed with brine five times and dried over $Na_2SO_4$. After filtration and evaporation, the crude product was purified on a silica gel column eluting with hexane-EtOAc (from 4:1 to 1:1). Some starting material, acetohydroxamic acid (310 mg, 1.24 mmol, 62%), was recovered. The product (10-7) was obtained as a white solid (184 mg, 35% yield, 92% yield based on the recovered starting material). TLC $R_f$ 0.09 (hexane:EtOAc 3:1); $^1$H-NMR (400 MHz, $CDCl_3$): δ7.45 (s, 1H), 7.43 (d, 1H, J 8.5 Hz), 7.38 (d, 1H, J 8.5 Hz), 4.93 (bs, 1H), 4.39 (bd, 4H, J 5.5 Hz), 1.46 (s, 9H).

Example 97
Preparation of (10-8)

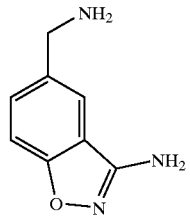

Compound 10-7 (178 mg, 0.68 mmol) was dissolved in 2 M HCl methanol/dioxane (1:1) (10 mL). The reaction mixture was stirred at room temperature for 5 hours and a voluminous white precipitate formed. After evaporation of solvent and co-evaporation with dichloromethane, the residue was suspended in methanol (20 mL). To that mixture was added hydroxide form basic resin (AG 1-X8 Resin from Bio-Rad Laboratories) to make a clear solution and adjust the pH to about 10. The resin was filtered and washed with methanol thoroughly. The methanol solution was evaporated and the residue was dried under high vacuum to provide the free amine compound 10-8 as a white solid (111 mg, 100% yield). $^1$H-NMR (400 MHz, $CDCl_3$) δ7.51 (s, 1H), 7.47 (d, 1H, J 8.8 Hz), 7.39 (d, 1H, J 8.5 Hz), 4.34 (bs, 2H), 3.99 (s, 4H, J 5.5 Hz).

Example 98
Preparation of (11-2)

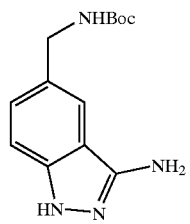

To a solution of compound 11-1 (10.0 g, 39.96 mmol) in n-butanol (200 mL) was added hydrazine (Aldrich, 2.63 mL, 83.91 mmol). The reaction mixture was refluxed under nitrogen for 22 hours. After evaporation of n-butanol, the residue was purified on a silica gel column eluting with 5% to 10% methanol in dichloromethane to provide a white crystalline solid product (compound 11-2, 5.47 g, 52% yield). TLC R$_f$ 0.26 (5% MeOH in CH$_2$Cl$_2$), $^1$H-NMR (400 MHz, CDCl$_3$): δ8.94 (bs, 1H), 7.46 (s, 1H), 7.30–7.27 (m, 2H), 4.87 (bs, 1H), 4.38 (bd, 2H, J 5.5 Hz), 4.09 (bs, 2H), 1.47 (s, 9H).

Example 99

Preparation of (11-3)

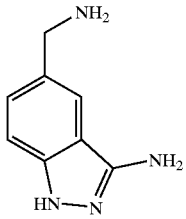

Compound 11-2 (2.47 g) was dissolved in 2 M HCl dioxane solution. The reaction mixture was stirred at room temperature for 3 hours. After evaporation of solvent, co-evaporation with dichloromethane and high vacuum dry, an off-white solid product (compound 90, 2.27 g, 99% yield) was obtained. $^1$H-NMR (400 MHz, D$_2$O): δ7.85 (s, 1H), 7.59 (d, 1H, J 8.8 Hz), 7.52 (d, 1H, J 8.8 Hz), 4.25 (s, 2H).

To a solution of compound 11-3 (2.00 g, 7.36 mmol) in methanol was added hydroxide form basic resin (AG 1-X8 Resin from Bio-Rad Laboratories) to adjust the pH to about 10. After filtration, the resin was washed by methanol thoroughly. The methanol solution was evaporated and the residue was dried under high vacuum to provide the free amine form of compound 11-3 as a yellow solid (1.15 g, 96% yield).

Example 100

Preparation of 4-(hydroxymethyl)-2-methylaniline (12-2)

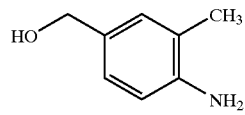

(Literature reference for making this compound see: Sun, J.-H.; Teleha, C. A.; Yan, J.-S.; Rodgers, J. D.; Nugiel, D. A. *J. Org. Chem.* 1997, 62, 5627–5629).

A solution of 3-methyl-4-nitrobenzyl alcohol (compound 12-1, 8.5 g, 50.9 mmol) in ethanol (100 mL) was stirred at room temperature, while 10% Pd/C (1.0 g) was added in one portion. The resulting suspension was hydrogenated (10 psi) in a Parr apparatus at room temperature for 1.5 hours. The catalyst was removed by filtration, and solvent was evaporated under vacuum to give the title compound (12-2, 6.9 g, 99%). MS (electrospray) 138 (M+1); $^1$H N MR (CDCl$_3$) δ2.16 (s, 3H), 2.72 (br s, 3H), 4.52 (s, 2H), 6.64 (d, 1H, J=8.0 Hz), 7.02 (d, 1H, J=8.0 Hz), 7.05 (s, 1H).

Use of high pressure (30 Psi) of hydrogen and a long reaction time (8 hours) resulted a hydrogenolysis product. The same starting material (12-1) (21.05 g, 126 mmol) yielded 2,4-dimethylaniline (12-16 p) (15.20 g, 100%) under such conditions. MS (electrospray) 122 (M+1); $^1$H N MR (CDCl$_3$) δ2.14 (s, 3H), 2.23 (s, 3H), 3.72 (br s, 1H), 6.58 (d, 1H, J=8.0 Hz), 6.84 (d, 1H, J=8.0 Hz), 6.87 (s, 1H).

Example 101

Preparation of 1-acetyl-5-(acetoxymethyl)indazole (12-3)

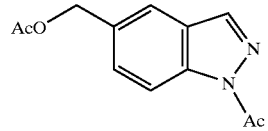

To a suspension of 2-methyl-4-(hydroxymethyl)aniline (compound 12-2, 4.0 g, 29 mmol) and potassium acetate (Aldrich, 8.6 g, 88 mmol) in chloroform (Calbiochem, 60 mL), was added acetic anhydride (Aldrich, 8.3 mL, 88 mmol) at room temperature, and the temperature was allowed to increase to 45° C. The mixture was then heated to reflux temperature for 2 hours under nitrogen. After cooling to room temperature, isoamylnitrite (Aldrich, 7.8 mL, 88 mmol) and 18-crown-6 (Aldrich, 1.5 g, 0.6 mmol) were added. The reaction mixture was heated at its reflux temperature for 28 hours. After returning to room temperature, the mixture was further treated with acetic anhydride (10 mL) and the solution was stirred at room temperature for 12 hours. The reaction mixture was diluted with methylene chloride (600 mL) and washed with saturated aqueous NaHCO$_3$ aqueous solution (300 mL), water (300 mL) and brine (50 mL). After drying (Na$_2$SO$_4$), the organic solvent was removed under vacuum to give a yellow oil which was purified by flash chromatography on silica gel (85:15 hexane-ethyl acetate) to yield the title compound (12-3, 6.21 g, 91%). TLC Rf 0.45 (70:30 of hexane-ethyl acetate); MS (electrospray) 233 (M+1); $^1$H N MR (CDCl$_3$) δ2.12 (s, 3H), 2.79 (app d, 3H, J=0.4 Hz), 5.23 (s, 2H), 7.56 (dd, 1H, J=8.8, 1.6 Hz), 7.74 (t, 1H, J=0.8 Hz), 8.12 (s, 1H), 8.43 (dd, 1H, J=8.8, 0.6 Hz).

Example 102

Preparation of 5-(bromomethyl)-1H-indazole Hydrogen Bromide (12-4)

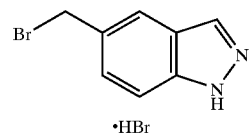

A suspension of 1-acetyl-5-(acetoxymethyl)indazole (12-3) (3.0 g, 13 mmol) in aqueous hydrobromic acid (15 mL, 226 mmol) was stirred at room temperature for 25 hours. The solid was collected on a Buchner funnel and dried under vacuum for 12 hours. The filtrate was stirred at room temperature for additional 24 hours and more solid was collected. After drying under vacuum, title compound was obtained as a yellow solid (12-4, 3.48 g, 92%) which was used in the next synthesis step without further purification. $^1$H NMR (CDCl$_3$) δ4.88 (s, 2H), 7.43 (d, 1H, J=8.8), 7.56 (d, 1H, J=8.8 Hz), 7.87 (s, 1H), 8.10 (s, 1H).

Example 103

Preparation of 5-(bromomethyl)-1-(2-tetrahydropyranyl)indazole (12-5)

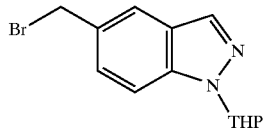

A yellow suspension of 5-(bromomethyl)-1H-indazole hydrogen bromide (compound 12-4, 3.0 g, 14 mmol) and 3,4-dihydro-2H-pyran (Aldrich, 2.4 g, 29 mmol) in THF (100 mL) was heated at reflux temperature for 2 hours. After cooling down to room temperature, the reaction mixture was stirred at room temperature for 12 hours under nitrogen. The reaction mixture was diluted with methylene chloride (250 mL), washed with saturated aqueous $NaHCO_3$, water and brine. After drying ($MgSO_4$), the solvent was removed under vacuum to give a yellow oil. Flash chromatography yielded the title compound (12-5, 3.34 g, 80%). TLC Rf 0.58 (70:30 hexane-ethyl acetate); MS (electrospray) 295, 297 (M+1); $^1$H N MR ($CDCl_3$) δ1.57–1.84 (m, 3H), 2.16 (m, 2H), 2.55 (m, 1H), 3.75 (m, 1H), 4.01 (m, 1H), 4.65 (s, 2H), 5.71 (d, 1H, J=9.2 Hz), 7.44 (d, 1H, J 8.8 Hz), 7.59 (d, 1H, J=8.8 Hz), 7.73 (s, 1H), 8.00 (s, 1H).

Example 104

Preparation of 5-(azidomethyl)-1-(2-tetrahydropyranyl)indazole (12-6)

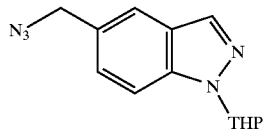

To a solution of 5-(bromomethyl)-1-(2-tetrahydropyranyl)indazole (compound 12-5, 3.0 g, 10.2 mmol) in DMF (30 mL), was added with sodium azide (Aldrich, 2.64 g, 40.6 mmol) in one portion. The suspension was heated at 90° C. for 30 minutes and a yellow solution was formed. After cooling to room temperature, the reaction mixture was poured into water (100 mL) and extracted with ether (2×150 mL). Combined organic layers were washed with brine, then dried ($MgSO_4$). Evaporation of solvent gave the product (12-6) as a yellow oil (2.61 g, 99%). TLC Rf 0.63 (60:40 hexane-ethyl acetate); MS (electrospray) 258 (M+1); $^1$H NMR ($CDCl_3$) δ2.03–2.15 (m, 2H), 2.55 (m, 1H), 3.72 (m, 1H), 4.02 (m, 1H), 4.52 (s, 1H), 5.71 (d, 1H, J=9.4 Hz), 7.32 (d, 1H, J=8.8 Hz), 7.56 (d, 1H, J=8.8 Hz), 7.63 (s, 1H), 8.00 (s, 1H).

Example 105

Preparation of 5-(aminomethyl)-1-(2-tetrahydropyranyl)indazole (12-7)

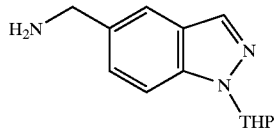

A solution of $LiAlH_4$ (Aldrich, 10.5 mL, 10.5 mmol, 1.0 M) in THF was added dropwise into a yellow solution of 5-(azidomethyl)-1-(2-tetrahydropyranyl)indazole (compound 12-6), 2.6 g, 10.1 mmol) in THF (30 mL) at 0° C. The addition time was 10 minutes, and gas was released. After stirring at 0° C. for 1 hour, NaOH (1.0 M, 1.5 mL) was added. The reaction mixture was allowed to warm to room temperature. Ethyl acetate (100 mL) was added, and the suspension was filtered (Celite). The filter cake was washed with an addition portion of ethyl acetate (40 mL). Combined organic layers were evaporated under vacuum to give free amine 12-7 (2.14 g, 92%). MS (electrospray) 232.5 (M+1); $^1$H NMR ($CDCl_3$) δ1.61 (m, 3H), 2.02 (m, 2H), 2.50 (m, 1H), 2.83 (br s, 2H), 3.68 (m, 1H), 3.85 (s, 2H), 3.95 (m, 1H), 5.62 (d, 1H, J=9.2 Hz), 7.29 (d, 1H, J=8.8 Hz), 7.48 (d, 1H, J=8.8 Hz), 7.53 (s, 1H), 7.92 (s, 1H).

Example 106

Preparation of (13-2)

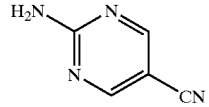

A solution of 2-amino-5-bromopyrimidine (13-1) (Aldrich, 50.0 g, 0.287 mol) and copper(I) cyanide (Aldrich, 33.0 g, 0.373 mol) in DMF (155 mL) was heated to reflux at 185° C. After 20 hours the reaction mixture was allowed to cool to room temperature. The residue was partitioned between ethyl acetate and 10% aqueous sodium cyanide solution. The organic layer was washed with 10% aqueous sodium cyanide solution, dried over magnesium sulfate, filtered, and evaporated in vacuo to afford the product (13-2) (22.8 g, 66%) as a brown solid. $R_f$=0.22 (1:1 of ethyl acetate/hexane). MS: m/e 121 (M+H)$^+$.

Example 107

Preparation of (13-3)

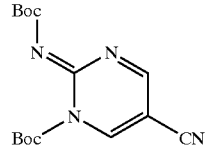

A solution of the product of Example 106 (13-2) (10.0 g, 0.083 mol), $Boc_2O$ (54.45 g, 0.250 mol) and DMAP (10.16 g, 0.083 mol) in THF (80 mL) was stirred at ambient temperature for 2 hours. The solvent was removed under vacuum. The residue was partitioned between ethyl acetate and aqueous 0.25 M HCl solution. The organic layer was washed with 10% aqueous $Na_2CO_3$ solution, and brine then dried over magnesium sulfate. Removal of organic solvent afforded the product (13-3) (15.9 g, 60%) as a brown solid. $R_f$=0.7 (1:1 of ethyl acetate/hexane). MS: m/e 321(M+H)$^+$.

Example 108

Preparation of (13-4)

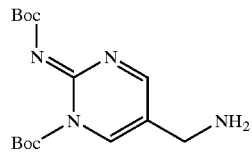

A suspension of the compound of Example 107 (13-3) (7.0 g, 21.8 mmol), 10% Pd/C (Aldrich, 2.8 g), and 1M aqueous HCl (21.9 mL) in ethanol (80 mL) was shaken in a Parr apparatus under $H_2$ (50 psi) for 16 hours. The solid was removed and the solution was concentrated under vacuum to give the product (13-4) (4.9 g, 69%). $R_f$=0.46 (1:1 of ethyl acetate/ hexane). MS: m/e 325(M+H)$^+$.

Example 109

Preparation of (14-2)

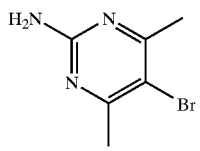

To a solution of 2-amino-4,6-dimethylpyrimidine (14-1, Aldrich, 20.0 g, 162.39 mmol) in acetic acid (200 mL) was added bromine (Spectrum, 28.55 g, 178.62 mmol) drop-wise at 0° C. After half of the portion of bromine was added, the reaction mixture changed color from clear to dark orange. The reaction was monitored by TLC using (1 ethylacetate/1 hexane). Saturated aqueous $NaHCO_3$ was added to neutralize HOAc. The reaction mixture was extracted with ethylacetate (2×). The organic layer was washed with saturated aqueous $NaHCO_3$ and evaporated in vacuo to give compound (14-2) (21.32 g, 65%). $R_f$=0.29 (1:1 of ethyl acetate/hexane). MS: m/e 203 (M+H)$^+$.

Example 110

Preparation of (14-3)

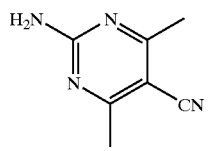

A solution of 2-amino-4,6-dimethyl-5-bromopyrimidine (14-2, 20.0 g, 98.93 mmol) and copper(I) cyanide (Aldrich, 11.52 g, 128.61 mmol) in DMF (200 mL) was heated at reflux. After 20 hours, the reaction mixture was allowed to cool to room temperature. The residue was partitioned between ethyl acetate and 10% aqueous sodium cyanide solution. The organic layer was washed with 10% aqueous sodium cyanide solution, dried over magnesium sulfate, and evaporated in vacuo to afford compound (14-3) as a yellow solid (9.0 g, 61%). $R_f$=0.17 (1:1 of ethyl acetate/hexane). MS: m/e 149 (M+H)$^+$.

Example 111

Preparation of (14-4)

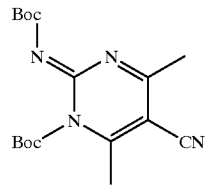

A solution of (14-3) (8.6 g, 58.10 mmol), $Boc_2O$ (25.33 g, 116.22 mmol) and DMAP (7.1 g, 58.10 mmol) in THF (150 mL) was stirred at ambient temperature for 2 hours. The solvent was removed under vacuum. The residue was partitioned between ethyl acetate and aqueous 0.25M HCl solution. The organic layer was washed with 10% aqueous $Na_2CO_3$ solution and brine, then dried over magnesium sulfate. Removal of organic solvent afforded compound (14-4) (15.6 g, 77%) as a dark brown solid. $R_f$=0.33 (1:2 of ethyl acetate/hexane). MS: m/e 349(M+H)$^+$.

Example 112

Preparation of (14-5)

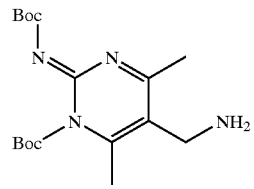

A suspension of compound (14-4) (6.5 g, 18.68 mmol), 10% Pd/C (Aldrich, 1.3 g), and 1M aqueous HCl (375 µL) in ethanol (30 mL) was shaked in a Parr apparatus under $H_2$ (45 psi) for 16 hours. The solid was removed and the solution was concentrated under vacuum to give compound (14-5) (6.11 g, 93%). MS: m/e 353(M+H)$^+$.

Example 113

Preparation of (15-2)

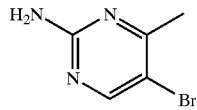

A solution of 2-amino-4-methylpyrimidine (15-1, Aldrich, 10.0 g, 91.63 mmol) and sodium carbonate (Aldrich, 4.8 g, 45.81 mmol) in water (100 mL) was heated to 65° C. Then, bromine (Aldrich, 16.1 g, 100.79 mmol) was added drop-wise to the reaction mixture. After 1.5 hours the reaction mixture was allowed to cool to room temperature; then, saturated aqueous $NaHCO_3$ was added. The precipitate was filtered and recrystallized from ethyl alcohol. The residue was dried under vacuum to give compound (15-2) (11.0 g, 65%) as a yellow solid. MS: m/e 188 (N4+H)$^+$.

Example 114

Preparation of (15-3)

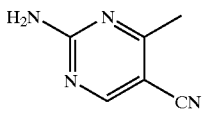

A solution of 2-amino-4-methyl-5-bromopyrimidine (15-2, 10.0 g, 53.19 mmol) and copper(I) cyanide (Aldrich, 6.19 g, 69.14 mmol) in DMF (80 mL) was heated to reflux at 185° C. After 20 hours, the reaction mixture was allowed to cool to room temperature. The residue was partitioned between ethyl acetate and 10% aqueous sodium cyanide solution. The organic layer was washed with 10% aqueous sodium cyanide solution, dried over magnesium sulfate, and evaporated in vacuo to afford yellow solid (4.27 g, 60%). $R_f$=0.19 (1:1 of ethyl acetate/hexane). MS: m/e 135 $(M+H)^+$.

Example 115

Preparation of (15-4)

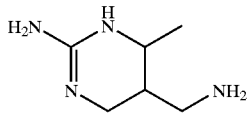

A suspension of compound (15-3) (1.0 g, 7.46 mmol), 10% Pd/C (Aldrich, 250 mg), and 1M aqueous HCl (14.8 mL) in ethanol (11 mL) and THF (15 mL) was shaken in a Parr apparatus under $H_2$ (20 psi) for 16 hours. The solid was removed and the solution was concentrated under vacuum to give compound (15-4) (1.0 g, 94%). MS: m/e 216 $(M+H+MeOH+Na+H_2O)^+$.

Example 116

Preparation of (16-2)

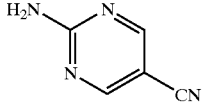

A solution of 2-amino-5-bromopyrimidine (16-1, Aldrich, 50.0 g, 0.287 mol) and copper(I) cyanide (Aldrich, 33.0 g, 0.373 mol) in DMF (155 mL) was heated to reflux at 185° C. After 20 hours the reaction mixture was allowed to cool to room temperature. The residue was partitioned between ethyl acetate and 10% aqueous sodium cyanide solution. The organic layer was washed with 10% aqueous sodium cyanide solution, dried over magnesium sulfate, filtered, and evaporated in vacuo to afford compound (16–2) (22.8 g, 66%) as a brown solid. $R_f$=0.22 (1:1 of ethyl acetate/hexane). MS: m/e 121 $(M+H)^+$.

Example 117

Preparation of (16-3)

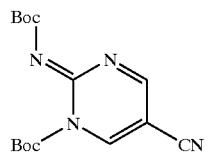

A solution compound (16-2) (10.0 g, 0.083 mol), $Boc_2O$ (54.45 g, 0.250 mol) and DMAP (10.16 g, 0.083 mol) in THF (80 mL) was stirred at ambient temperature for 2 hours. The solvent was removed under vacuum. The residue was partitioned between ethyl acetate and aqueous 0.25M HCl solution. The organic layer was washed with 10% aqueous $Na_2CO_3$ solution, and brine; then, dried over magnesium sulfate. Removal of organic solvent afforded compound (16-3) (15.9 g, 60%) as a brown solid. $R_f$=0.7 (1:1 of ethyl acetate/hexane). MS: m/e 321 $(M+H)^+$.

Example 118

Preparation of (16-4)

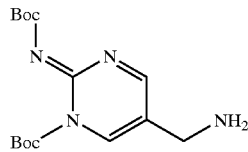

A suspension of compound (16-2) (7.0 g, 21.8 mmol), 10% Pd/C (Aldrich, 2.8 g), and 1M aqueous HCl (21.9 mL) in ethanol (80 mL) was shaken in a Parr apparatus under $H_2$ (50 psi) for 16 hours. The solid was removed and the solution was concentrated under vacuum to give compound (16-4) (4.9 g, 69%). $R_f$ 0.46 (1:1 of ethyl acetate/hexane). MS: m/e 325$(M+H)^+$.

Figure 17A:
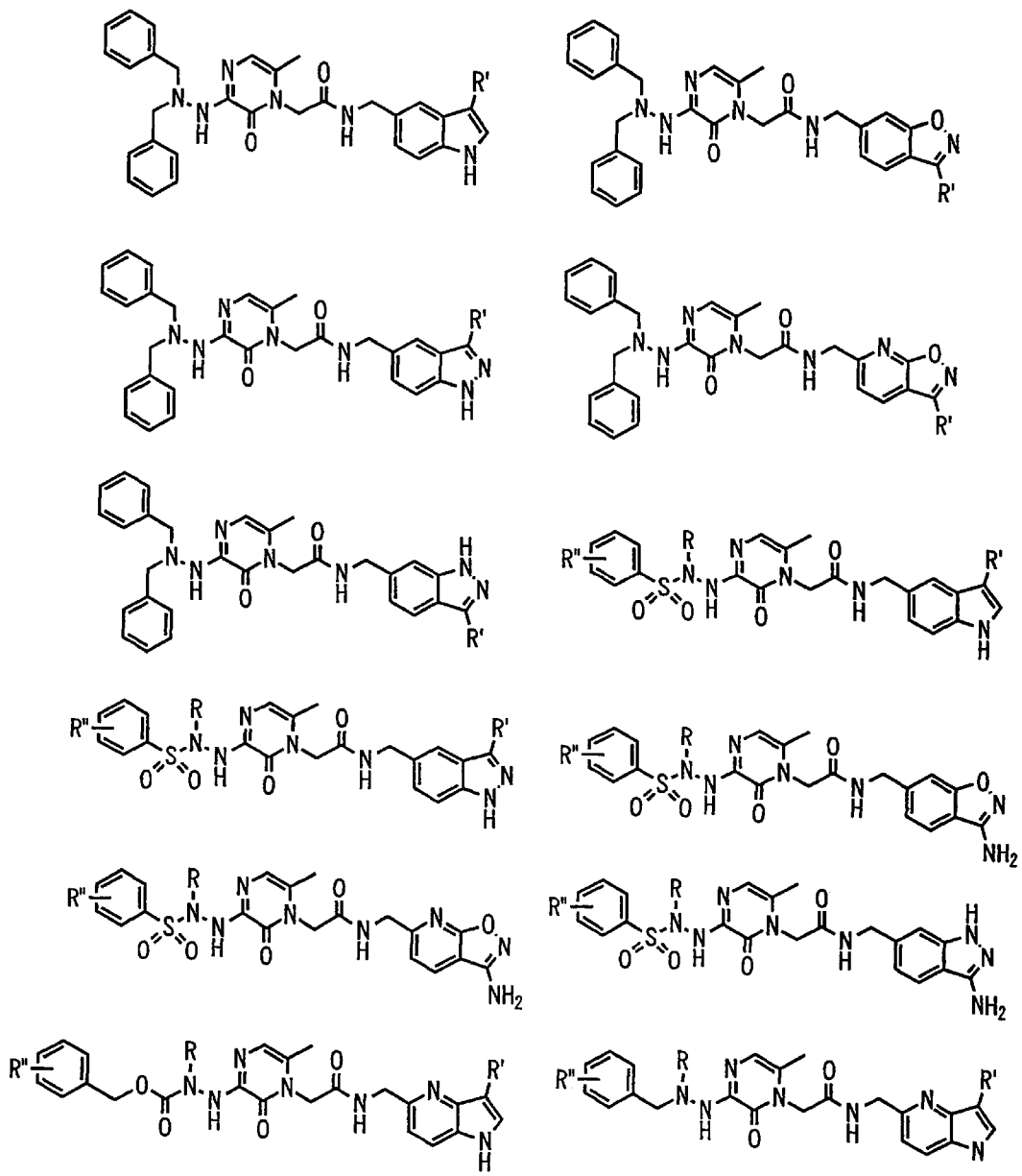
FIGS. 17A to 17C depict preferred compounds of the present invention.
Figure 17B:
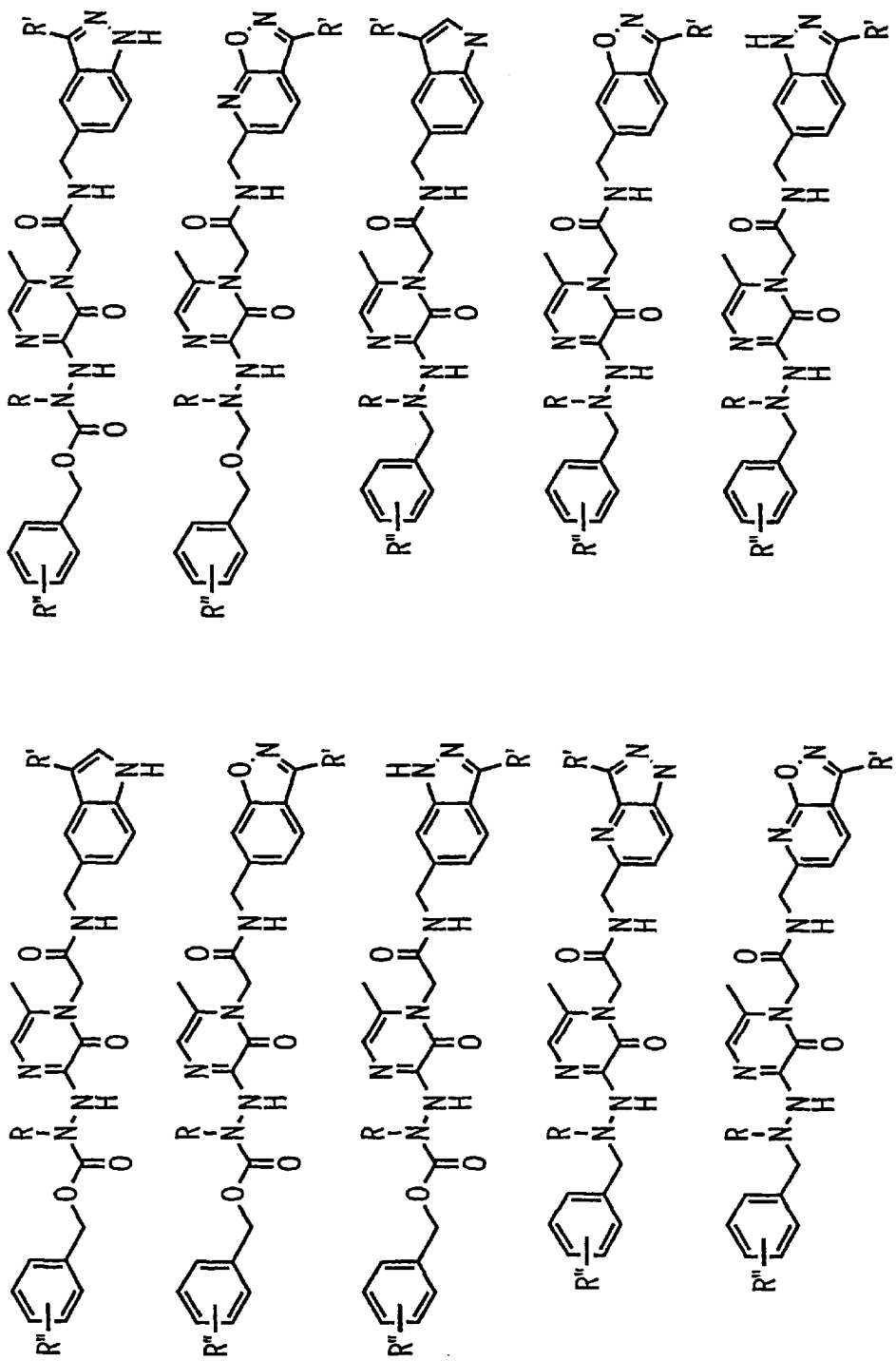
Figure 17C:
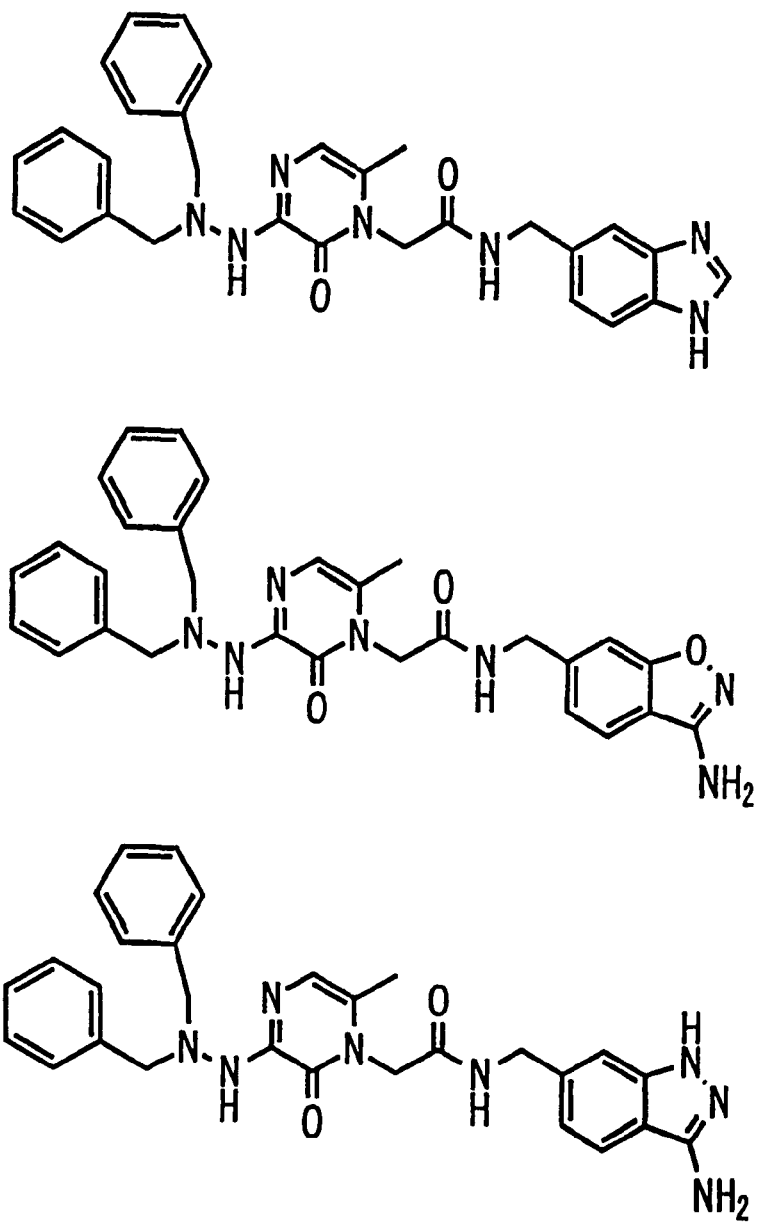

By following the teachings set forth in the Detailed Description of the Invention and Examples 1 to 118 and using the appropriate starting materials and requests the compounds depicted in FIGS. 17A to 17C are prepared.

Example A

In vitro Enzyme Assays for Specificity Determination

The ability of compounds of the present invention to act as a selective inhibitor of thrombin activity was assessed by determining the concentration of test-compound which inhibited the activity of this enzyme by 50%, ($IC_{50}$), and comparing this value to that determined for all or some of the following related serine proteases: recombinant tissue plasminogen activator (rt-PA), plasmin, activated protein C, chymotrypsin, factor Xa and trypsin.

The buffer used for all assays was HBSA (10 mM HEPES, pH 7.5, 150 mM sodium chloride, 0.1% bovine serum albumin).

The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_0$ (uninhibited velocity) measurement), and 50 microliters of the enzyme diluted in HBSA. Following a 30 minute incubation at ambient temperature, 50 microliters of the substrate at the concentrations specified below were added to the wells, yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Thrombin (fIIa) Assay

Enzyme activity was determined using the chromogenic substrate, Pefachrome t-PA ($CH_3SO_2$-D-hexahydrotyrosine-glycyl-L-Arginine-p-nitroaniline, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 μL), α-thrombin (50 μl) (the final enzyme concentration is 0.5 nM) and inhibitor (50 μl) (covering a broad concentration range), were combined in appropriate wells and incubated for 30 minutes at room temperature prior to the addition of substrate Pefachrome-t-PA (50 μl) (the final substrate concentration is 250 μM, about 5 times Km). The initial velocity of Pefachrome t-PA hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Factor Xa

Factor Xa catalytic activity was determined using the chromogenic substrate S-2765 (N-benzyloxycarbonyl-D-arginine-L-glycine-L-arginine-p-n nitroaniline ), obtained from DiaPharma Group (Franklin, OH). All substrates were reconstituted in deionized water prior to use. The final concentration of S-2765 was 250 μM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. Arch. Biochem. Biophys. 273:375–388 (1989)]. The enzyme was diluted into HBSA prior to assay in which the final concentration was 0.25 nM.

Recombinant Tissue Plasminogen Activator (rt-PA) Assay rt-PA catalytic activity was determined using the substrate, Pefachrome t-PA ($CH_3SO_2$-D-hexahydrotyrosine-glycyl-L-arginine-p-nitroanil ine, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2366 [L-pyroglutamyl-L-prolyl-L-arginine-p-nitroaniline hydrochloride], which was obtained from DiaPharma group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay aPC catalytic activity was determined using the chromogenic substrate, Pefachrome PC (delta-carbobenzloxy-D-lysine-L-prolyl-L-arginine-p-nitr oaniline dihydrochloride), obtained from Pentapharm Ltd.). The substrate was made up in deionized water followed by dilution in HBSA prior to the assay in which the final concentration was 400 micromolar (about 3-times Km). Purified human aPC was obtained from Hematologic Technologies, Inc. The enzyme was diluted into HBSA prior to assay in which the final concentration was 1.0 nM.

Chymotrypsin Assay

Chymotrypsin catalytic activity was determined using the chromogenic substrate, S-2586 (methoxy-succinyl-L-arginine-L-prolyl-L-tyrosyl-p-nitroa nilide), which was obtained from DiaPharma Group. The substrate was made up in deionized water followed by dilution in HBSA prior to the assay in which the final concentration was 100 micromolar (about 9-times Km). Purified (3x-crystallized; CDI) bovine pancreatic alpha-chymotrypsin was obtained from Worthington Biochemical Corp. The enzyme was reconstituted in deionized water and diluted into HBSA prior to assay in which the final concentration was 0.5 nM.

Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3x-crystallized; TRL3) bovine pancreatic trypsin was obtained from Worthington Biochemical Corp. The enzyme was reconstituted in deionized water and diluted into HBSA prior to assay in which the final concentration was 0.5 nM.

Table I lists the determined $IC_{50}$ values for certain of the enzymes listed above for compounds of the present invention and demonstrate the high degree of specificity for the inhibition of alpha-thrombin compared to these related serine proteases.

TABLE I

| Compound of Example No. | fIIa | | fxa | Plasmin | Trypsin |
|---|---|---|---|---|---|
| | IC50 (0 min) | IC50 (30 min) | IC50 (30 min) | IC50 (30 min) | IC50 (30 min) |
| 22 | A | A | D | D | C |
| 24 | A | A | D | D | C |
| 25 | A | A | D | D | D |
| 55 | A | A | D | D | D |
| 28 | A | A | C | D | D |
| 30 | A | A | D | D | D |
| 31 | A | A | D | D | C |
| 12 | A | A | D | C | D |
| 32 | A | A | D | C | D |
| 37 | A | A | D | D | D |
| 57 | A | A | C | D | D |
| 45 | A | A | C | D | D |
| 48 | A | A | D | D | D |
| 49 | A | A | D | D | D |
| 50 | A | A | C | D | C |
| 53 | A | A | C | D | C |
| 54 | A | A | D | D | D |
| 60 | A | A | C | D | D |
| 58 | A | A | D | D | D |
| 59 | A | A | D | D | C |

A = ≤ 100 nM
B = > 100, < 2500 nM
C = ≥ 2500, <100,000 nM
D = ≥ 100,000 nM

We claim:
1. A compound of the formula

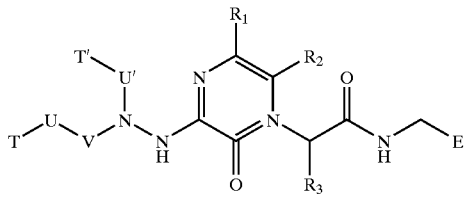

wherein:
(a) V is selected from the group consisting of —O—C(=O)—, —C(=O) —NH—C(=O), —NH—C(=O)—, —C(=O)—, —O—C(=S)—, —NH—S(O)$_2$—, —S(O)$_2$, and a direct link;
(b) U and U' are independently selected from the group consisting of $C_{1-3}$ alkylene, $C_{1-3}$ alkylene substituted with $C_{1-3}$ alkyl and a direct link;
(c) T and T' are independently selected from the group consisting of
(1) $C_{1-6}$ alkyl, $C_{2-6}$ alkenyl, $C_{2-6}$ alkynyl,
(2) $C_{1-6}$haloalkyl, $C_{3-6}$haloalkenyl, $C_{3-6}$haloalkynyl;
(3) $C_{2-6}$oxaalkyl, $C_{3-6}$oxaalkenyl, $C_{3-6}$oxaalkynyl;
(4) $C_{1-6}$hydroxyalkyl, $C_{3-6}$hydroxyalkenyl, $C_{3-6}$hydroxyalkynyl;
(5) $C_{1-6}$carboxyalkly, $C_{2-6}$carboxyalkenyl, $C_{2-6}$carboxyalkynyl;
(6) —$C_{1-3}$alkyl-carbonyl-$C_{1-3}$alkyl, —$C_{2-4}$alkenyl-carbonyl-$C_{2-4}$alkenyl, —$C_{2-4}$alkynyl-carbonyl-$C_{2-4}$alkynyl;
(7) $C_{1-6}$nitroalkyl, $C_{2-6}$nitroalkenyl, $C_{2-6}$nitroalkynyl;
(8) $C_{1-6}$alkylamine, $C_{2-6}$alkenylamine, $C_{2-6}$alkynylamine;
(9) $C_{1-6}$alkylimine, $C_{2-6}$alkenylimine, $C_{2-6}$alkynylimine;
(10) $C_{1-6}$alkylamide, $C_{2-6}$alkenylamide, $C_{2-6}$alkynylamide;
(11) $C_{1-6}$alkyl-O—C(=O)NH$_2$, $C_{2-6}$alkenyl-O—C(=O)NH$_2$, $C_{2-6}$alkynyl-O—C(=O)NH$_2$;
(12) $C_{1-6}$alkylurea; $C_{2-6}$alkenylurea; $C_{2-6}$alkynylurea;
(13) $C_{1-6}$alkylhydrazine, $C_{2-6}$alkenylhydrazine, $C_{2-6}$alkynylhydrazine;
(14) $C_{1-6}$alkylnitrile, $C_{2-6}$alkenylnitrile, $C_{2-6}$alkynylnitrile;
(15) $C_{1-6}$alkylazide, $C_{2-6}$alkenylazide, $C_{2-6}$alkynylazide;
(16) $C_{1-6}$thioalkyl, $C_{3-6}$thioalkenyl, $C_{3-6}$thioalkynyl;
(17) $C_{1-6}$alkylthiol, $C_{2-6}$alkenylthiol, $C_{3-6}$alkynylthiol;
(18) $C_{3-6}$alkylisothiol, $C_{3-6}$alkenylisothiol, $C_{4-6}$alkynylisothiol;
(19) —$C_{1-6}$alkyl-thionyl-$C_{1-6}$alkyl, —$C_{2-6}$alkenyl-thionyl-$C_{2-6}$alkenyl, —$C_{2-6}$alkynyl-thionyl-$C_{2-6}$alkynyl;
(20) —$C_{1-6}$alkyl-sulphuryl-$C_{1-6}$alkyl, —$C_{2-6}$alkenyl-sulphuryl-$C_{2-6}$alkenyl, —$C_{2-6}$alkenyl-sulphuryl-$C_{2-6}$alkynyl;
(21) $C_{1-6}$alkylsulphonyl, $C_{2-6}$alkenylsulphonyl, $C_{2-6}$alkynylsulphonyl;
(22) $C_{1-6}$alkylsulphonamide, $C_{2-6}$alkenylsulphonamide, $C_{2-6}$alkynylsulphonamide;
(23) $C_{3-7}$cycloalkyl, halo-$C_{3-7}$cycloalkyl, $C_{3-7}$cycloalkyl-$C_{1-6}$alkyl, $C_{3-7}$cycloalkyl-di($C_{1-6}$alkyl), $C_{3-7}$cycloalkyl-$C_{3-6}$alkenyl, —$C_{3-7}$cylcloalkyl-$C_{3-6}$alkynyl;
(24) heterocycloalkyl of 4 to 10 ring atoms with the ring atoms selected from carbon and heteroatoms, wherein the heteroatoms are selected from the group consisting of oxygen, nitrogen, and $S(O)_i$, wherein i is 0, 1 or 2, which is optionally mono-, di-, or tri-substituted on the ring with $Y_1$, $Y_2$ and/or $Y_3$;
(25) heterocyclo of 4 to 10 ring atoms with the ring atoms selected from carbon and heteroatoms, wherein the heteroatoms are selected from the group consisting of oxygen, nitrogen, and $S(O)_i$, which is optionally mono-, di-, or tri-substituted on the ring carbons with $Y_1$, $Y_2$ and/or $Y_3$;
(26) aryl of 6 to 14 carbon atoms which is optionally mono-, di- or tri-substituted with $Y_1$, $Y_2$ and/or $Y_3$;
(27) heteroaryl of 5 to 14 ring atoms with the ring atoms selected from carbon and heteroatoms, wherein the heteroatoms are selected from oxygen, nitrogen, and sulfur, and which is optionally mono-, di-, or tri-substituted with $Y_1$, $Y_2$ and/or $Y_3$;
(28) aralkyl of 7 to 15 carbon atoms which is optionally substituted on the alkyl chain with hydroxy or halogen and mono-, di, or tri-substituted in the aryl ring with $Y_1$, $Y_2$ and/or $Y_3$;
(29) heteroaralkyl of 5 to 14 ring atoms with the ring atoms selected from carbon and heteroatoms, wherein the heteroatoms are selected from oxygen, nitrogen, and sulfur, and which is optionally substituted on the alkyl chain with hydroxy or halogen and optionally mono-, di- or tri-substituted on the ring with $Y_1$, $Y_2$ and/or $Y_3$;
(30) aralkenyl of 8 to 16 carbon atoms which is optionally mono-, di-, or tri-substituted on the aryl ring with $Y_1$, $Y_2$ and/or $Y_3$;
(31) heteroaralkenyl of 5 to 14 ring atoms with the ring atoms selected from carbon and heteroatoms, wherein the heteroatoms are selected from oxygen, nitrogen, and sulfur, and which is optionally mono-, di- or tri-substituted on the ring with $Y_1$, $Y_2$ and/or $Y_3$;
(32) fused carbocyclic of 5 to 13 carbon atoms, optionally substituted with $Y_1$, $Y_2$ and/or $Y_3$;
(33) fused carbocyclic alkyl of 6 to 16 carbon atoms, optionally substituted with $Y_1$, $Y_2$ and/or $Y_3$; and
(34) hydrogen;
(d)
(1) each $Y_1$, $Y_2$ and $Y_3$ is independently selected from the group consisting of halogen, cyano, nitro, tetrazolyl optionally substituted with alkyl of 1 to 6 carbon atoms, guanidino, amidino, methylamino, methylguanidino, —$CF_3$, —$CF_2CF_3$, —$CH(CF_3)_2$, —$C(OH)(CF_3)_2$, —$OCF_3$, —$OCF_2CF_3$, —$OCF_2H$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NZ_1Z_2$, —$C(O)OH$, —$C(O)OZ_1$, —$C(O)NH_2$, —$C(O)NZ_1Z_2$, —$P(O)_3H_2$, —$P(O)_3(Z_1)_2$, —$S(O)_3H$, —$S(O)_pZ_1$, —$Z_1$, —$OZ_1$, —$OH$, —$NH_2$, —$NHZ_1$, —$NZ_1Z_2$, N-morpholino, nitro, —$C≡N$, and —$S(O)_p(CF_2)_qCF_3$, wherein p is 0, 1 or 2, q is an integer from 0 to 5, and $Z_1$ and $Z_2$ are independently selected from the group consisting of alkyl of 1 to 12 carbon atoms, aryl of 6 to 14 carbon atoms, heteroaryl of 5 to 14 atoms having 1 to 9 carbon atoms, aralkyl of 7 to 15 carbon atoms, and heteroaralkyl of 5 to 14 ring atoms having 3 to 9 carbon atoms, or
(2) $Y_1$, and $Y_2$ are selected together to be —$O[C(Z_3)(Z_4)]_rO$— or —$O[C(Z_3)(Z_4)]_{r+1}$—, wherein r is an integer from 1 to 4 and $Z_3$ and $Z_4$ are independently selected from the group consisting of hydrogen, alkyl or 1 to 12 carbon atoms, aryl of 6 to 14 carbon atoms, heteroaryl of 5 to 14 ring atoms having 1 to 9 carbon atoms, aralkyl of 7 to 15 carbon atoms, and heteroaralkyl of 5 to 14 ring atoms having 3 to 9 carbon atoms;
(e) $R_1$ is selected from hydrogen, halogen, and methyl;
(f) $R_2$ is selected from hydrogen, $C_{1-4}$alkyl, $C_{3-7}$cycloalkyl, and $CF_3$;
(g) $R_3$ is hydrogen or $C_{1-4}$alkyl; and
(h) E is:

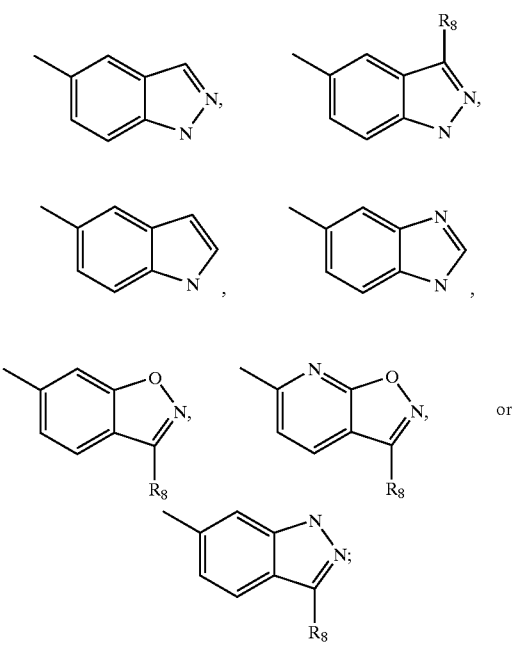

wherein
(1) $R_8$ is —$NR_{15}R_{16}$ or —$OR_{15}$;
(2) $R_{15}$ is hydrogen, alkyl of 1 to 3 carbon atoms, or —C(=O)$R_{17}$;
(3) $R_{16}$ is hydrogen or alkyl of 1 to 3 carbon atoms;
(4) alternatively, $R_{15}$ and $R_{16}$ taken together form a divalent radical of the formula —$(CH_2)_w$—, where w is independently 3, 4 or 5; and
(5) $R_{17}$ is alkyl of 1 to 6 carbon atoms or alkoxy of 1 to 6 carbon atoms and pharmaceutically acceptable salts thereof.

2. A compound according to claim 1 wherein U' is a direct link and T' is hydrogen.

3. A compound according to claim 2 wherein V is selected from the group consisting of —O—C(=O)—, —NH—C(=O)—, —C(=O)—, —S(O)$_2$— and a direct link.

4. A compound according to claim 3 wherein U is selected from the group consisting of —$CH_2$—, —$CH(CH_3)$—, —$CH_2CH_2$— and a direct link.

5. A compound according to claim 4 wherein $R_3$ is hydrogen.

6. A compound according to claim 5 wherein $R_1$ is hydrogen.

7. A compound according to claim 6 wherein $R_2$ is methyl.

8. A compound according to claim 7 wherein T is selected from the group consisting of phenyl, substituted phenyl, benzyl, substituted benzyl, alkyl, alkenyl, and alkynyl.

9. A compound according to claim 8 wherein U is a direct link and T is selected from the group consisting of benzyl, substituted benzyl, phenyl, substituted phenyl, and 2-propargyl.

10. A compound according to claim 9 wherein E is selected from

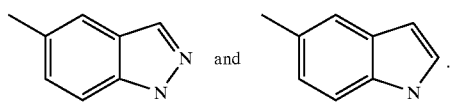

11. A compound according to claim 1 wherein V is a direct link.

12. A compound according to claim 11 where U and U' are independently alkylene.

13. A compound according to claim 12 wherein T and T' are independently phenyl or substituted phenyl.

14. A compound according to claim 13 wherein $R_1$ and $R_3$ are hydrogen.

15. A compound according to claim 14 wherein $R_{2'}$ is methyl.

16. A compound according to claim 15 wherein E is selected from

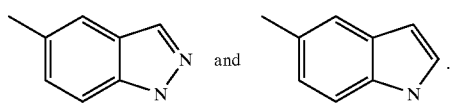

17. A compound according to claim 1 which is selected from the group consisting of

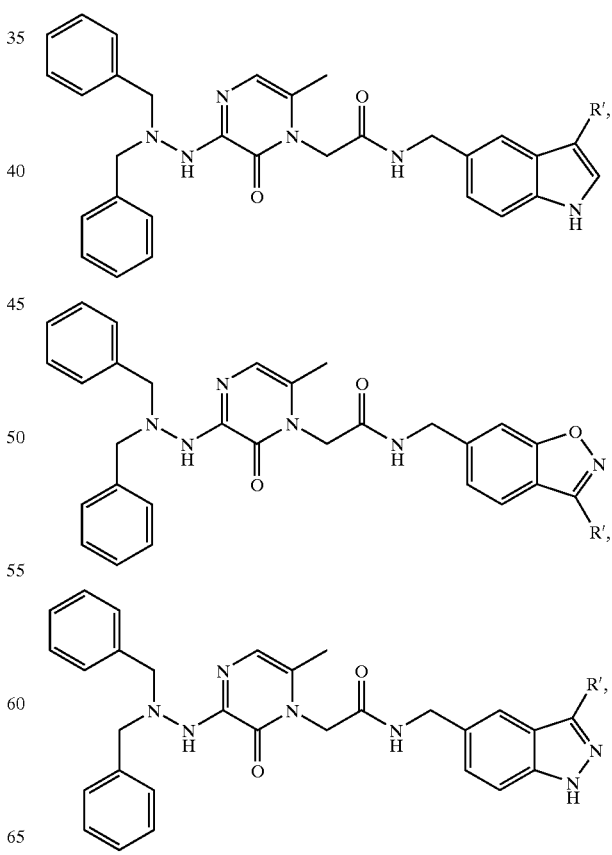

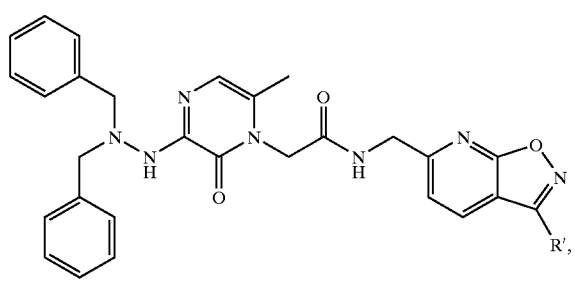
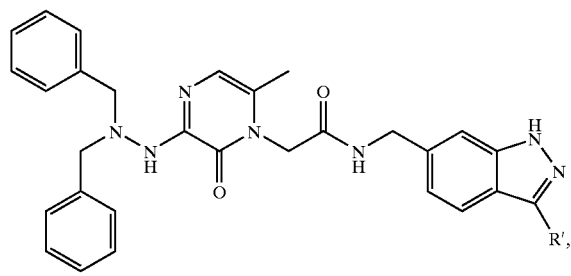
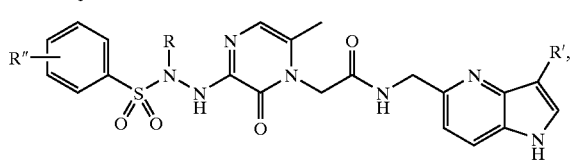
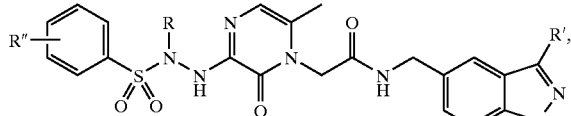
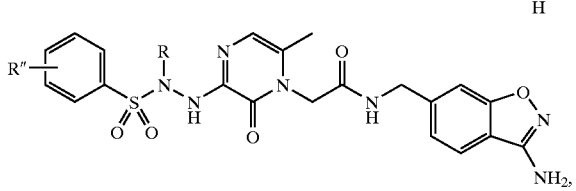
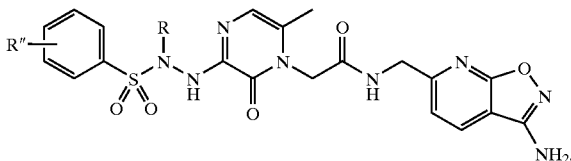
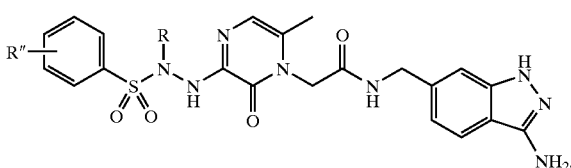
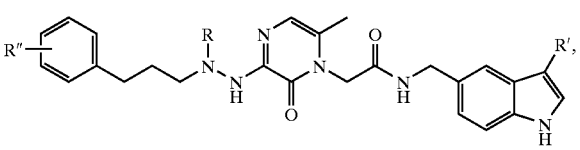
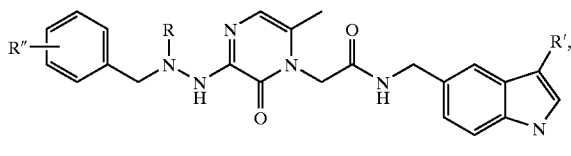
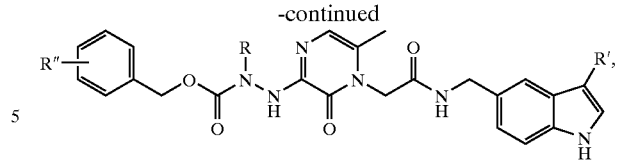
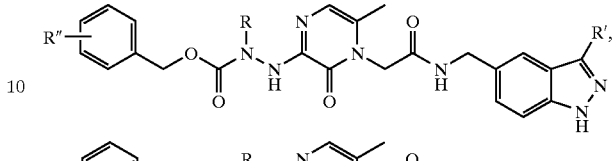
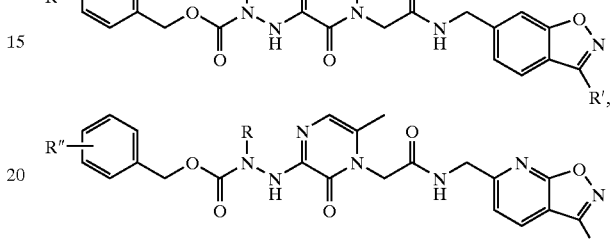
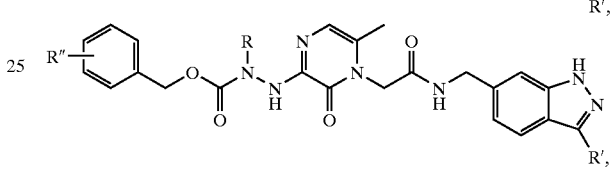
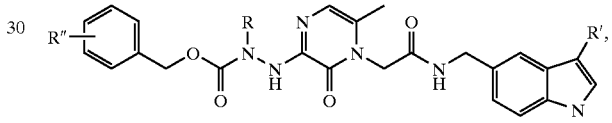
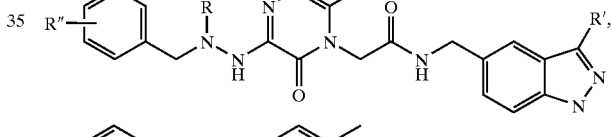
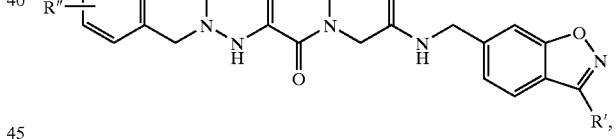
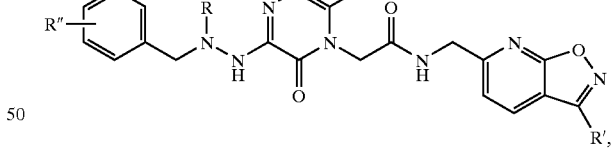
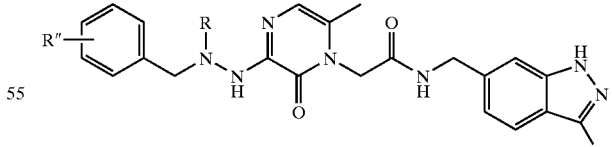
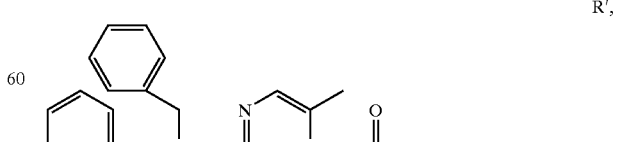
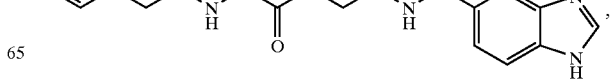

-continued

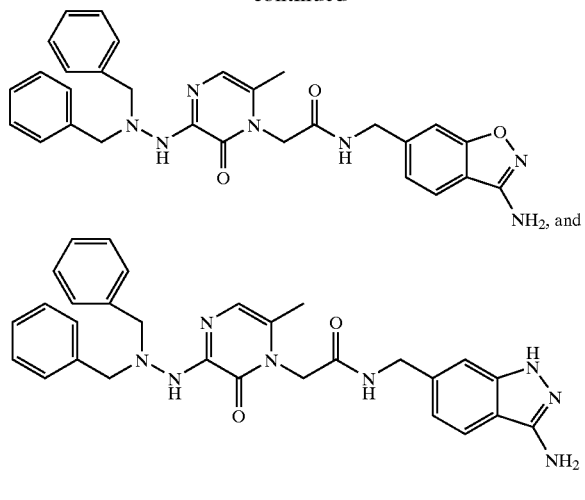

wherein R is H, —CH₃ or —CH₂CH₃; R' is H or NH₂ and R" is H, halogen, methoxy or CF₃.

18. A compound according to claim 1 wherein:
(a) V is —S(O)₂—, —O—C(=O)—, —NHC(=O)— or —C(=O)—;
(b) U and U' are direct links;
(c) T is phenyl, substituted phenyl, benzyl or substituted benzyl;
(d) T' is hydrogen;
(e) R₁ is hydrogen;
(f) R₂ is methyl; and
(g) R₃ is hydrogen.

19. A compound according to claim 1 wherein:
(a) V is —O—C(=O)— or —NH—C(=O)—;
(b) U is methylene or ethylene;
(c) U' is a direct link, methylene or ethylene;
(d) T is C₁₋₆ alkyl, C₂₋₆ alkenyl or C₂₋₆ alkynyl;
(e) T' is hydrogen;
(f) R₁ is hydrogen;
(g) R₂ is methyl; and
(h) R₃ is hydrogen.

20. A compound according to claim 1 wherein
(a) V is a direct link;
(b) U and U' are C₁₋₃ alkylene;
(c) T and T' are phenyl or substituted phenyl;
(d) R₁ is hydrogen;
(e) R₂ is methyl; and
(f) R₃ is hydrogen.

21. A compound of the formula

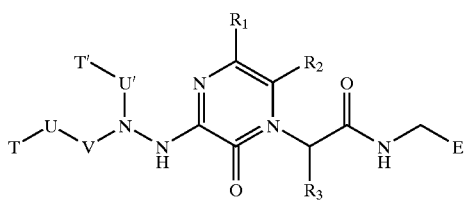

wherein
(a)
(i) V is —S(O)₂—, —O—C(=O)—, —NHC(=O)— or —C(=O)—; U and U' are both direct links; T is phenyl, phenyl substituted with alkoxy, trifluorourethyl or halogen; benzyl; or benzyl mono- or di-substituted with halogen, alkoxy or trifluromethyl or two substituents taken together are —OCH₂CH₂O—; and T' is hydrogen;
(ii) V is —O—C(=O)— or —NH—C(=O)—; U is methylene or ethylene; U' is a direct link, methylene or ethylene; T is C₁₋₆ alkyl, C₂₋₆ alkenyl or C₂₋₆ alkynyl and T' is hydrogen; or
(iii) V is a direct link, U and U' are C₁₋₃ alkylene, and T and T' are phenyl or substituted phenyl;
(b) R₁ is hydrogen;
(c) R₂ is mehtyl;
(d) R₃ is hydrogen; and
(e) E is

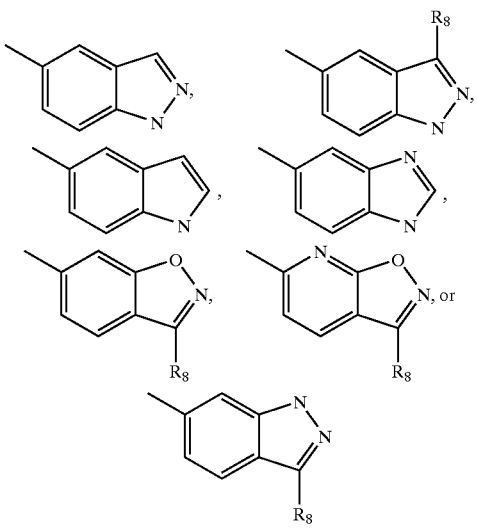

(1) —R₈ is NR₁₅R₁₆ or —OR₁₅;
(2) R₁₅ is hydrogen, alkyl of 1 to 3 carbon atoms or —C(=O)R₁₇;
(3) R₁₆ is hydrogen or alkyl of 1 to 3 carbon atoms;
(4) alternatively R₁₅ and R₁₆ taken together form a divalent radical of the formula —(CH₂)ᵥᵥ— where w is independently 3, 4 or 5; and
(5) R₁₇ is alkyl of 1 to 6 carbon atoms or alkoxy of 1 to 6 carbon atoms; and pharmaceutically acceptable salts thereof.

22. A pharmaceutical composition for treating or decreasing the incidence of a condition in a mammal characterized by abnormal thrombosis, comprising a therapeutically acceptable carrier, and a therapeutically effective amount of compound of claim 1.

23. A pharmaceutical composition for treating or decreasing the incidence of a condition in a mammal characterized by abnormal thrombosis, comprising a therapeutically acceptable carrier, and a therapeutically effective amount of compound of claim 2.

24. A pharmaceutical composition for treating or decreasing the incidence of a condition in a mammal characterized by abnormal thrombosis, comprising a therapeutically acceptable carrier, and a therapeutically effective amount of compound of claim 9.

25. A pharmaceutical composition for treating or decreasing the incidence of a condition in a mammal characterized by abnormal thrombosis, comprising a therapeutically acceptable carrier, and a therapeutically effective amount of compound of claim 10.

26. A pharmaceutical composition for treating or decreasing the incidence of a condition in a mammal characterized by abnormal thrombosis, comprising a therapeutically acceptable carrier, and a therapeutically effective amount of compound of claim 14.

27. A pharmaceutical composition for treating or decreasing the incidence of a condition in a mammal characterized by abnormal thrombosis, comprising a therapeutically acceptable carrier, and a therapeutically effective amount of compound of claim 17.

28. A method for treating or decreasing the incidence of a condition in a mammal characterized by abnormal thrombosis, comprising administering to said mammal a therapeutically effective amount of the compound of claim 1.

29. A method for treating or decreasing the incidence of a condition in a mammal characterized by abnormal thrombosis, comprising administering to said mammal a therapeutically effective amount of the compound of claim 2.

30. A method for treating or decreasing the incidence of a condition in a mammal characterized by abnormal thrombosis, comprising administering to said mammal a therapeutically effective amount of the compound of claim 9.

31. A method for treating or decreasing the incidence of a condition in a mammal characterized by abnormal thrombosis, comprising administering to said mammal a therapeutically effective amount of the compound of claim 10.

32. A method for treating or decreasing the incidence of a condition in a mammal characterized by abnormal thrombosis, comprising administering to said mammal a therapeutically-effective amount of the compound of claim 14.

33. A method for treating or decreasing the incidence of a condition in a mammal characterized by abnormal thrombosis, comprising administering to said mammal a therapeutically effective amount of the compound of claim 17.

* * * * *